United States Patent
Jiao et al.

(10) Patent No.: US 12,365,643 B2
(45) Date of Patent: Jul. 22, 2025

(54) PHENOXY CARBOXYLIC ACID COMPOUNDS AND MEDICAL USES THEREOF

(71) Applicant: QINGDAO RISING BIOTECHNOLOGY CO., LTD, Shandong (CN)

(72) Inventors: Ning Jiao, Beijing (CN); Siwang Yu, Beijing (CN); Song Song, Beijing (CN); Yameng Liu, Beijing (CN); Simin Yang, Beijing (CN)

(73) Assignee: QINGDAO RISING BIOTECHNOLOGY CO., LTD, Shandong (CN)

( * ) Notice: Subject to any disclaimer, the term of this patent is extended or adjusted under 35 U.S.C. 154(b) by 1130 days.

(21) Appl. No.: 17/182,413

(22) PCT Filed: Aug. 23, 2019

(86) PCT No.: PCT/CN2019/102273
§ 371 (c)(1),
(2) Date: Aug. 25, 2021

(87) PCT Pub. No.: WO2020/038464
PCT Pub. Date: Feb. 27, 2020

(65) Prior Publication Data
US 2022/0119333 A1    Apr. 21, 2022

(30) Foreign Application Priority Data
Aug. 23, 2018   (CN) .......................... 201810965558.1

(51) Int. Cl.
C07C 59/13   (2006.01)
A61K 45/06   (2006.01)
C07C 255/13   (2006.01)

(52) U.S. Cl.
CPC .............. C07C 59/13 (2013.01); A61K 45/06 (2013.01); C07C 255/13 (2013.01)

(58) Field of Classification Search
None
See application file for complete search history.

(56) References Cited

U.S. PATENT DOCUMENTS 3,674,836 A   7/1972  Creger
3,707,566 A   12/1972 Creger et al.
(Continued)

OTHER PUBLICATIONS

Cox (Cholesterol, Triglycerides, and Associated LipoproteinsClinical Methods: The History, Physical, and Laboratory Examinations. 3rd edition. Boston: Butterworths; 1990. Chapter 31. Available from: https://www.ncbi.nlm.nih.gov/books/NBK351/) (Year: 1990).*

(Continued)

Primary Examiner — Amy C Bonaparte
(74) Attorney, Agent, or Firm — ArentFox Schiff LLP; Joseph M. Maraia; Marlo Schepper Grolnic

(57) ABSTRACT

A phenoxy carboxylic acid compound, its pharmaceutically acceptable salt or ester, stereoisomer, prodrug, hydrate, solvate or crystal form, or metabolite form thereof, or any combination or mixture thereof; a pharmaceutical composition comprising the compound, its pharmaceutically acceptable salt or ester, stereoisomer, prodrug, hydrate, solvate or crystal form, or metabolite form thereof, or any combination or mixture thereof; and a medicinal use of the compound, its pharmaceutically acceptable salt or ester, stereoisomer, prodrug, hydrate, solvate or crystal form, or metabolite form thereof, or any combination or mixture thereof, for preventing and/or treatment of a metabolic disease (e.g., metabolic syndrome, non-alcoholic fatty liver disease, and/or diabetes mellitus).

11 Claims, 7 Drawing Sheets
Specification includes a Sequence Listing.

(56) References Cited

U.S. PATENT DOCUMENTS

| | | | |
|---|---|---|---|
| 3,759,986 A | | 9/1973 | Creger et al. |
| 3,847,994 A | | 11/1974 | Creger et al. |
| 5,281,421 A | * | 1/1994 | Ghebre-Sellassie ... A61K 47/26 514/975 |

OTHER PUBLICATIONS

Jana (Jana M, Pahan K. Gemfibrozil, a lipid lowering drug, inhibits the activation of primary human microglia via peroxisome proliferator-activated receptor β. Neurochem Res. Aug. 2012;37(8):1718-29. doi: 10.1007/s11064-012-0781-6. Epub Apr. 17, 2012. PMID: 22528839; PMCID: PMC3389313) (Year: 2012).*

Meanwell ("The Influence of Bioisosteres in Drug Design: Tactical Application to Address Developability Problems" Top Med Chem, 2015, p. 283-287) (Year: 2015).*

Narobe Rok et al: "Photocatalytic Oxidative Iodination of Electron-Rich Arenes", Advanced Synthesis and Catalysis, vol. 361, No. 17, Sep. 3, 2019 (Sep. 3, 2019), pp. 3998-4004, XP055923355, ISSN: 1615-4150, DOI: 10.1002/adsc.201900298; Retrieved from the Internet: URL:https://onlinelibrary.wiley.com/doi/full-XML/10.1002/adsc.201900298>.

Solakyildirim Kemal et al: "1 H and 13 CNMR spectral assignments of halogenated transformation products of pharmaceuticals and related environmental contaminants : 1 H and 13 C NMR spectral assignments of halogenated transformation products", Magnetic Resonance in Chemistry, vol. 52, No. 6, Jun. 1, 2014 (Jun. 1, 2014), pp. 310-317, XP055923364, GB ISSN: 0749-1581, DOI: 10.1002/mrc.4056.

Extended European Search Report dated Jun. 7, 2022, for related EP Application No. 19851778.1.

Office Action in Japanese Patent Application No. 2021-534420 [with English translation] dated May 12, 2023, 6 pages.

Registry (STN) [online], Nov. 3, 2013, RN 1468023-20-2, 3 pages.

Registry (STN) [online], Dec. 15, 2013, RN 1495556-61-0, 2 pages.

International Search Report and Written Opinion mailed Nov. 22, 2019, for related International Application No. PCT/CN2019/102273.

Creger, P. L. et al. "Structure/Activity Relationship of Gemfibrozil (CI-719) and Related Compounds" Proc. roy. Soc. Med., vol. 69, Dec. 31, 1976 (Dec. 31, 1976), p. 4, table 3.

First Chinese Office Action dated Nov. 18, 2021, Application No. 201910783280.0.

STN RN 2139740-94-4, 2009713-28-2, 2142154-52-5, 1971711-36-0, 1493932-49-2, 1491629-83-4, 1467186-48-6: STN, obtained Nov. 10, 2021.

Krkosek; et al., "Formation Kinetics of Gemfibrozil Chlorination Reaction Products: Analysis and Application," Water Environment Research, vol. 86, No. 7, pp. 654-662, 2014.

* cited by examiner

PHENOXY CARBOXYLIC ACID COMPOUNDS AND MEDICAL USES THEREOF

CROSS REFERENCE TO RELATED APPLICATIONS

This is a U.S. National Stage Application, filed under 35 U.S.C. 371, of International Patent Application No. PCT/CN2019/102273, filed on Aug. 23, 2019, which claims priority to Chinese patent application No. 201810965558.1 filed on Aug. 23, 2018, contents of both of which are incorporated herein by reference in their entireties.

TECHNICAL FIELD

The present invention pertains to the field of medical technology. In particular, the present invention relates to a phenoxy carboxylic acid compound, a pharmaceutical composition comprising the compound, and a medical use of the compound. For example, the compound of the present invention can be used to prevent and/or treat a metabolic disease and a complication of such disease.

BACKGROUND ART

With the development of society and economy, the incidence of metabolic diseases such as diabetes mellitus, obesity, fatty liver disease and metabolic syndrome has been increasing. These diseases are not only related to each other, but also cause a variety of serious complications and a significant increase in the risk of other major diseases such as cancers and cardiovascular and cerebrovascular diseases, and have become one of the greatest threats to human health.

Although people have invested a lot of manpower and material resources in long-term research on the pathogenesis and treatment of metabolic diseases, the current treatment options are still very limited. For example, the global incidence of diabetes mellitus is rising rapidly, with hundreds of millions of people suffering from diabetes mellitus, especially type II diabetes mellitus, who account for majority of patients. There are many drugs for diabetes mellitus, such as insulin drugs, insulinotropic drugs (including sulfonylureas), insulin sensitizing agents (thiazolidinediones, biguanides), α-glycosidase inhibitors (acarbose, voglibose, miglitol), human glucagon-like peptide (GLP-1) receptor agonists, dipeptidyl peptidase 4 (DPP-4) inhibitors, sodium-glucose cotransporter 2 (SGLT2) inhibitors and other drugs, but these drugs are usually accompanied by weight gain, limited tolerance, hyperinsulinemia, hypoglycemia, gastrointestinal symptoms and other side effects, as well as gradual decline in drug efficacy. Diabetes mellitus can also cause various complications such as nephropathy/cardio-cerebrovascular disease/eye disease/neuropathy/ulcers, and these complications are extremely difficult to reverse once they occur. The prevention and treatment drugs for them have always been research hotspots, but so far there is no targeted drug, while the effects of using other symptomatic drugs or combination therapies have also been unsatisfactory. For another example, non-alcoholic steatohepatitis (NASH) is one of the most common chronic liver diseases and may develop into liver fibrosis, cirrhosis and even liver cancer, and is also one of the most common causes of liver transplantation. Its main treatment strategies include (1) metabolic regulation; (2) inhibition of inflammation or oxidative damage; (3) regulation of hepatic and enteric circulation and/or intestinal flora. Many drugs, including hypoglycemic drugs (e.g., metformin, thiazolidinediones), antioxidants (vitamin E, reduced glutathione), lipid-lowering drugs (statins, fibrates), ursodeoxycholic acid and other drugs, have been tried for treating NASH, but there is no drug approved by the FDA for the treatment of NASH. The main treatment plan is still lifestyle intervention.

In short, the currently available drugs for metabolic diseases are limited by some important defects, some important metabolic diseases such as steatohepatitis do not even have any approved treatment drugs, the complications of these metabolic diseases are a serious threat for health and life safety, and it is urgent to find new drugs for the treatment of metabolic diseases and preventive drugs for complications of metabolic diseases.

Contents of the Present Invention

Through in-depth research and creative discovery, the inventors of the present application have obtained a class of phenoxy carboxylic acid compounds, which have significant activity in regulating glycolipid metabolism, anti-inflammatory activity and/or antioxidant activity, thereby providing the present invention as follows.

Compound

In the first aspect, the present invention provides a compound represented by Formula (I), its pharmaceutically acceptable salt or ester, prodrug, stereoisomer, hydrate, solvate or crystal form, or metabolite form thereof, or any combination or mixture thereof,

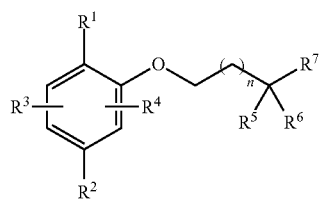

Formula (I)

wherein, $R^1$ and $R^2$ are each independently selected from the group consisting of $C_1$-$C_4$ alkyl and $C_1$-$C_4$ alkoxy, and the $C_1$-$C_4$ alkyl or $C_1$-$C_4$ alkoxy is optionally substituted with one or several (e.g., 1, 2, 3 or 4) substituents independently selected from the group consisting of: halogen (e.g., —F, —Cl, —Br or —I), nitro, amino, hydroxyl and thiol;

$R^3$ and $R^4$ are each independently selected from the group consisting of hydrogen, halogen (e.g., —F, —Cl, —Br or —I), nitro, amino, hydroxyl, thiol, $C_1$-$C_4$ alkyl, $C_1$-$C_4$ alkoxy, $C_1$-$C_4$ alkylthio and $C_1$-$C_4$ alkylamino; wherein the amino, hydroxyl, thiol, $C_1$-$C_4$ alkyl, $C_1$-$C_4$ alkoxy, $C_1$-$C_4$ alkylthio or $C_1$-$C_4$ alkylamino is optionally substituted with one or several (e.g., 1, 2, 3 or 4) substituents independently selected from the group consisting of: halogen (e.g., —F, —Cl, —Br or —I), amino and hydroxyl;

wherein, at least one of $R^3$ and $R^4$ is halogen;

$R^5$ and $R^6$ are each independently selected from the group consisting of $C_1$-$C_4$ alkyl;

$R^7$ is selected from the group consisting of —C(O)X and cyano; wherein X is hydroxyl or $C_1$-$C_4$ alkoxy;

n is 1, 2, 3 or 4;

provided that the compound is not 5-(2,4-dichloro-3,6-dimethylphenoxy)-2,2-dimethylpentanoic acid; 5-(4-chloro-2,5-dimethylphenoxy)-2,2-dimethylpentanoic acid; 5-(2-chloro-3,6-dimethylphenoxy)-2,2-dimethylpentanoic acid; or 5-(4-bromo-2,5-dimethyl-phenoxy)-2,2-dimethylpentanoic acid.

In certain embodiments, $R^1$ and $R^2$ are each independently selected from the group consisting of $C_1$-$C_4$ alkyl and $C_1$-$C_4$ alkoxy, and the $C_1$-$C_4$ alkyl or $C_1$-$C_4$ alkoxy is optionally substituted with one or several (e.g., 1, 2, 3 or 4) substituents independently selected from the group consisting of: halogen (e.g., —F, —Cl, —Br, or —I) and hydroxyl.

In certain embodiments, $R^1$ and $R^2$ are each independently selected from the group consisting of methyl, ethyl, methoxy and ethoxy, and the methyl, ethyl, methoxy or ethoxy is optionally substituted with one or several (e.g., 1, 2, 3 or 4) substituents independently selected from the group consisting of: —F, —Cl, —Br, —I and hydroxyl.

In certain embodiments, $R^1$ and $R^2$ are each independently selected from the group consisting of methyl, hydroxy-substituted methyl, ethyl and methoxy.

In certain embodiments, $R^3$ and $R^4$ are each independently selected from the group consisting of hydrogen, halogen (e.g., —F, —Cl, —Br or —I), nitro, hydroxy and $C_1$-$C_4$ alkyl; wherein the hydroxy or $C_1$-$C_4$ alkyl is optionally substituted with one or several (e.g., 1, 2, 3 or 4) substituents independently selected from the group consisting of halogen (e.g., —F, —Cl, —Br or —I) and hydroxyl.

In certain embodiments, $R^3$ and $R^4$ are each independently selected from the group consisting of hydrogen, —F, —Cl, —Br, —I, nitro, hydroxyl, methyl and ethyl; wherein, the hydroxyl, methyl or ethyl is optionally substituted with one or several (e.g., 1, 2, 3 or 4) substituents independently selected from the group consisting of halogen (e.g., —F, —Cl, —Br, or —I) and hydroxyl.

In certain embodiments, $R^3$ and $R^4$ are independently selected from the group consisting of hydrogen, —F, —Cl, —Br, —I, nitro, hydroxyl and methyl.

In certain embodiments, $R^5$ and $R^6$ are the same as each other. In certain embodiments, $R^5$ and $R^6$ are methyl.

In certain embodiments, $R^7$ is selected from the group consisting of carboxy, —$CO_2Me$, —$CO_2Et$ and cyano.

In certain embodiments, n is 1, 2 or 3.

In certain embodiments, the compound has the following characteristics:
$R^1$ and $R^2$ are each independently selected from the group consisting of methyl, ethyl, methoxy and ethoxy, and the methyl, ethyl, methoxy or ethoxy is optionally substituted with one or several (e.g., 1, 2, 3 or 4) substituents independently selected from the group consisting of: —F, —Cl, —Br, —I and hydroxyl; preferably, $R^1$ and $R^2$ are each independently selected from the group consisting of methyl, hydroxyl-substituted methyl, ethyl and methoxy;
$R^3$ and $R^4$ are each independently selected from the group consisting of hydrogen, —F, —Cl, —Br, —I, nitro, hydroxy, methyl and ethyl; wherein the hydroxy, methyl or ethyl is optionally substituted with one or several (e.g., 1, 2, 3 or 4) substituents independently selected from the group consisting of halogen (e.g., —F, —Cl, —Br, or —I) and hydroxyl; preferably, $R^3$ and $R^4$ are each independently selected from the group consisting of hydrogen, —F, —Cl, —Br, —I, nitro, hydroxyl and methyl;
$R^5$ and $R^6$ are methyl;
$R^7$ is selected from the group consisting of carboxy, —$CO_2Me$, —$CO_2Et$ and cyano;
n is 1, 2 or 3.

In certain embodiments, the compound has a structure represented by Formula (Ia):

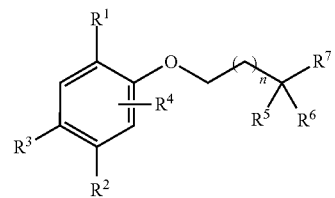

Formula (Ia)

wherein,
$R^3$ is halogen (e.g., —F, —Cl, —Br or —I);
$R^1$, $R^2$, $R^4$, $R^5$, $R^6$, $R^7$ and n are as defined above (as defined in Formula (I)).

In certain embodiments, the compound is selected from:
5-(4-fluoro-2,5-dimethylphenoxy)-2,2-dimethylpentanoic acid (BJMU-3);
5-(2,4-dibromo-3,6-dimethylphenoxy)-2,2-dimethylpentanoic acid (BJMU-109);
5-(3-fluoro-2,5-dimethylphenoxy)-2,2-dimethylpentanoic acid (BJMU-213);
5-(4-bromo-2,5-diethylphenoxy)-2,2-dimethylpentanoic acid (BJMU-310);
5-(4-bromo-2,3,5-trimethylphenoxy)-2,2-dimethylpentanoic acid (BJMU-315);
5-(2-bromo-3,6-dimethylphenoxy)-2,2-dimethylpentanoic acid (BJMU-404);
5-(4-bromo-2,3,6-trimethylphenoxy)-2,2-dimethylpentanoic acid (BJMU-409);
5-(4-bromo-2-iodo-3,6-dimethylphenoxy)-2,2-dimethylpentanoic acid (BJMU-413);
5-(4-bromo-2-methoxy-5-methylphenoxy)-2,2-dimethylpentanoic acid (BJMU-412);
5-(4-bromo-3,6-dimethyl-2-nitrophenoxy)-2,2-dimethylpentanoic acid (BJMU-414);
5-(4-bromo-2-hydroxy-3,6-dimethylphenoxy)-2,2-dimethylpentanoic acid (BJMU-415);
5-(4-bromo-3-hydroxy-2,5-dimethylphenoxy)-2,2-dimethylpentanoic acid (BJMU-416);
5-(4-bromo-2-(hydroxymethyl)-5-methylphenoxy)-2,2-dimethylpentanoic acid (BJMU-502);
5-(4-bromo-2,5-dimethylphenoxy)-2,2-dimethylvaleronitrile (BJMU-309);
5-(4-bromo-2,5-dimethylphenoxy)-2-ethyl-2-methylpentanoic acid (BJMU-401);
5-(2,5-dimethyl-4-nitrophenoxy)-2,2-dimethylpentanoic acid (BJMU-110);
5-(4-bromo-2-ethyl-5-methylphenoxy)-2,2-dimethylpentanoic acid (BJMU-410);
5-(4-bromo-2,5-dimethoxyphenoxy)-2,2-dimethylpentanoic acid (BJMU-201);
4-(4-bromo-2,5-dimethylphenoxy)-2,2-dimethylbutanoic acid (BJMU-111);
6-(4-bromo-2,5-dimethylphenoxy)-2,2-dimethylhexanoic acid (BJMU-403).

Pharmaceutical Composition

In the second aspect, the present invention provides a pharmaceutical composition comprising a compound represented by Formula (I), its pharmaceutically acceptable salt or ester, prodrug, stereoisomer, hydrate, solvate or crystal form, or metabolite form thereof, or any combination or mixture thereof, and one or more pharmaceutically acceptable carriers and/or excipients;

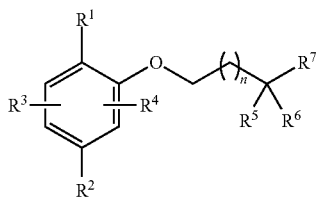

Formula (I)

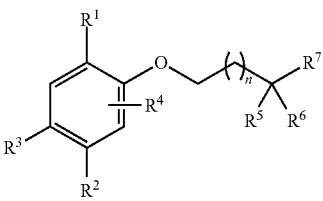

Formula (Ia)

wherein,
R¹ and R² are each independently selected from the group consisting of $C_1$-$C_4$ alkyl and $C_1$-$C_4$ alkoxy, and the $C_1$-$C_4$ alkyl or $C_1$-$C_4$ alkoxy is optionally substituted with one or several (e.g., 1, 2, 3 or 4) substituents independently selected from the group consisting of: halogen (e.g., —F, —Cl, —Br or —I), nitro, amino, hydroxyl and thiol;
R³ and R⁴ are each independently selected from the group consisting of hydrogen, halogen (e.g., —F, —Cl, —Br or —I), nitro, amino, hydroxyl, thiol, $C_1$-$C_4$ alkyl, $C_1$-$C_4$ alkoxy, $C_1$-$C_4$ alkylthio and $C_1$-$C_4$ alkylamino; wherein the amino, hydroxyl, thiol, $C_1$-$C_4$ alkyl, $C_1$-$C_4$ alkoxy, $C_1$-$C_4$ alkylthio or $C_1$-$C_4$ alkylamino is optionally substituted with one or several (e.g., 1, 2, 3 or 4) substituents independently selected from the group consisting of: halogen (e.g., —F, —Cl, —Br or —I), amino and hydroxyl;
wherein, at least one of R³ and R⁴ is halogen;
R⁵ and R⁶ are each independently selected from the group consisting of $C_1$-$C_4$ alkyl;
R⁷ is selected from the group consisting of —C(O)X and cyano; wherein X is hydroxyl or $C_1$-$C_4$ alkoxy;
n is 1, 2, 3 or 4.
In certain embodiments, R¹, R², R³, R⁴, R⁵, R⁶, R⁷ and n are as defined in the first aspect.
In certain embodiments, the compound has a structure represented by Formula (Ia), wherein, R³ is halogen (e.g., —F, —Cl, —Br or —I); R¹, R², R⁴, R⁵, R⁶, R⁷ and n are as defined in Formula (I).
In certain embodiments, the compound has a structure represented by Formula (Ia), wherein:
R¹ and R² are each independently selected from the group consisting of methyl, ethyl, methoxy and ethoxy, and the methyl, ethyl, methoxy or ethoxy is optionally substituted with one or several (e.g., 1, 2, 3 or 4) substituents independently selected from the group consisting of: —F, —Cl, —Br, —I and hydroxyl; preferably, R¹ and R² are each independently selected from the group consisting of methyl, hydroxyl-substituted methyl, ethyl and methoxy;
R⁴ is selected from the group consisting of hydrogen, —F, —Cl, —Br, —I, nitro, hydroxyl, methyl and ethyl; wherein the hydroxyl, methyl or ethyl is optionally substituted with one or several (e.g., 1, 2, 3 or 4) substituents independently selected from the group consisting of halogen (e.g., —F, —Cl, —Br, or —I) and hydroxyl; preferably, R⁴ is selected from the group consisting of hydrogen, —F, —Cl, —Br, —I, nitro, hydroxyl and methyl;
R⁵ and R⁶ are methyl;
R⁷ is selected from the group consisting of carboxy, —CO₂Me, —CO₂Et and cyano;
n is 1, 2 or 3.
In certain embodiments, the compound is selected from:

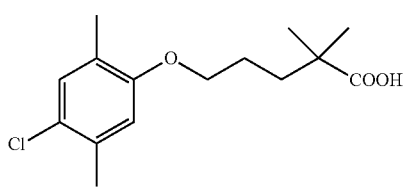 [SMILES: Cc1cc(OCCCC(C)(C)C(=O)O)c(C)cc1Cl]

5-(4-chloro-2,5-dimethylphenoxy)-2,2-dimethylpentanoic acid     BJMU-1

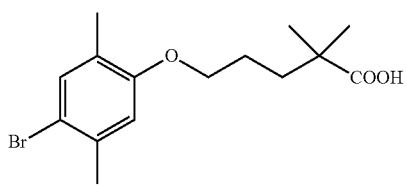

5-(4-bromo-2,5-dimethylphenoxy)-2,2-dimethylpentanoic acid     BJMU-2

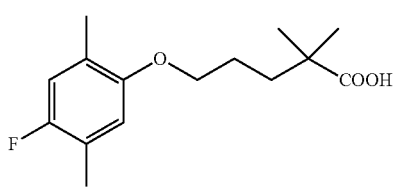 [SMILES: Cc1cc(OCCCC(C)(C)C(=O)O)c(C)cc1F]

5-(4-fluoro-2,5-dimethylphenoxy)-2,2-dimethylpentanoic acid     BJMU-3

-continued

| | | |
|---|---|---|
| 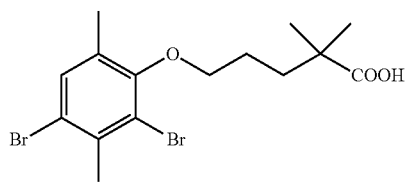 [SMILES: Cc1cc(Br)c(C)c(Br)c1OCCCC(C)(C)C(=O)O] | 5-(2,4-dibromo-3,6-dimethylphenoxy)-2,2-dimethylpentanoic acid | BJMU-109 |
| 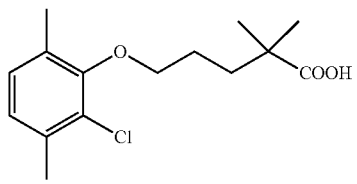 | 5-(2-chloro-3,6-dimethylphenoxy)-2,2-dimethylpentanoic acid | BJMU-209 |
| 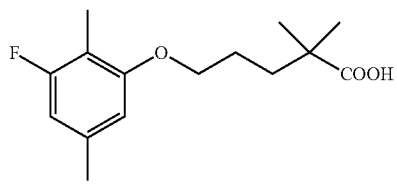 [SMILES: Cc1cc(F)c(C)c(OCCCC(C)(C)C(=O)O)c1] | 5-(3-fluoro-2,5-dimethylphenoxy)-2,2-dimethylpentanoic acid | BJMU-213 |
| 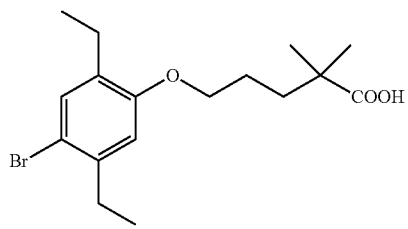 [SMILES: CCc1cc(OCCCC(C)(C)C(=O)O)c(CC)cc1Br] | 5-(4-bromo-2,5-diethylphenoxy)-2,2-dimethylpentanoic acid | BJMU-310 |
| 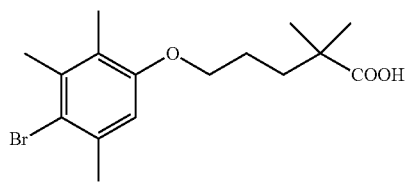 [SMILES: Cc1cc(OCCCC(C)(C)C(=O)O)c(C)c(C)c1Br] | 5-(4-bromo-2,3,5-trimethylphenoxy)-2,2-dimethylpentanoic acid | BJMU-315 |
| 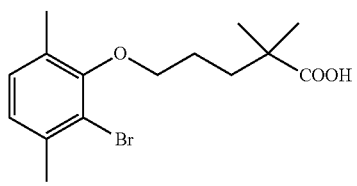 [SMILES: Cc1ccc(C)c(OCCCC(C)(C)C(=O)O)c1Br] | 5-(2-bromo-3,6-dimethylphenoxy)-2,2-dimethylpentanoic acid | BJMU-404 |
| 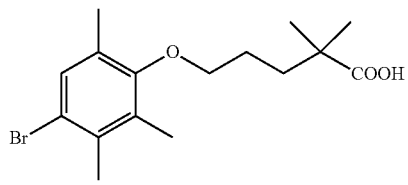 [SMILES: Cc1cc(Br)c(C)c(I)c1OCCCC(C)(C)C(=O)O] | 5-(4-bromo-2,3,6-trimethylphenoxy)-2,2-dimethylpentanoic acid | BJMU-409 |
| 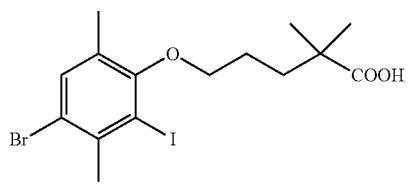 | 5-(4-bromo-2-iodo-3,6-dimethylphenoxy)-2,2-dimethylpentanoic acid | BJMU-413 |

-continued

| | | |
|---|---|---|
| 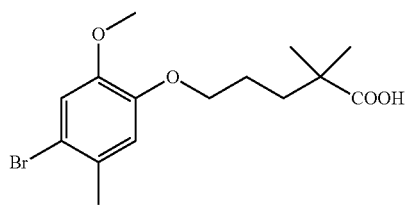 | 5-(4-bromo-2-methoxy-5-methylphenoxy)-2,2-dimethylpentanoic acid | BJMU-412 |
| 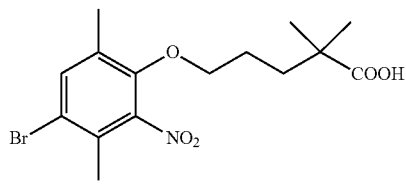 [SMILES: Cc1cc(Br)c(C)c([N+](=O)[O-])c1OCCCC(C)(C)C(=O)O] | 5-(4-bromo-3,6-dimethyl-2-nitrophenoxy)-2,2-dimethylpentanoic acid | BJMU-414 |
| 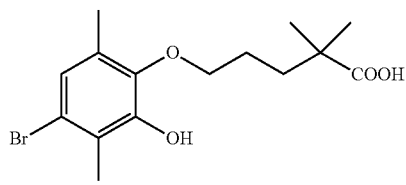 [SMILES: Cc1cc(Br)c(C)c(O)c1OCCCC(C)(C)C(=O)O] | 5-(4-bromo-2-hydroxy-3,6-dimethylphenoxy)-2,2-dimethylpentanoic acid | BJMU-415 |
| 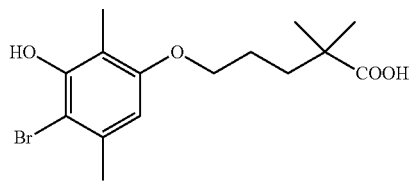 [SMILES: Cc1cc(OCCCC(C)(C)C(=O)O)c(C)c(O)c1Br] | 5-(4-bromo-3-hydroxy-2,5-dimethylphenoxy)-2,2-dimethylpentanoic acid | BJMU-416 |
| 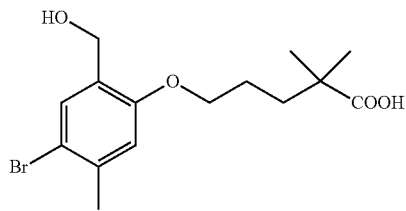 [SMILES: Cc1cc(OCCCC(C)(C)C(=O)O)c(CO)cc1Br] | 5-(4-bromo-2-(hydroxymethyl)-5-methylphenoxy)-2,2-dimethylpentanoic acid | BJMU-502 |
| 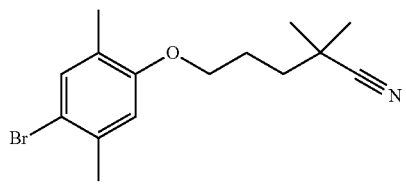 [SMILES: Cc1cc(OCCCC(C)(C)C#N)c(C)cc1Br] | 5-(4-bromo-2,5-dimethylphenoxy)-2,2-dimethylpentanenitrile | BJMU-309 |
| 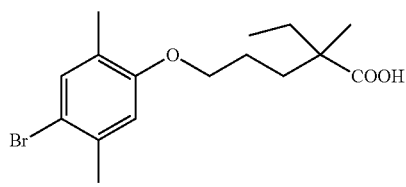 | 5-(4-bromo-2,5-dimethylphenoxy)-2-ethyl-2-methylpentanoic acid | BJMU-401 |
| 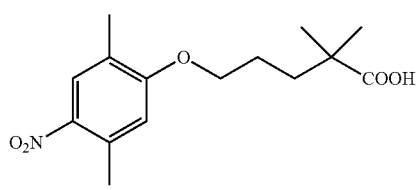 [SMILES: Cc1cc([N+](=O)[O-])c(C)cc1OCCCC(C)(C)C(=O)O] | 5-(2,5-dimethyl-4-nitrophenoxy)-2,2-dimethylpentanoic acid | BJMU-110 |

-continued

| Structure | Name | Code |
|---|---|---|
| 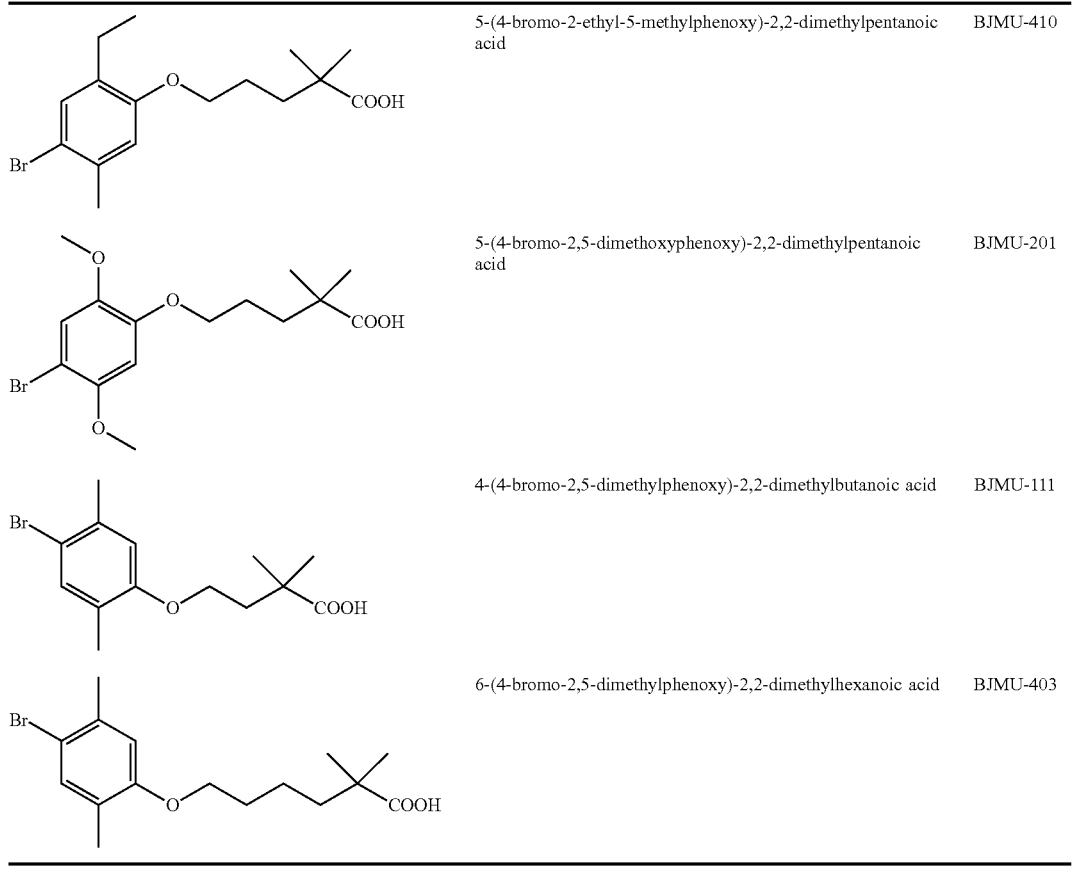 | 5-(4-bromo-2-ethyl-5-methylphenoxy)-2,2-dimethylpentanoic acid | BJMU-410 |
| 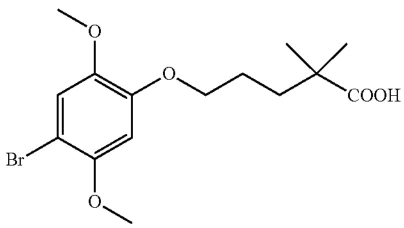 [SMILES: COc1cc(OCCCC(C)(C)C(=O)O)c(OC)cc1Br] | 5-(4-bromo-2,5-dimethoxyphenoxy)-2,2-dimethylpentanoic acid | BJMU-201 |
| 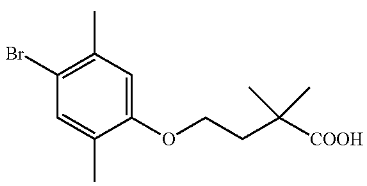 [SMILES: Cc1cc(OCCC(C)(C)C(=O)O)c(C)cc1Br] | 4-(4-bromo-2,5-dimethylphenoxy)-2,2-dimethylbutanoic acid | BJMU-111 |
| 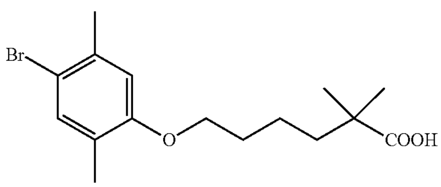 [SMILES: Cc1cc(OCCCCC(C)(C)C(=O)O)c(C)cc1Br] | 6-(4-bromo-2,5-dimethylphenoxy)-2,2-dimethylhexanoic acid | BJMU-403 |

In a third aspect, the present invention provides a pharmaceutical composition comprising a compound represented by Formula (Ia), its pharmaceutically acceptable salt or ester, prodrug, stereoisomer, hydrate, solvate or crystal form, or metabolite form thereof, or any combination or mixture thereof, and one or more pharmaceutically acceptable carriers and/or excipients,

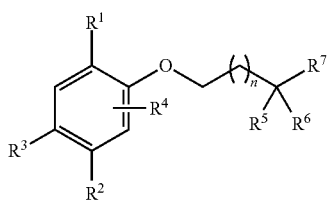

Formula (Ia)

wherein,
$R^1$ and $R^2$ are each independently selected from the group consisting of methyl, hydroxy-substituted methyl, ethyl, and methoxy;
$R^3$ is selected from the group consisting of —F, —Cl, —Br and —I;
$R^4$ is selected from hydrogen or hydroxyl;
$R^5$ and $R^6$ are methyl;
$R^7$ is selected from the group consisting of carboxy, —CO$_2$Me, —CO$_2$Et and cyano;
n is 1, 2 or 3.

In certain embodiments, the compound is selected from the group consisting of BJMU-1, BJMU-2, BJMU-3, BJMU-415, BJMU-502, BJMU-309, BJMU-11 and BJMU-403.

In certain embodiments, the pharmaceutical composition of the second or third aspect optionally comprises an additional pharmaceutically active agent.

In certain embodiments, the additional pharmaceutically active agent is selected from the group consisting of anti-diabetic drug, anti-obesity drug, anti-hypertensive drug, anti-atherosclerosis drug, lipid-lowering drug, anti-inflammatory drug, and anti-oxidative damage drug.

In the present invention, the pharmaceutical composition may be in any form known in the medical field. For example, the pharmaceutical composition may be a form of tablet, pill, suspension, emulsion, solution, gel, capsule, powder, granule, elixir, lozenge, suppository, injection (including injection solution, lyophilized powder), inhalant, spray, etc. The preferred dosage form depends on the intended mode of administration and therapeutic use.

In certain embodiments, the compound of the present invention, its pharmaceutically acceptable salt or ester, prodrug, stereoisomer, hydrate, solvate or crystal form, or metabolite form thereof, or any combination or mixture thereof, may be present in the pharmaceutical composition in unit dosage form for ease of administration.

The compound of the present invention, its pharmaceutically acceptable salt or ester, prodrug, stereoisomer, hydrate, solvate or crystal form, or metabolite form thereof, or any combination or mixture thereof, or the pharmaceutical composition of the present invention can be administered by any suitable method known in the art, including but not limited to oral, rectal, parenteral or topical administration.

An exemplary route of administration is oral administration. Liquid dosage form for oral administration includes pharmaceutically acceptable emulsion, microemulsion, solution, suspension, syrup, elixir and the like. In addition to the active compound, the liquid dosage form may contain an inert diluent commonly used in the art, such as water or other solvent, solubilizer and emulsifier, such as ethanol, isopropanol, ethyl acetate, benzyl alcohol, benzyl benzoate, propylene glycol, 1,3-butanediol, dimethylformamide, oil (e.g., cottonseed oil, peanut oil, corn oil, germ oil, olive oil, castor oil and sesame oil), glycerin, tetrahydrofurfuryl alcohol, polyethylene glycol, and fatty acid ester of sorbitan as well as mixtures thereof. In addition to inert diluent, liquid dosage form for oral administration may also include adjuvant, such as wetting agent, emulsifier and suspending agent, sweetening agent, flavoring agent, and fragrance. Solid dosage form for oral administration includes capsule, tablet, pill, lozenge, powder, granule and the like. In addition to the active compound, the solid dosage form may contain pharmaceutically acceptable inert excipient or carrier, such as filler (e.g., lactose, sucrose, glucose, mannitol, starch, microcrystalline cellulose, galactose, crospovidone and calcium sulfate); binder (e.g., carboxymethyl cellulose, alginate, gelatin, polyvinylpyrrolidone, sucrose and acacia); wetting agent (e.g., cetyl alcohol and glyceryl monostearate); disintegrant (e.g., agar, calcium carbonate, starch, alginic acid, sodium carboxymethyl cellulose, sodium carboxymethyl starch); lubricant (e.g., talc, calcium stearate, magnesium stearate, solid polyethylene glycol, sodium laurel sulfate); and mixtures thereof.

The compound or pharmaceutical composition of the present invention can also be administered by a non-oral route.

Therefore, another exemplary route of administration is parenteral administration, for example, subcutaneous injection, intravenous injection, intraperitoneal injection, intramuscular injection, intrasternal injection, and infusion. The dosage form for parenteral administration may be an injection preparation, including injection solution, sterile powder for injection, or concentrated solution for injection. In addition to the active compound, the injection dosage form may contain a pharmaceutically acceptable carrier such as sterile water, Ringer's solution and isotonic sodium chloride solution. An appropriate additive such as antioxidant, buffer and bacteriostatic agent may also be added depending on the nature of the drug.

Another exemplary route of administration is topical administration, such as transdermal administration (e.g., administration via a transdermal patch or iontophoresis device), intraocular administration, or intranasal or inhalation administration. The dosage form for transdermal administration can be a topical gel, spray, ointment and cream. In addition to the active compound, topical dosage form may contain an ingredient that enhances the absorption or penetration of the active compound through the skin or other areas of action. When the compound of the present invention is administered via a transdermal device, the administration will be accomplished using a patch of storage and porous membrane type or solid matrix variety. The dosage form for topical administration to the eye may be an eye drop, in which the compound of the present invention is dissolved or suspended in a suitable carrier. For intranasal administration or inhalation administration, the compound of the present invention in the form of a solution or suspension is conveniently delivered from a pressure spray container, and the delivery is carried out by the patient's compression or pumping, or it is delivered as an aerosol spray formulation from a pressure vessel or sprayer using a suitable propellant.

Another exemplary route of administration is rectal administration. The dosage form for rectal administration may be a suppository.

In addition, other carrier materials and administration methods known in the pharmaceutical field can also be used. The pharmaceutical composition of the present invention can be prepared by any well-known pharmaceutical process, such as effective formulation and administration method. The aforementioned considerations regarding effective formulation and administration method are well known in the art and described in standard textbooks. The formulation of pharmaceuticals is described in, for example, Hoover, John E., Remington's Pharmaceutical Sciences. Mack Publishing Co., Easton, Pennsylvania, 1975; Liberman et al., Pharmaceutical Dosage Forms, Marcel Decker, New York, NY, 1980; and Kibbe et al., Handbook of Pharmaceutical Excipients (3rd edition), American Pharmaceutical Association, Washington, 1999.

In certain embodiments, the pharmaceutical composition comprises the compound of the present invention, its pharmaceutically acceptable salt or ester, prodrug, stereoisomer, hydrate, solvate or crystal form, or metabolite form thereof, or any combination or mixture thereof, in an amount of 0.01 to 2000 mg, preferably 0.1 to 1000 mg, more preferably 1 to 800 mg, more preferably 10 to 600 mg, and particularly preferably 50 to 500 mg.

The pharmaceutical composition of the present invention may comprise a "therapeutically effective amount" or "prophylactically effective amount" of the compound as described herein, its pharmaceutically acceptable salt or ester, prodrug, stereoisomer, hydrate, solvate or crystal form, or metabolite form thereof, or any combination or mixture thereof. The term "prophylactically effective amount" refers to an amount sufficient to prevent, stop, or delay the occurrence of a disease. The term "therapeutically effective amount" refers to an amount sufficient to cure or at least partially prevent a disease and complication thereof in a patient who has already suffered from the disease. Those skilled in the art understand that the compound as described herein, its pharmaceutically acceptable salt or ester, prodrug, stereoisomer, hydrate, solvate or crystal form, or metabolite form thereof, or any combination or mixture thereof, may have a therapeutically effective amount varying according to the following factors: severity of disease to be treated, overall state of patient's own immune system, patient's general conditions such as age, weight and gender, administration mode of drug, and other treatments simultaneously administered, etc.

In the present invention, the dosage regimen can be adjusted to obtain the best objective response (e.g., therapeutic or preventive response). For example, it can be administered in a single dose, can be administered multiple times over a period of time, or the dose can be reduced or increased proportionally to the urgency of the treatment situation.

The compound of the present invention, its pharmaceutically acceptable salt or ester, prodrug, stereoisomer, hydrate, solvate or crystal form, or metabolite form thereof, or any combination or mixture thereof, has a therapeutically or prophylactically effective amount with a typical and non-limiting range of 0.01 to 1000 mg/kg, for example 0.1 to 500 mg/kg. It should be noted that the dosage may vary with the type and severity of the symptoms to be treated. In addition, those skilled in the art understand that for any specific patient, the specific dosage regimen should be adjusted over time based on the patient's needs and the doctor's professional evaluation; the dosage range given here is for illustrative purposes only, and does not limit the use or scope of the pharmaceutical composition of the present invention.

In certain embodiments, the pharmaceutical composition may also comprise an additional pharmaceutically active agent. In certain embodiments, the additional pharmacologically active agent is a drug used to treat a metabolic disease or a related disease, such as anti-diabetic drug, anti-obesity drug, anti-hypertensive drug, anti-atherosclerotic drug or lipid-lowering drug. In certain embodiments, the additional pharmaceutically active agent is a drug with anti-inflammatory activity. In certain embodiments, the additional pharmaceutically active agent is a drug with anti-oxidative damage activity. In certain embodiments, the additional pharmaceutically active agent is selected from the group consisting of anti-diabetic drug, anti-obesity drug, anti-hypertensive drug, anti-atherosclerosis drug, lipid-lowering drug, anti-inflammatory drug, and anti-oxidative damage drug.

In certain embodiments, in the pharmaceutical composition, the compound of the present invention, its pharmaceutically acceptable salt or ester, prodrug, stereoisomer, hydrate, solvate or crystal form, or metabolic form thereof, or any combination or mixture thereof, and the additional pharmaceutically active agent are provided as separate components or mixed components. Therefore, the compound of the present invention, its pharmaceutically acceptable salt or ester, prodrug, stereoisomer, hydrate, solvate or crystal form, or metabolite form thereof, or any combination or mixture thereof and the additional pharmaceutically active agent can be administered simultaneously, separately or sequentially.

General Synthesis

The compound described in the first aspect of the present invention and the compound defined in the second aspect or third aspect of the present invention can be prepared by various methods known for preparing this type of compound, for example, as shown in the following reaction scheme. Unless otherwise specified, $R^1$ to $R^7$ and n in the reaction scheme and the following discussion are as defined above.

The following reaction scheme illustrates the preparation of the compound of Formula (I).

Scheme 1:

This scheme illustrates the preparation of a compound of Formula (I-1), where $R^7$ represents —COOH.

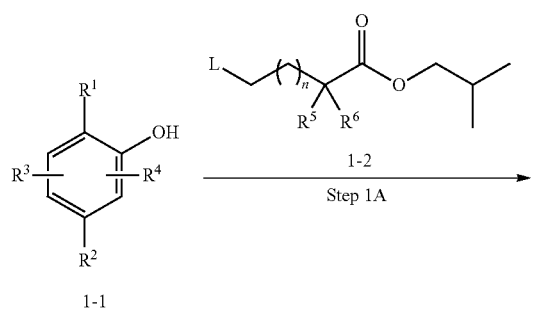

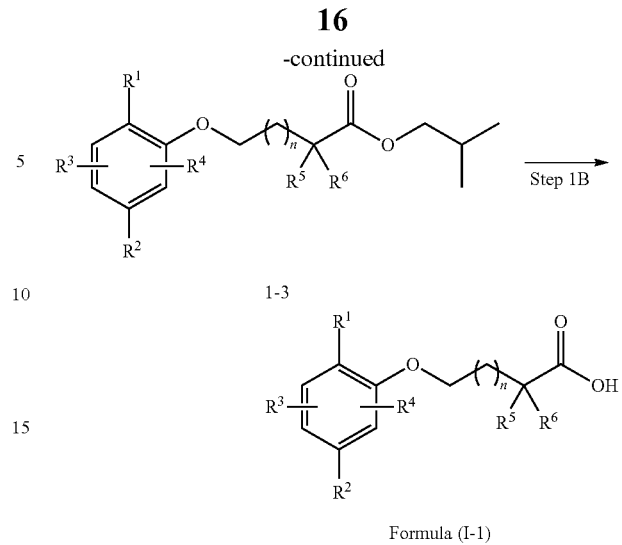

Formula (I-1)

In the above formula, L is halogen (e.g., —F, —Cl, —Br or —I); preferably, L is —Cl. Other symbols are as defined in the first aspect or the second aspect.

Step 1A

In this step, Compound 1-1 is subjected to etherification reaction with Compound 1-2 to obtain Compound 1-3.

In certain embodiments, Williamson synthesis is used. In some embodiments, the etherification reaction is carried out in an aprotic polar solvent (e.g., DMF, DMSO, etc.) in the presence of a Lewis base (e.g., $Na_2CO_3$, $K_2CO_3$, etc.). If necessary, the reaction can be carried out in the presence of a phase transfer catalyst such as TBAI (tetrabutylammonium iodide).

Step 1B

In this step, Compound 1-3 is hydrolyzed in a solvent to prepare an acid compound of Formula (I-1).

The hydrolysis can be carried out by conventional techniques. In a typical process, the hydrolysis is carried out under alkaline conditions, such as in the presence of sodium hydroxide, potassium hydroxide or lithium hydroxide. Suitable solvent includes, for example, alcohol, such as methanol, ethanol, propanol, butanol, 2-methoxyethanol, and ethylene glycol; ether, such as tetrahydrofuran (THF), 1,2-dimethoxyethane (DME) and 1,4-dioxane; amide, such as N,N-dimethylformamide (DMF) and hexamethylphosphoric triamide (phospholictriamide); and sulfoxide, such as dimethyl sulfoxide (DMSO).

The hydrolysis can also be carried out under acidic conditions, for example, in the presence of the following reagents: hydrogen halide, such as hydrogen chloride and hydrogen bromide; sulfonic acid, such as p-toluenesulfonic acid and benzenesulfonic acid; pyridinium p-toluenesulfonate; and carboxylic acid, such as acetic acid and trifluoroacetic acid. Suitable solvent includes, for example, alcohol, such as methanol, ethanol, propanol, butanol, 2-methoxyethanol, and ethylene glycol; ether, such as tetrahydrofuran (THF), 1,2-dimethoxyethane (DME) and 1,4-dioxane; amide, such as N,N-dimethylformamide (DMF) and hexamethylphosphoric triamide; and sulfoxide, such as dimethyl sulfoxide (DMSO).

Scheme 2:

This scheme illustrates the preparation of a compound of Formula (I-2), in which $R^7$ represents —CN.

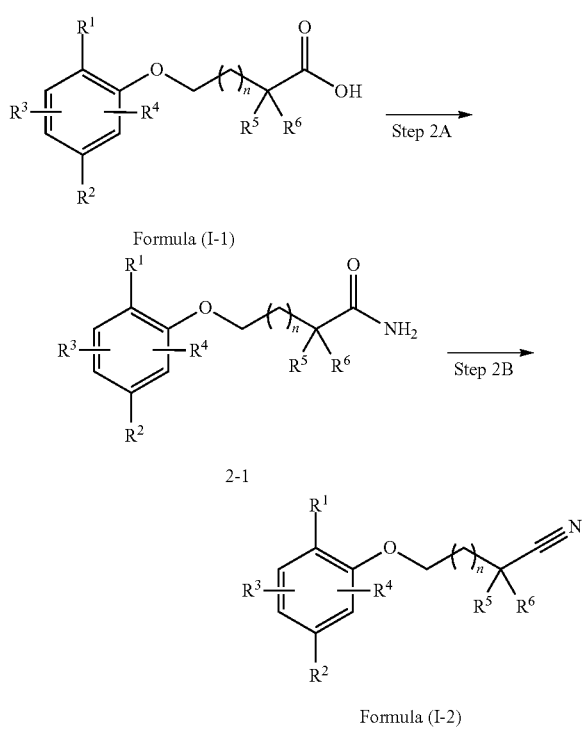

Formula (I-1)

2-1

Formula (I-2)

Step 2A (Amidation Reaction)

In this step, in the presence or absence of a coupling agent, in an inert solvent, an amide Compound 2-1 can be prepared by performing the coupling reaction of the compound of Formula I-1 prepared as described in Step 1B of Scheme 1 with an amine. If necessary, the reaction can be carried out with or without an additive, such as 1-hydroxybenzotriazole or 1-hydroxyazabenzotriazole.

The reaction is normally and preferably carried out in a solvent. There is no particular limitation on the properties of the solvent used, as long as it has no adverse effect on the reaction or the reagents involved, and can dissolve the reagent at least to a certain extent. Examples of suitable solvent include: acetone, nitromethane, DMF, sulfolane, DMSO, NMP, 2-butanone, acetonitrile; halogenated hydrocarbon such as dichloromethane, dichloroethane, chloroform; and ether such as tetrahydrofuran and dioxane.

The reaction can be carried out at a wide range of temperature, and the precise reaction temperature is not the key to the present invention. The preferred reaction temperature will depend on factors such as solvent properties and raw materials or reagents used.

Suitable coupling agents are those typically used in peptide synthesis, including, for example, diimine (e.g., dicyclohexylcarbodiimide (DCC), water-soluble carbodiimide (WSC)), 2-ethoxy-N-ethoxycarbonyl-1,2-dihydroquinoline, 2-bromo-1-ethylpyridinium tetrafluoroborate (BEP), 2-chloro-1,3-dimethylimidazolium chloride, benzotriazol-1-yloxy-tris(dimethylamino) phosphonium hexafluorophosphate (BOP), diethyl azodicarboxylate-triphenylphosphine, diethyl cyanophosphate, diethyl phosphoryl azide, 2-chloro-1-methylpyridinium iodide, N,N'-carbonyldiimidazole, benzotriazol-1-yl diethyl phosphate, ethyl chloroformate or isobutyl chloroformate. If necessary, the reaction can be carried out in the presence of a base such as N,N-diisopropylethylamine, N-methylmorpholine and triethylamine.

In addition, the amide Compound 2-1 can be produced via an acyl halide, which can be obtained by reaction with a halogenating agent, such as oxalyl chloride, phosphoryl chloride, and thionyl chloride. The resulting acyl halide can be converted into the corresponding amide compound by treating the resulting acyl halide with an amine under similar conditions as described in this step.

Step 2B

In this step, the amide group of the amide Compound 2-1 is converted into a cyano group in an inert solvent to prepare a compound of Formula I-2.

This step can be a transition metal catalyzed cyanation reaction. The transition metal catalyst may be a metal palladium catalyst, such as palladium acetate ($Pd(OAc)_2$). For example, under the protection of an inert gas (e.g., argon), the cyanation reaction occurs in a $Pd(OAc)_2$/Selectfluor catalytic system and acetonitrile to obtain a compound of Formula I-2. Acetonitrile acts as both solvent and cyano reagent.

In addition, this step may also be a dehydration reaction. For example, in the presence of a dehydrating agent, the dehydration reaction occurs in an inert solvent to obtain a compound of Formula I-2. The dehydrating agent may be thionyl chloride, phosphorus pentoxide, cyanuric chloride, trifluoroacetic anhydride, phosphorus oxychloride, phosphorus pentachloride and the like.

Scheme 3:

This scheme illustrates the preparation of a compound of Formula (I-3), wherein $R^7$ represents —C(O)X, and X is $C_1$-$C_4$ alkoxy.

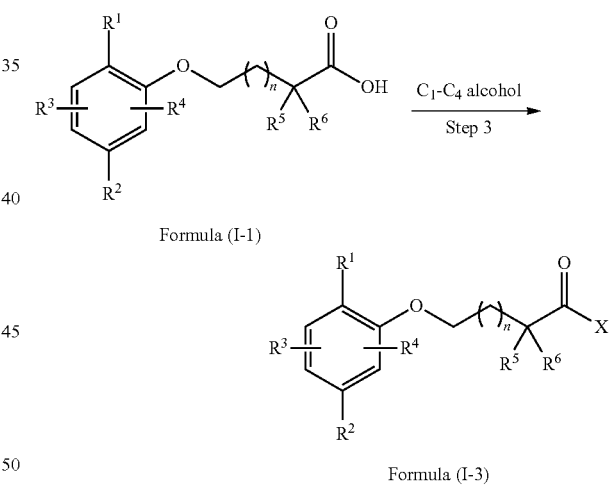

Formula (I-1)

Formula (I-3)

In this step, the esterification reaction of an acid compound of Formula I-1 and a $C_1$-$C_4$ alcohol is carried out in the presence of a catalyst in an inert solvent to prepare an ester compound of Formula I-3.

In addition, the ester compound of Formula I-3 can be generated via an acyl halide, and the later can be obtained by reaction with a halogenating agent. When resulting acyl halide is treated with an alcohol under similar conditions as described in this step, it can be converted into a corresponding ester compound.

Uses and Methods

In the fourth aspect, the present invention relates to a use of the compound, its pharmaceutically acceptable salt or ester, prodrug, stereoisomer, hydrate, solvate or crystal form, or metabolite form thereof, or any combination or mixture thereof, or the pharmaceutical composition according to the second aspect or the third aspect, for reducing body weight, reducing body fat, reducing liver fat fraction, preventing or treating obesity, and/or preventing or treating a non-alcoholic fatty liver disease (NAFLD) in a subject, or a use in manufacture of a medicament for reducing body weight, reducing body fat, reducing liver fat fraction, preventing or treating obesity, and/or preventing or treating a non-alcoholic fatty liver disease (NAFLD) (e.g., simple fatty liver or non-alcoholic steatohepatitis (NASH)) in a subject; wherein the compound is as defined in the second or third aspect.

In certain embodiments, the compound has a structure represented by Formula (I):

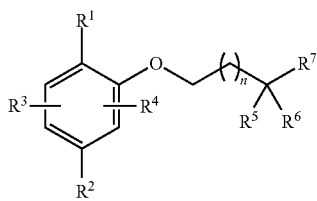

Formula (I)

wherein,
$R^1$ and $R^2$ are each independently selected from the group consisting of $C_1$-$C_4$ alkyl and $C_1$-$C_4$ alkoxy, and the $C_1$-$C_4$ alkyl or $C_1$-$C_4$ alkoxy is optionally substituted with one or several (e.g., 1, 2, 3 or 4) substituents independently selected from the group consisting of: halogen (e.g., —F, —Cl, —Br or —I), nitro, amino, hydroxyl and thiol;
$R^3$ and $R^4$ are each independently selected from the group consisting of hydrogen, halogen (e.g., —F, —Cl, —Br or —I), nitro, amino, hydroxyl, thiol, $C_1$-$C_4$ alkyl, $C_1$-$C_4$ alkoxy, $C_1$-$C_4$ alkylthio and $C_1$-$C_4$ alkylamino; wherein the amino, hydroxyl, thiol, $C_1$-$C_4$ alkyl, $C_1$-$C_4$ alkoxy, $C_1$-$C_4$ alkylthio or $C_1$-$C_4$ alkylamino is optionally substituted with one or several (e.g., 1, 2, 3 or 4) substituents independently selected from the group consisting of: halogen (e.g., —F, —Cl, —Br or —I), amino and hydroxyl;
wherein, at least one of $R^3$ and $R^4$ is halogen;
$R^5$ and $R^6$ are each independently selected from the group consisting of $C_1$-$C_4$ alkyl;
$R^7$ is selected from the group consisting of —C(O)X and cyano; wherein X is hydroxyl or $C_1$-$C_4$ alkoxy;
n is 1, 2, 3 or 4.

In certain embodiments, the compound has a structure represented by Formula (Ia):

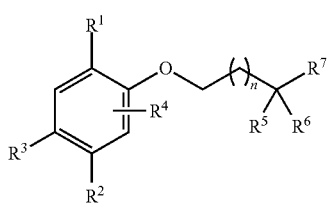

Formula (Ia)

wherein,
$R^3$ is halogen (e.g., —F, —Cl, —Br or —I);
$R^1$, $R^2$, $R^4$, $R^5$, $R^6$, $R^7$ and n are as defined in Formula (I).
In certain embodiments, $R^1$ and $R^2$ are each independently selected from the group consisting of $C_1$-$C_4$ alkyl and $C_1$-$C_4$ alkoxy, and the $C_1$-$C_4$ alkyl or $C_1$-$C_4$ alkoxy is optionally substituted with one or several (e.g., 1, 2, 3 or 4) substituents independently selected from the group consisting of: halogen (e.g., —F, —Cl, —Br, or —I) and hydroxyl.

In certain embodiments, $R^1$ and $R^2$ are each independently selected from the group consisting of methyl, ethyl, methoxy and ethoxy, and the methyl, ethyl, methoxy or ethoxy is optionally substituted with one or several (e.g., 1, 2, 3 or 4) substituents independently selected from the group consisting of: —F, —Cl, —Br, —I and hydroxyl.

In certain embodiments, $R^1$ and $R^2$ are each independently selected from the group consisting of methyl, hydroxy-substituted methyl, ethyl and methoxy.

In certain embodiments, $R^4$ is selected from the group consisting of hydrogen, halogen (e.g., —F, —Cl, —Br, or —I) and hydroxyl. In certain embodiments, $R^4$ is selected from hydrogen or hydroxyl.

In certain embodiments, $R^5$ and $R^6$ are the same as each other. In certain embodiments, $R^5$ and $R^6$ are methyl.

In certain embodiments, $R^7$ is selected from the group consisting of carboxy, —CO$_2$Me, —CO$_2$Et and cyano.

In certain embodiments, n is 1, 2 or 3.

In certain embodiments, the compound has a structure represented by Formula (Ia), wherein:
$R^1$ and $R^2$ are each independently selected from the group consisting of methyl, ethyl, methoxy and ethoxy, and the methyl, ethyl, methoxy or ethoxy is optionally substituted with one or several (e.g., 1, 2, 3 or 4) substituents independently selected from the group consisting of: —F, —Cl, —Br, —I and hydroxyl; preferably, $R^1$ and $R^2$ are each independently selected from the group consisting of methyl, hydroxyl-substituted methyl, ethyl and methoxy;
$R^3$ is —F, —Cl, —Br or —I;
$R^4$ is selected from the group consisting of hydrogen, halogen (e.g., —F, —Cl, —Br or —I), and hydroxyl; preferably, $R^4$ is selected from the group consisting of hydrogen and hydroxyl;
$R^5$ and $R^6$ are methyl;
$R^7$ is selected from the group consisting of carboxy, —CO$_2$Me, —CO$_2$Et and cyano;
n is 1, 2 or 3.

In certain embodiments, the compound is selected from:
5-(4-chloro-2,5-dimethylphenoxy)-2,2-dimethylpentanoic acid (BJMU-1);
5-(4-bromo-2,5-dimethylphenoxy)-2,2-dimethylpentanoic acid (BJMU-2);
5-(4-fluoro-2,5-dimethylphenoxy)-2,2-dimethylpentanoic acid (BJMU-3);
5-(4-bromo-2-hydroxy-3,6-dimethylphenoxy)-2,2-dimethylpentanoic acid (BJMU-415);
5-(4-bromo-2-(hydroxymethyl)-5-methylphenoxy)-2,2-dimethylpentanoic acid (BJMU-502).

In another aspect, the present invention provides a method for reducing body weight, reducing body fat, reducing liver fat fraction, preventing or treating obesity, and/or preventing or treating a non-alcoholic fatty liver disease (NAFLD) in a subject, the method comprises administering to a subject in need thereof an effective amount of a compound, its pharmaceutically acceptable salt or ester, prodrug, stereoisomer, hydrate, solvate or crystal form, or metabolite form thereof, or any combination or mixture thereof, or the pharmaceutical composition according to the third aspect; wherein the compound is as defined in the fourth aspect.

In certain embodiments, the non-alcoholic fatty liver disease (NAFLD) comprises a simple fatty liver or a non-alcoholic steatohepatitis (NASH).

In certain embodiments, the subject has a metabolic disease, and/or the subject has a condition associated with a metabolic disease (e.g., overweight, excessive body fat, and/or elevated liver fat fraction).

In the fifth aspect, the present invention provides a use of a compound, its pharmaceutically acceptable salt or ester, prodrug, stereoisomer, hydrate, solvate or crystal form, or metabolite form thereof, or any combination or mixture thereof, or the pharmaceutical composition of the second aspect or the third aspect, for reducing blood glucose level, increasing insulin sensitivity, preventing or treating insulin resistance, and/or preventing or treating diabetes mellitus (e.g., type 2 diabetes mellitus) in a subject, or in manufacture of a medicament for lowering blood glucose level, increasing insulin sensitivity, preventing or treating insulin resistance, and/or preventing or treating diabetes mellitus (e.g., type 2 diabetes mellitus) in a subject; wherein the compound is as defined in the second aspect or third aspect.

In certain embodiments, the compound has a structure represented by Formula (I),

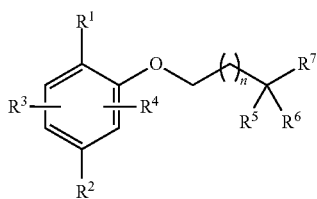

Formula (I)

wherein,
$R^1$ and $R^2$ are each independently selected from the group consisting of $C_1$-$C_4$ alkyl and $C_1$-$C_4$ alkoxy, and the $C_1$-$C_4$ alkyl or $C_1$-$C_4$ alkoxy is optionally substituted with one or several (e.g., 1, 2, 3 or 4) substituents independently selected from the group consisting of: halogen (e.g., —F, —Cl, —Br or —I), nitro, amino, hydroxyl and thiol;
$R^3$ and $R^4$ are each independently selected from the group consisting of hydrogen, halogen (e.g., —F, —Cl, —Br or —I), nitro, amino, hydroxyl, thiol, $C_1$-$C_4$ alkyl, $C_1$-$C_4$ alkoxy, $C_1$-$C_4$ alkylthio and $C_1$-$C_4$ alkylamino; wherein the amino, hydroxyl, thiol, $C_1$-$C_4$ alkyl, $C_1$-$C_4$ alkoxy, $C_1$-$C_4$ alkylthio or $C_1$-$C_4$ alkylamino is optionally substituted with one or several (e.g., 1, 2, 3 or 4) substituents independently selected from the group consisting of: halogen (e.g., —F, —Cl, —Br or —I), amino and hydroxyl;
wherein, at least one of $R^3$ and $R^4$ is halogen;
$R^5$ and $R^6$ are each independently selected from the group consisting of $C_1$-$C_4$ alkyl;
$R^7$ is selected from the group consisting of —C(O)X and cyano; wherein X is hydroxyl or $C_1$-$C_4$ alkoxy;
n is 1, 2, 3 or 4.

In certain embodiments, $R^1$ and $R^2$ are each independently selected from the group consisting of $C_1$-$C_4$ alkyl and $C_1$-$C_4$ alkoxy, and the $C_1$-$C_4$ alkyl or $C_1$-$C_4$ alkoxy is optionally substituted with one or several (e.g., 1, 2, 3 or 4) substituents independently selected from the group consisting of: halogen (e.g., —F, —Cl, —Br, or —I) and hydroxyl.

In certain embodiments, $R^1$ and $R^2$ are each independently selected from the group consisting of methyl, ethyl, methoxy and ethoxy, and the methyl, ethyl, methoxy or ethoxy is optionally substituted with one or several (e.g., 1, 2, 3 or 4) substituents independently selected from the group consisting of: —F, —Cl, —Br, —I and hydroxyl.

In certain embodiments, $R^1$ and $R^2$ are each independently selected from the group consisting of methyl, hydroxy-substituted methyl, ethyl and methoxy.

In certain embodiments, $R^3$ and $R^4$ are independently selected from the group consisting of hydrogen, halogen (e.g., —F, —Cl, —Br or —I), nitro and hydroxyl.

In certain embodiments, $R^5$ and $R^6$ are the same as each other. In certain embodiments, $R^5$ and $R^6$ are methyl.

In certain embodiments, $R^7$ is selected from the group consisting of carboxy, —CO$_2$Me, —CO$_2$Et and cyano.

In certain embodiments, n is 1, 2 or 3.

In certain embodiments, the compound has the following characteristics:
$R^1$ and $R^2$ are each independently selected from the group consisting of methyl, ethyl, methoxy and ethoxy, and the methyl, ethyl, methoxy or ethoxy is optionally substituted with one or several (e.g., 1, 2, 3 or 4) substituents independently selected from the group consisting of: —F, —Cl, —Br, —I and hydroxyl; preferably, $R^1$ and $R^2$ are each independently selected from the group consisting of methyl, hydroxyl-substituted methyl, ethyl and methoxy;
$R^3$ and $R^4$ are independently selected from the group consisting of hydrogen, halogen (e.g., —F, —Cl, —Br or —I), nitro and hydroxyl; and at least one of $R^3$ and $R^4$ is halogen;
$R^5$ and $R^6$ are methyl;
$R^7$ is selected from the group consisting of carboxy, —CO$_2$Me, —CO$_2$Et and cyano;
n is 2, 3, or 4.

In certain embodiments, the compound is selected from:
5-(4-chloro-2,5-dimethylphenoxy)-2,2-dimethylpentanoic acid (BJMU-1);
5-(4-bromo-2,5-dimethylphenoxy)-2,2-dimethylpentanoic acid (BJMU-2);
5-(4-fluoro-2,5-dimethylphenoxy)-2,2-dimethylpentanoic acid (BJMU-3);
5-(2,4-dibromo-3,6-dimethylphenoxy)-2,2-dimethylpentanoic acid (BJMU-109);
5-(3-fluoro-2,5-dimethylphenoxy)-2,2-dimethylpentanoic acid (BJMU-213);
5-(2-bromo-3,6-dimethylphenoxy)-2,2-dimethylpentanoic acid (BJMU-404);
5-(4-bromo-2-methoxy-5-methylphenoxy)-2,2-dimethylpentanoic acid (BJMU-412);
5-(4-bromo-2-hydroxy-3,6-dimethylphenoxy)-2,2-dimethylpentanoic acid (BJMU-415);
5-(4-bromo-2-(hydroxymethyl)-5-methylphenoxy)-2,2-dimethylpentanoic acid (BJMU-502);
5-(4-bromo-2,5-dimethylphenoxy)-2,2-dimethylvaleronitrile (BJMU-309).

In another aspect, the present invention provides a method for reducing blood glucose level, increasing insulin sensitivity, preventing or treating insulin resistance, and/or preventing or treating diabetes mellitus (e.g., type 2 diabetes mellitus) in a subject, the method comprises administering an effective amount of a compound, its pharmaceutically acceptable salt or ester, prodrug, stereoisomer, hydrate, solvate or crystal form, or metabolite form thereof, or any combination or mixture thereof to a subject in need thereof, wherein the compound is as defined in the fifth aspect; or, the method comprises administering an effective amount of the pharmaceutical composition of the third aspect to a subject in need thereof.

In certain embodiments, the subject has a metabolic disease, and/or the subject has a condition associated with a metabolic disease (e.g., elevated blood glucose level, insulin resistance, hyperinsulinemia, and/or impaired glucose tolerance).

In the sixth aspect, the present invention provides a use of a compound, its pharmaceutically acceptable salt or ester, prodrug, stereoisomer, hydrate, solvate or crystal form, or metabolite form thereof, or any combination or mixture thereof, or the pharmaceutical composition of the second aspect or the third aspect, for reducing blood total cholesterol level, reducing blood triglyceride level, reducing blood low density lipoprotein level and/or increasing blood high density lipoprotein level in a subject, or in manufacture of a medicament for reducing blood total cholesterol level, lowering blood triglyceride level, lowering blood low-density lipoprotein level and/or increasing blood high-density lipoprotein level in a subject; wherein, the compound is as defined in the second aspect or third aspect.

In certain embodiments, the compound has a structure represented by Formula (I):

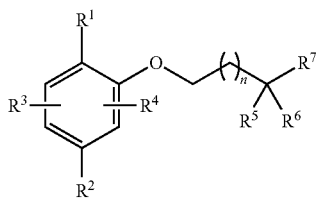

Formula (I)

wherein,
$R^1$ and $R^2$ are each independently selected from the group consisting of $C_1$-$C_4$ alkyl and $C_1$-$C_4$ alkoxy, and the $C_1$-$C_4$ alkyl or $C_1$-$C_4$ alkoxy is optionally substituted with one or several (e.g., 1, 2, 3 or 4) substituents independently selected from the group consisting of: halogen (e.g., —F, —Cl, —Br or —I), nitro, amino, hydroxyl and thiol;

$R^3$ and $R^4$ are each independently selected from the group consisting of hydrogen, halogen (e.g., —F, —Cl, —Br or —I), nitro, amino, hydroxyl, thiol, $C_1$-$C_4$ alkyl, $C_1$-$C_4$ alkoxy, $C_1$-$C_4$ alkylthio and $C_1$-$C_4$ alkylamino; wherein the amino, hydroxyl, thiol, $C_1$-$C_4$ alkyl, $C_1$-$C_4$ alkoxy, $C_1$-$C_4$ alkylthio or $C_1$-$C_4$ alkylamino is optionally substituted with one or several (e.g., 1, 2, 3 or 4) substituents independently selected from the group consisting of: halogen (e.g., —F, —Cl, —Br or —I), amino and hydroxyl;

wherein, at least one of $R^3$ and $R^4$ is halogen;

$R^5$ and $R^6$ are each independently selected from the group consisting of $C_1$-$C_4$ alkyl;

$R^7$ is selected from the group consisting of —C(O)X and cyano; wherein X is hydroxyl or $C_1$-$C_4$ alkoxy;

n is 1, 2, 3 or 4.

In certain embodiments, the compound has a structure represented by Formula (Ia):

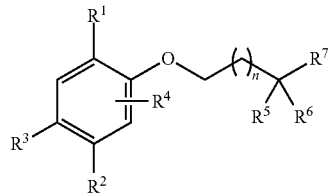

Formula (Ia)

wherein,
$R^3$ is halogen (e.g., —F, —Cl, —Br or —I);
$R^1$, $R^2$, $R^4$, $R^5$, $R^6$, $R^7$ and n are as defined above.

In certain embodiments, $R^1$ and $R^2$ are each independently selected from the group consisting of methyl, ethyl, methoxy and ethoxy, and the methyl, ethyl, methoxy or ethoxy is optionally substituted with one or several (e.g., 1, 2, 3 or 4) substituents independently selected from the group consisting of: —F, —Cl, —Br, —I and hydroxyl.

In certain embodiments, $R^1$ and $R^2$ are each independently selected from the group consisting of methyl, hydroxy-substituted methyl, ethyl and methoxy.

In certain embodiments, $R^5$ and $R^6$ are the same as each other. In certain embodiments, $R^5$ and $R^6$ are methyl.

In certain embodiments, $R^7$ is selected from the group consisting of carboxy, —$CO_2$Me, —$CO_2$Et and cyano.

In certain embodiments, n is 1, 2 or 3.

In certain embodiments, wherein,
$R^1$ and $R^2$ are each independently selected from the group consisting of methyl, ethyl, methoxy and ethoxy, and the methyl, ethyl, methoxy or ethoxy is optionally substituted with one or several (e.g., 1, 2, 3 or 4) substituents independently selected from the group consisting of: —F, —Cl, —Br, —I, hydroxyl; preferably, $R^1$ and $R^2$ are each independently selected from the group consisting of methyl, hydroxyl-substituted methyl, ethyl and methoxy;

$R^3$ is halogen (e.g., —F, —Cl, —Br or —I);
$R^4$ is hydrogen or hydroxyl;
$R^5$ and $R^6$ are methyl;
$R^7$ is selected from the group consisting of carboxy, —$CO_2$Me, —$CO_2$Et and cyano;
n is 1, 2 or 3.

In certain embodiments, the compound is selected from:
5-(4-bromo-2,5-dimethylphenoxy)-2,2-dimethylpentanoic acid (BJMU-1);
5-(4-bromo-2,5-dimethylphenoxy)-2,2-dimethylpentanoic acid (BJMU-2);
5-(4-fluoro-2,5-dimethylphenoxy)-2,2-dimethylpentanoic acid (BJMU-3);
5-(4-bromo-2,5-dimethylphenoxy)-2,2-dimethylvaleronitrile (BJMU-309);
5-(4-bromo-2-methoxy-5-methylphenoxy)-2,2-dimethylpentanoic acid (BJMU-412);
5-(4-bromo-2-hydroxy-3,6-dimethylphenoxy)-2,2-dimethylpentanoic acid (BJMU-415);
5-(4-bromo-2-(hydroxymethyl)-5-methylphenoxy)-2,2-dimethylpentanoic acid (BJMU-502).

In another aspect, the present invention provides a method for lowering blood total cholesterol level, lowering blood triglyceride level, lowering blood low-density lipoprotein level, and/or increasing blood high-density lipoprotein level in a subject, the method comprises administering an effective amount of a compound, its pharmaceutically acceptable salt or ester, prodrug, stereoisomer, hydrate, solvate or crystal form, or metabolite form thereof, or any combination or mixture thereof, to a subject in need thereof, wherein the compound is as defined in the sixth aspect; or, the method comprises administering an effective amount of the pharmaceutical composition of the third aspect to a subject in need thereof.

In certain embodiments, the subject has a metabolic disease, and/or the subject has a condition associated with a metabolic disease (e.g., elevated blood total cholesterol level, elevated blood triglyceride level, elevated blood low-density lipoprotein level, and/or decreased blood high-density lipoprotein level).

In a seventh aspect, the present invention provides a use of a compound, its pharmaceutically acceptable salt or ester, prodrug, stereoisomer, hydrate, solvate or crystal form, or metabolite form thereof, or any combination or mixture thereof, or the pharmaceutical composition of the second aspect or the third aspect, for the prevention or treatment of a metabolic disease in a subject, or in manufacture of a medicament for the prevention or treatment of a metabolic disease in a subject; wherein the compound is as defined in the second or third aspect.

In certain embodiments, the metabolic disease is selected from the group consisting of obesity, non-alcoholic fatty liver disease (NAFLD) (e.g., simple fatty liver or non-alcoholic steatohepatitis (NASH)), metabolic syndrome, type 2 diabetes mellitus, type 1 diabetes mellitus, insulin resistance, hyperinsulinemia, glucose intolerance or impaired glucose tolerance, abnormal fasting glycemia or hyperglycemia, dyslipidemia or hyperlipidemia (e.g., hypercholesterolemia), and secondary complications of these diseases (e.g., diabetic complication such as retinopathy, neuropathy, nephropathy and delayed wound healing, or cardiovascular and cerebrovascular disease such as atherosclerosis, coronary heart disease, hypertension, and stroke).

In certain embodiments, the compound has a structure represented by Formula (I):

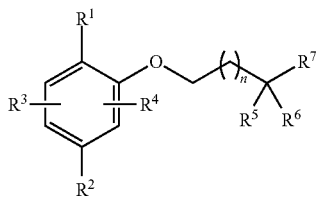

Formula (I)

wherein, $R^1$ and $R^2$ are each independently selected from the group consisting of $C_1$-$C_4$ alkyl and $C_1$-$C_4$ alkoxy, and the $C_1$-$C_4$ alkyl or $C_1$-$C_4$ alkoxy is optionally substituted with one or several (e.g., 1, 2, 3 or 4) substituents independently selected from the group consisting of: halogen (e.g., —F, —Cl, —Br or —I), nitro, amino, hydroxyl and thiol;

$R^3$ and $R^4$ are each independently selected from the group consisting of hydrogen, halogen (e.g., —F, —Cl, —Br or —I), nitro, amino, hydroxyl, thiol, $C_1$-$C_4$ alkyl, $C_1$-$C_4$ alkoxy, $C_1$-$C_4$ alkylthio and $C_1$-$C_4$ alkylamino; wherein the amino, hydroxyl, thiol, $C_1$-$C_4$ alkyl, $C_1$-$C_4$ alkoxy, $C_1$-$C_4$ alkylthio or $C_1$-$C_4$ alkylamino is optionally substituted with one or several (e.g., 1, 2, 3 or 4) substituents independently selected from the group consisting of: halogen (e.g., —F, —Cl, —Br or —I), amino and hydroxyl;

wherein, at least one of $R^3$ and $R^4$ is halogen;

$R^5$ and $R^6$ are each independently selected from the group consisting of $C_1$-$C_4$ alkyl;

$R^7$ is selected from the group consisting of —C(O)X and cyano; wherein X is hydroxyl or $C_1$-$C_4$ alkoxy;

n is 1, 2, 3 or 4.

In certain embodiments, $R^1$ and $R^2$ are each independently selected from the group consisting of $C_1$-$C_4$ alkyl and $C_1$-$C_4$ alkoxy, and the $C_1$-$C_4$ alkyl or $C_1$-$C_4$ alkoxy is optionally substituted with one or several (e.g., 1, 2, 3 or 4) substituents independently selected from the group consisting of: halogen (e.g., —F, —Cl, —Br, or —I) and hydroxyl.

In certain embodiments, $R^1$ and $R^2$ are each independently selected from the group consisting of methyl, ethyl, methoxy and ethoxy, and the methyl, ethyl, methoxy or ethoxy is optionally substituted with one or several (e.g., 1, 2, 3 or 4) substituents independently selected from the group consisting of: —F, —Cl, —Br, —I and hydroxyl.

In certain embodiments, $R^1$ and $R^2$ are each independently selected from the group consisting of methyl, hydroxy-substituted methyl, ethyl and methoxy.

In certain embodiments, $R^3$ and $R^4$ are independently selected from the group consisting of hydrogen, halogen (e.g., —F, —Cl, —Br or —I), nitro and hydroxyl.

In certain embodiments, $R^5$ and $R^6$ are the same as each other. In certain embodiments, $R^5$ and $R^6$ are methyl.

In certain embodiments, $R^7$ is selected from the group consisting of carboxy, —$CO_2$Me, —$CO_2$Et and cyano.

In certain embodiments, n is 1, 2 or 3.

The compound has a structure represented by Formula (Ia):

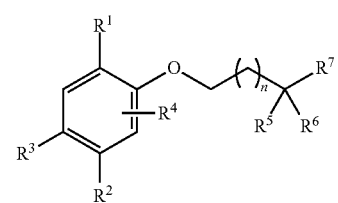

Formula (Ia)

wherein, $R^3$ is halogen (e.g., —F, —Cl, —Br or —I);

$R^1$, $R^2$, $R^4$, $R^5$, $R^6$, $R^7$ and n are as defined above.

In certain embodiments, wherein, $R^1$ and $R^2$ are each independently selected from the group consisting of methyl, ethyl, methoxy and ethoxy, and the methyl, ethyl, methoxy or ethoxy is optionally substituted with one or several (e.g., 1, 2, 3 or 4) substituents independently selected from the group consisting of: —F, —Cl, —Br, —I and hydroxyl; preferably, $R^1$ and $R^2$ are each independently selected from the group consisting of methyl, hydroxyl-substituted methyl, ethyl and methoxy;

$R^3$ and $R^4$ are independently selected from the group consisting of hydrogen, halogen (e.g., —F, —Cl, —Br or —I), nitro and hydroxyl;

$R^5$ and $R^6$ are methyl;

$R^7$ is selected from the group consisting of carboxy, —$CO_2$Me, —$CO_2$Et and cyano; and, n is 1, 2 or 3.

In certain embodiments, the compound has a structure represented by Formula (Ia), wherein $R^3$ is halogen (e.g., —F, —Cl, —Br, or —I).

In certain embodiments, the compound is selected from:
5-(4-chloro-2,5-dimethylphenoxy)-2,2-dimethylpentanoic acid (BJMU-1);
5-(4-bromo-2,5-dimethylphenoxy)-2,2-dimethylpentanoic acid (BJMU-2);
5-(4-fluoro-2,5-dimethylphenoxy)-2,2-dimethylpentanoic acid (BJMU-3);
5-(2,4-dibromo-3,6-dimethylphenoxy)-2,2-dimethylpentanoic acid (BJMU-109);
5-(2-chloro-3,6-dimethylphenoxy)-2,2-dimethylpentanoic acid (BJMU-209);
5-(3-fluoro-2,5-dimethylphenoxy)-2,2-dimethylpentanoic acid (BJMU-213);
5-(4-bromo-2,5-diethylphenoxy)-2,2-dimethylpentanoic acid (BJMU-310);
5-(4-bromo-2,3,5-trimethylphenoxy)-2,2-dimethylpentanoic acid (BJMU-315);
5-(2-bromo-3,6-dimethylphenoxy)-2,2-dimethylpentanoic acid (BJMU-404);
5-(4-bromo-2,3,6-trimethylphenoxy)-2,2-dimethylpentanoic acid (BJMU-409);
5-(4-bromo-2-iodo-3,6-dimethylphenoxy)-2,2-dimethylpentanoic acid (BJMU-413);
5-(4-bromo-2-methoxy-5-methylphenoxy)-2,2-dimethylpentanoic acid (BJMU-412);
5-(4-bromo-3,6-dimethyl-2-nitrophenoxy)-2,2-dimethylpentanoic acid (BJMU-414);
5-(4-bromo-2-hydroxy-3,6-dimethylphenoxy)-2,2-dimethylpentanoic acid (BJMU-415);
5-(4-bromo-3-hydroxy-2,5-dimethylphenoxy)-2,2-dimethylpentanoic acid (BJMU-416);
5-(4-bromo-2-(hydroxymethyl)-5-methylphenoxy)-2,2-dimethylpentanoic acid (BJMU-502);
5-(4-bromo-2,5-dimethylphenoxy)-2,2-dimethylvaleronitrile (BJMU-309);
5-(4-bromo-2,5-dimethylphenoxy)-2-ethyl-2-methylpentanoic acid (BJMU-401);
5-(2,5-dimethyl-4-nitrophenoxy)-2,2-dimethylpentanoic acid (BJMU-110);
5-(4-bromo-2-ethyl-5-methylphenoxy)-2,2-dimethylpentanoic acid (BJMU-410);
5-(4-bromo-2,5-dimethoxyphenoxy)-2,2-dimethylpentanoic acid (BJMU-201);
4-(4-bromo-2,5-dimethylphenoxy)-2,2-dimethylbutanoic acid (BJMU-111);
6-(4-bromo-2,5-dimethylphenoxy)-2,2-dimethylhexanoic acid (BJMU-403).

In another aspect, the present invention provides a method for preventing or treating a metabolic disease in a subject, the method comprises administering an effective amount of a compound, its pharmaceutically acceptable salt or ester, prodrug, stereoisomer, hydrate, solvate or crystal form, or metabolite form thereof, or any combination or mixture thereof to a subject in need thereof, and the compound is as defined in the seventh aspect; or the method comprises administering an effective amount of the pharmaceutical composition of the third aspect to a subject in need thereof.

In an eighth aspect, the present invention provides a use of a compound, its pharmaceutically acceptable salt or ester, prodrug, stereoisomer, hydrate, solvate or crystal form, or metabolite form thereof, or any combination or mixture thereof, or the pharmaceutical composition of the second aspect or the third aspect, for use as a PPARα/γ dual agonist or for the prevention and/or treatment of a disease associated with PPARα and/or PPARγ in a subject, or for manufacture of a PPARα/γ dual agonist, or for manufacture of a medicament for the prevention and/or treatment of a disease associated with PPARα and/or PPARγ in a subject; wherein, the compound is as defined in the second or third aspect.

In certain embodiments, the compound has a structure represented by Formula (I):

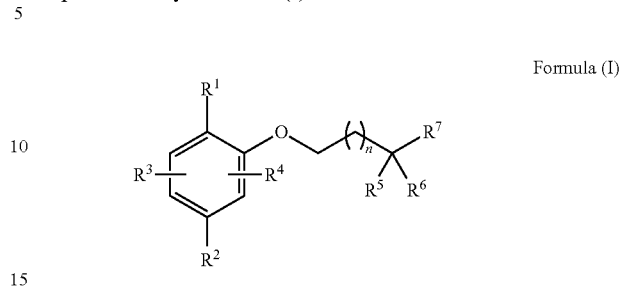

Formula (I)

wherein,
$R^1$ and $R^2$ are each independently selected from the group consisting of $C_1$-$C_4$ alkyl and $C_1$-$C_4$ alkoxy, and the $C_1$-$C_4$ alkyl or $C_1$-$C_4$ alkoxy is optionally substituted with one or several (e.g., 1, 2, 3 or 4) substituents independently selected from the group consisting of: halogen (e.g., —F, —Cl, —Br or —I), nitro, amino, hydroxyl and thiol;
$R^3$ and $R^4$ are each independently selected from the group consisting of hydrogen, halogen (e.g., —F, —Cl, —Br or —I), nitro, amino, hydroxyl, thiol, $C_1$-$C_4$ alkyl, $C_1$-$C_4$ alkoxy, $C_1$-$C_4$ alkylthio and $C_1$-$C_4$ alkylamino; wherein the amino, hydroxyl, thiol, $C_1$-$C_4$ alkyl, $C_1$-$C_4$ alkoxy, $C_1$-$C_4$ alkylthio or $C_1$-$C_4$ alkylamino is optionally substituted with one or several (e.g., 1, 2, 3 or 4) substituents independently selected from the group consisting of: halogen (e.g., —F, —Cl, —Br or —I), amino and hydroxyl;
wherein, at least one of $R^3$ and $R^4$ is halogen;
$R^5$ and $R^6$ are each independently selected from the group consisting of $C_1$-$C_4$ alkyl;
$R^7$ is selected from the group consisting of —C(O)X and cyano; wherein X is hydroxyl or $C_1$-$C_4$ alkoxy;
n is 1, 2, 3 or 4.

In certain embodiments, the compound has a structure represented by Formula (Ia):

Formula (Ia)

wherein,
$R^3$ is halogen (e.g., —F, —Cl, —Br or —I);
$R^1$, $R^2$, $R^4$, $R^5$, $R^6$, $R^7$ and n are as defined above.

In certain embodiments, $R^1$ and $R^2$ are each independently selected from the group consisting of methyl and ethyl, and the methyl or ethyl is optionally substituted with one or several (e.g., 1, 2, 3 or 4) substituents independently selected from the group consisting of: —F, —Cl, —Br, —I and hydroxyl.

In certain embodiments, $R^1$ and $R^2$ are each independently selected from the group consisting of methyl, hydroxy-substituted methyl and ethyl.

In certain embodiments, $R^3$ is —Cl or —Br.

In certain embodiments, $R^5$ and $R^6$ are the same as each other. In certain embodiments, $R^5$ and $R^6$ are methyl.

In certain embodiments, $R^7$ is selected from the group consisting of carboxy, —$CO_2Me$, —$CO_2Et$ and cyano.

In certain embodiments, n is 1, 2 or 3.

In certain embodiments, wherein, $R^1$ and $R^2$ are each independently selected from the group consisting of methyl and ethyl, and the methyl or ethyl is optionally substituted with one or several (e.g., 1, 2, 3 or 4) substituents independently selected from the group consisting of: —F, —Cl, —Br, —I and hydroxyl; preferably, $R^1$ and $R^2$ are each independently selected from the group consisting of methyl, hydroxy-substituted methyl, and ethyl;

$R^3$ is halogen; preferably, $R^3$ is —Cl or —Br;

$R^4$ is hydrogen or hydroxyl;

$R^5$ and $R^6$ are methyl;

$R^7$ is selected from the group consisting of carboxy, —$CO_2Me$, —$CO_2Et$ and cyano; and, n is 1, 2 or 3.

In certain embodiments, the compound is selected from:

5-(4-chloro-2,5-dimethylphenoxy)-2,2-dimethylpentanoic acid (BJMU-1);

5-(4-bromo-2,5-dimethylphenoxy)-2,2-dimethylpentanoic acid (BJMU-2);

5-(4-fluoro-2,5-dimethylphenoxy)-2,2-dimethylpentanoic acid (BJMU-3);

5-(4-bromo-2-hydroxy-3,6-dimethylphenoxy)-2,2-dimethylpentanoic acid (BJMU-415);

5-(4-bromo-2-(hydroxymethyl)-5-methylphenoxy)-2,2-dimethylpentanoic acid (BJMU-502);

5-(4-bromo-2,5-dimethylphenoxy)-2,2-dimethylvaleronitrile (BJMU-309).

In certain embodiments, the disease associated with PPARα and/or PPARγ is selected from the group consisting of type 2 diabetes mellitus, impaired glucose tolerance, insulin resistance syndrome, hypertension, hyperlipidemia (e.g., hypercholesterolemia), metabolic syndrome disease, visceral obesity and obesity.

In another aspect, the present invention provides a method for preventing or treating a disease associated with PPARα and/or PPARγ in a subject, the method comprises administering an effective amount of a compound, its pharmaceutically acceptable salt or ester, prodrug, stereoisomer, hydrate, solvate or crystal form, or metabolite form thereof, or any combination or mixture thereof to a subject in need thereof, and the compound is as defined in the eighth aspect; or, the method comprises administering an effective amount of the pharmaceutical composition of the third aspect to a subject in need thereof.

In the present invention, the method described in any one of the above aspects may further comprise: using the compound, its pharmaceutically acceptable salt or ester, prodrug, stereoisomer, hydrate, solvate, crystalline form, metabolite form thereof, or any combination or mixture thereof as described herein, or the pharmaceutical composition as described herein in combination with an additional pharmaceutically active agent. This additional pharmaceutically active agent can be administered before, simultaneously or after the administration of the compound, its pharmaceutically acceptable salt or ester, prodrug, stereoisomer, hydrate, solvate or crystal form, or metabolite form thereof, or any combination or mixture thereof as described herein, or the pharmaceutical composition as described herein.

In certain embodiments, the additional pharmaceutically active agent is selected from the group consisting of anti-diabetic drug, anti-obesity drug, anti-hypertensive drug, anti-atherosclerosis drug, lipid-lowering drug, anti-inflammatory drug, and anti-oxidative damage drug.

In the present invention, the method described in any one of the above aspects may also comprise: administering the compound, its pharmaceutically acceptable salt or ester, prodrug, stereoisomer, hydrate, solvate, crystalline form, metabolite form thereof, or any combination or mixture thereof as described herein, or the pharmaceutical composition as described herein in combination with an additional therapy. The additional therapy can be any therapy known for metabolic diseases, such as surgery, targeted therapy, immunotherapy, hormone therapy or gene therapy. This additional therapy can be administered before, simultaneously or after the administration of the compound, its pharmaceutically acceptable salt or ester, prodrug, stereoisomer, hydrate, solvate or crystal form, or metabolite form thereof, or any combination or mixture thereof as described herein, or the pharmaceutical composition as described herein.

In the present invention, non-limiting examples of suitable anti-diabetic drug include thiazolidinediones (e.g., rosiglitazone or pioglitazone), biguanides (e.g., metformin or phenformin), sulfonylureas (e.g., glimepiride, glibenclamide, gliclazide, chlorpropamide or glipizide), glucosidase inhibitor (e.g., acarbose or miglitol), PPAR-α agonist, PPAR-γ agonist, PPAR-α/γ dual agonist (e.g., muraglitazar), aP2 inhibitor, DPP4 inhibitor (e.g., sitagliptin or vildagliptin), insulin sensitizer, insulin or megliginides (e.g., repaglinide), etc.

Non-limiting examples of suitable anti-obesity drug include β3 adrenergic agonist (e.g., AJ9677 (Takeda/Dainippon), L750355 (Merck) or CP331648 (Pfizer)), lipase inhibitor (e.g., orlistat), 5-hydroxytryptamine (and dopamine) reuptake inhibitor (e.g., sibutramine or topiramate), thyroid receptor 13 compounds (e.g., compounds disclosed in WO99/00353 and WO00/039077), CB-1 antagonist (e.g., Rimonabant) or anorexic drug (e.g., dextroamphetamine).

Non-limiting examples of suitable lipid-lowering drug (including anti-atherosclerotic drug) include MTP inhibitor, cholesteryl ester transfer protein inhibitor (e.g., CP-529414 (Pfizer)), HMG CoA reductase inhibitor (e.g., pravastatin, lovastatin, simvastatin, atorvastatin, fluvastatin, cerivastatin or atorvastatin), squalene synthase inhibitor (e.g., α-phophonyl-sulfonate disclosed in U.S. Pat. No. 5,712,396), phenylacetic acid derivatives (e.g., fenofibrate, gemfibrozil, clofibrate, bezafibrate, ciprofibrate, clinofibrate, etc.), LDL receptor activity upregulator (e.g., MD-700 (Taisho Pharmaceutical Co. Ltd) and LY295427 (Eli Lilly)), lipoxygenase inhibitor (e.g., benzimidazole derivatives disclosed in WO97/12615, 15-LO inhibitor disclosed in WO97/12613, isothiazolones disclosed in WO96/38144), ACAT inhibitor (e.g., Avasimibe), cholesterol absorption inhibitor, ileal Na<+>/bile acid cotransporter inhibitor.

Non-limiting examples of suitable antihypertensive drug include β-adrenergic blocker, calcium channel blocker (e.g., diltiazem, verapamil, nifedipine, amlodipine), diuretic (e.g., chlorothiazide, hydrochlorothiazide, flumethiazide, hydroflumethiazide, bendroflumethiazide, methyl chlorothiazide, trichloromethiazide, polythiazide, benzthiazide, ticrynafen, chlorthalidone, fursemide, bumetanide, amiloride or spironolactone), renin inhibitor, ACE inhibitor (e.g., captopril, zofenopril, fosinopril, enalapril, cilazapril, delapril, pentopril, quinapril, ramipril or lisinopril), AT-1 receptor antagonist (e.g., losartan, irbesartan or valsartan), ET receptor antagonist (e.g., sitaxsentan or atrasentan), dual ET/AII antagonist (e.g., the compound disclosed in WO00/01389), dual NEP-ACE inhibitor (e.g., omapatrilat), and nitrates.

Non-limiting examples of suitable anti-inflammatory drug include non-steroidal anti-inflammatory drug (e.g., ibuprofen, diclofenac, naproxen, indomethacin, piroxicam, meloxicam, nabumetone, or nimesulide), steroidal anti-inflammatory drug (e.g., prednisone, dexamethasone or hydrocortisone), antibody or antagonist of inflammatory cytokine (e.g., antibody or receptor antagonist of TNFα, IL-1, IL-6, IL-8, GM-CSF or PAF), anti-inflammatory cytokine (e.g., IL-10, IL-4, IL-11, IL-13 or TGFβ), etc.

Definition of Terms

In the present invention, unless otherwise specified, the scientific and technical terms used herein have the meanings commonly understood by those skilled in the art. Moreover, the laboratory procedures involved herein are routine procedures widely used in the corresponding fields. At the same time, in order to better understand the present invention, definitions and explanations of related terms are provided below.

As used herein, the term "$C_1$-$C_4$ alkyl" refers to a group obtained by removing one hydrogen atom from a straight or branched chain alkane containing 1 to 4 carbon atoms, and specific examples thereof include but are not limited to: methyl, ethyl, propyl, n-butyl, n-pentyl, n-hexyl, isopropyl, tert-butyl or isobutyl.

As used herein, the term "halogen" includes fluorine, chlorine, bromine, and iodine.

As used herein, the term "halogenated" refers to that hydrogen(s) on a group or compound is(are) substituted with one or more halogen atoms, including perhalogenated and partially halogenated.

As used herein, the term "alkoxy" refers to a group formed in manner of alkyl-O—.

As used herein, the term "alkylamino" refers to a group formed in manner of alkyl-NH—.

As used herein, the term "alkylthio" refers to a group formed in manner of alkyl-S—.

As used herein, the term "substituted" refers to that one or multiple hydrogen atoms on a group are substituted with one or multiple substituents, and the "multiple substituents" may be same or different between each other. For example, "$C_2$ alkyl is substituted" means that one or multiple hydrogen atoms on the $C_2$ alkyl are substituted with one or multiple substituents. For example, "hydroxyl is substituted", "thiol is substituted" or "amino is substituted" respectively mean that a hydrogen atom on hydroxyl, a hydrogen atom on thiol, or hydrogen atom(s) on amino is(are) substituted with substituent(s).

As used herein, the term "pharmaceutically acceptable salt" refers to (i) a salt formed by an acidic functional group (e.g., —COOH) present in the compound provided by the present invention and an appropriate inorganic or organic cation (base), which includes, but is not limited to, alkali metal salt, such as sodium salt, potassium salt, lithium salt, etc.; alkaline earth metal salt, such as calcium salt, magnesium salt, etc.; other metal salt, such as aluminum salt, iron salt, zinc salt, copper salt, nickel salt, cobalt salt, etc.; inorganic alkali salt, such as ammonium salt; organic alkali salt, such as tert-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzyl-phenethylamine salt, piperazine salt, tetramethylammonium salt, tris(hydroxymethyl)aminomethane salt; and, (ii) a salt formed by a basic functional group (e.g., —NH$_2$) in the compound provided by the present invention and a suitable inorganic or organic anion (acid), which includes but is not limited to, hydrohalide salt, such as hydrofluoride salt, hydrochloride salt, hydrobromide salt, hydroiodide salt, etc.; inorganic acid salt, such as nitrate, perchlorate, sulfate, phosphate, etc.; lower alkane-sulfonate, such as methanesulfonate, trifluoromethanesulfonate, ethanesulfonate, etc.; arylsulfonate, such as benzenesulfonate, p-benzenesulfonate, etc.; organic acid salt, such as acetate, malate, fumarate, succinate, citrate, tartrate, oxalate, maleate, etc.; amino acid salt, such as glycinate, trimethylglycinate, arginine salt, ornithine salt, glutamate, aspartate, etc.

As used herein, the term "pharmaceutically acceptable ester" refers to an ester formed by —COOH present in the compound provided by the present invention and an appropriate alcohol, or an ester formed by —OH present in the compound provided by the present invention and an appropriate acid (e.g., a carboxylic acid or an oxygen-containing inorganic acid). Suitable ester groups include, but are not limited to, formate, acetate, propionate, butyrate, acrylate, ethylsuccinate, stearyl fatty acid ester, or palmitate. In the presence of an acid or base, the ester can undergo a hydrolysis reaction to generate the corresponding acid or alcohol.

As used herein, the term "solvate" refers to a substance formed by the association of the compound of the present invention with a solvent molecule. The solvent may be an organic solvent (e.g., methanol, ethanol, propanol, acetonitrile, etc.), for example, the compound of the present invention may form an ethanolate with ethanol. The compound of the present invention can also form an hydrate with water.

As used herein, the term "crystal form" refers to a crystal structure of a substance. When the substance is crystallized, due to various factors, the intra-molecular or intermolecular bonding mode changes, resulting in different arrangement of molecules or atoms in the lattice space, forming different crystal structures. The compound of the present invention may exist in one crystal structure or in multiple crystal structures, that is, have a "polymorphic form". The compound of the present invention may exist in different crystal forms.

As used herein, the term "stereoisomer" includes conformational isomer and configurational isomer, wherein the configurational isomer mainly includes cis-trans isomers and optical isomers. The compound of the present invention may exist in the form of stereoisomer, and therefore encompass all possible stereoisomeric forms, and any combination or any mixture thereof, for example, a single enantiomer, a single diastereomer or a mixture of the above. When the compound of the present invention comprises an alkene double bond, unless otherwise specified, it includes cis isomer and trans isomer, and any combination thereof.

As used herein, the term "prodrug" refers to a substance that can be converted into the compound of the present invention through a reaction such as oxidation, reduction, hydrolysis, etc., in a subject. The prodrug itself may or may not have the biological activity of the compound of Formula (I) (e.g., regulating glycolipid metabolism activity, anti-inflammatory activity, antioxidant activity). For example, the compound of Formula (I) comprising a hydroxyl or a carboxyl may be administered in the form of an ester, which is hydrolyzed in vivo to convert to a hydroxyl compound or a carboxyl compound. Similarly, the compound of Formula (I) comprising an amino may be acylated, alkylated or phosphorylated to form a compound such as a compound with eicosanoylamino, alanylamino or pivaloyloxymethylamino, which is then administered. For further information on the use of prodrug, see Pro-drugs as Novel Delivery Systems, Vol. 14, ACS Symposium Series (T Higuchi and W Stella), and Bioreversible Carriers in Drug Design, Pergamon Press, 1987 (ed. E B Roche, American Pharmaceutical Association). Some examples of prodrug according to the present invention include: (i) if the compound of Formula (I) contains a carboxylic acid functional group (—COOH), its ester is included, for example, hydrogen is substituted with ($C_1$-$C_8$)alkyl; (ii) if the compound of Formula (I) contains an alcohol functional group (—OH), its ether is included, for example, hydrogen is substituted with ($C_1$-$C_6$)alkanoyloxymethyl; and (iii) if the compound of Formula (I) contains a primary or secondary amino functional group (—$NH_2$ or —NHR, wherein R is not H), its amide is included, for example, one or two hydrogen atoms are substituted with ($C_1$-$C_{10}$)alkanoyl(s). In addition, certain compounds of Formula (I) can themselves serve as prodrugs of other compounds of Formula (I).

As used herein, the term "pharmaceutically acceptable carrier or excipient" refers to a carrier and/or excipient that is pharmacologically and/or physiologically compatible with the subject and the active ingredient, which is well known in the art (see, for example, Remington's Pharmaceutical Sciences. Edited by Gennaro A R, 19th ed. Pennsylvania: Mack Publishing Company, 1995), and includes, but is not limited to: disintegrant, binder, surfactant, glidant, lubricant, pH adjuster, ionic strength enhancer, agent for maintaining osmotic pressure, agent for delaying absorption, diluent, antioxidant, coloring agent, flavoring agent, preservative, taste masking agent, etc. For example, non-limiting examples of disintegrant include sodium starch glycolate, sodium carboxymethyl cellulose, calcium carboxymethyl cellulose, croscarmellose sodium, crospovidone, polyvinylpyrrolidone, methylcellulose, microcrystalline cellulose, lower alkyl-substituted hydroxypropylcellulose, starch, pregelatinized starch and sodium alginate. Non-limiting examples of binder include microcrystalline cellulose, gelatin, sugar, polyethylene glycol, natural and synthetic gums, polyvinylpyrrolidone, pregelatinized starch, hydroxypropyl cellulose, and hydroxypropyl methyl cellulose. Non-limiting examples of diluent include lactose (monohydrate, spray-dried monohydrate, anhydrous, etc.), mannitol, xylitol, glucose, sucrose, sorbitol, microcrystalline cellulose, starch, and calcium hydrogen phosphorate dihydrate. Non-limiting examples of surfactant include sodium lauryl sulfate and polysorbate 80. Non-limiting examples of glidant include silica and talc. Non-limiting examples of lubricant include magnesium stearate, calcium stearate, zinc stearate, sodium stearyl fumarate, and mixtures of magnesium stearate and sodium lauryl sulfate. Non-limiting example of pH adjusting agent includes but is not limited to phosphate buffer. Ionic strength enhancer includes, but is not limited to, sodium chloride. Agent for maintaining osmotic pressure includes but is not limited to sugar, NaCl and the like. Agent that delays absorption includes, but is not limited to, monostearate and gelatin. Preservative includes, but is not limited to, various antibacterial agents and antifungal agents, such as thimerosal, 2-phenoxyethanol, paraben, chlorobutanol, phenol, sorbic acid and the like.

As used herein, the term "prevention" refers to a method performed to prevent or delay the occurrence of a disease or disorder or symptom in a subject. As used herein, the term "treatment" refers to a method performed to obtain a beneficial or desired clinical result. For the purpose of the present invention, the beneficial or desired clinical result includes, but is not limited to, alleviating symptom, narrowing disease scope, stabilizing (i.e., not getting worse) disease state, delaying or slowing disease development, improving or alleviating disease state, and relieving symptom (whether partially or fully), whether detectable or undetectable. In addition, "treatment" may also refer to that a survival period is prolonged compared to an expected survival period (if not receiving treatment).

As used herein, the term "subject" refers to a mammal, such as a primate mammal, such as a human. In certain embodiments, the subject (e.g., a human) has a metabolic disease, and/or the subject has a condition related to a metabolic disease (e.g., (i) overweight, excessive body fat, and/or elevated liver fat fraction; (ii) elevated blood total cholesterol level, elevated blood triglyceride level, elevated blood low-density lipoprotein level, and/or decreased blood high-density lipoprotein level; (iii) elevated blood glucose level, insulin resistance, and/or impaired glucose tolerance).

As used herein, the term "effective amount" refers to an amount sufficient to obtain or at least partially obtain a desired effect. For example, an effective amount for preventing a disease (e.g., a metabolic disease or a condition related to metabolic disease) refers to an amount sufficient to prevent, stop or delay the occurrence of a disease (e.g., a metabolic disease or a condition related to metabolic disease); an effective amount for treating a disease refers to an amount sufficient to cure or at least partially prevent the disease and its complication in a patient who has already suffered from the disease. It is completely within the ability of those skilled in the art to determine such an effective amount. For example, the effective amount for therapeutic use will depend on severity of a disease to be treated, overall state of patient's own immune system, patient's general conditions such as age, weight and gender, administration manner of drug, and other treatments administered simultaneously, and so on.

The Beneficial Effects of the Present Invention

Through a lot of researches and repeated screening, the phenoxy carboxylic acid compound of the present application was obtained, and the compound can achieve at least one of the following technical effects: (1) it can significantly inhibit inflammatory signals and inflammatory responses; (2) it can significantly activate antioxidant response and enhance antioxidant ability; (3) it can significantly improve insulin resistance and lower blood glucose level; (4) it can significantly reduce body fat and blood lipid levels (e.g., blood total cholesterol level); (5) it has PPARα/γ dual agonistic activity; and (6) it has good safety; therefore, the compound of this application can be used to treat a metabolic disease (e.g., MS, NAFLD and/or diabetes mellitus) and has great clinical value.

BRIEF DESCRIPTION OF THE DRAWINGS

FIG. 8A: stained with Oil red O; FIG. 8B: stained with H.E.

FIG. 12A: stained with Oil red O; FIG. 12B: stained with H.E.

SPECIFIC MODELS FOR CARRYING OUT THE PRESENT INVENTION

Figure 1:
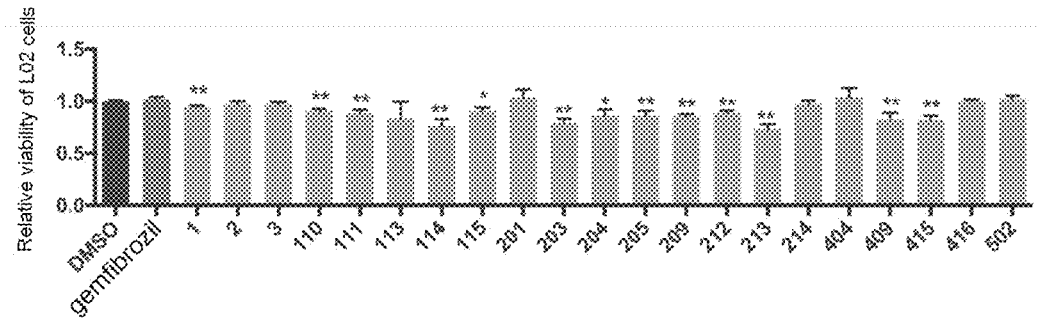
FIG. 1 shows the cytotoxicity of the compound to L02 human normal hepatocytes, and the results are expressed as the relative viability of cells in the administration group (10 μM) as compared with that of the cells of the control group (DMSO group), in which compared with the control group, *$P<0.05$, $P<0.01$, *$P<0.001$.

The embodiments of the present invention will be described in detail below in conjunction with examples, but those skilled in the art will understand that the following examples are only used to illustrate the present invention and should not be regarded as limiting the scope of the present invention.

Unless otherwise specified, the experiments and methods described in the examples are basically performed according to conventional methods well known in the art and described in various references. If specific conditions are not indicated in the examples, it shall be carried out in accordance with conventional conditions or conditions recommended by the manufacturer. The reagents or instruments used without the manufacturer's indication are all conventional products that are commercially available. Those skilled in the art know that the examples describe the present invention by way of example and are not intended to limit the scope of protection claimed by the present invention. All publications and other references mentioned in the context are incorporated in their entirety by reference.

Synthesis and Structural Characterization of Compounds

Instruments and Reagents

The measurement of MS was performed by Agilent (ESI) mass spectrometer, manufacturer: Agilent, model: Agilent 6120B High-resolution mass spectrogram was recorded by PE SCLEX QSTAR spectrometer.

Hydrogen nuclear magnetic spectrum and carbon nuclear magnetic spectrum were recorded by Bruker AVIII-400 spectrometer.

Thin-layer chromatography purification was performed by GF254 (0.4-0.5 nm) silica gel plate produced by Yantai Jiangyou silica gel development Co. Ltd.

Reaction monitoring was performed by thin-layer chromatography (TLC), and the used developing solvent systems included not limiting to: dichloromethane-methanol system, n-hexane-ethyl acetate system, and petroleum ether-ethyl acetate system, in which the volume ratio of solvents was adjusted according to the compound, while a small amount of triethylamine could be added for adjustment.

Unless specifically indicated in the examples, the reaction temperature was room temperature (20° C. to 30° C.).

The reagents used in the examples were purchased from Acros Organics, Aldrich Chemical Company or Topbiochem Ltd.

The abbreviations used herein had the following meanings:

AcCl: acetyl chloride; Ac$_2$O: acetic anhydride; DCM: dichloromethane; aq: aqueous solution; TBAI: tetrabutylammonium iodide; DMF: N,N-dimethylformamide; EtOH: ethanol.

SYNTHESIS EXAMPLES

Example 1: Preparation of 5-(4-chloro-2,5-dimethylphenoxy)-2,2-dimethylpentanoic acid (BJMU-1)

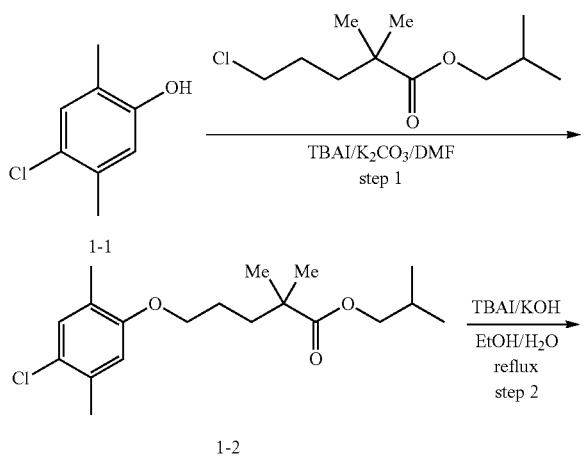

-continued

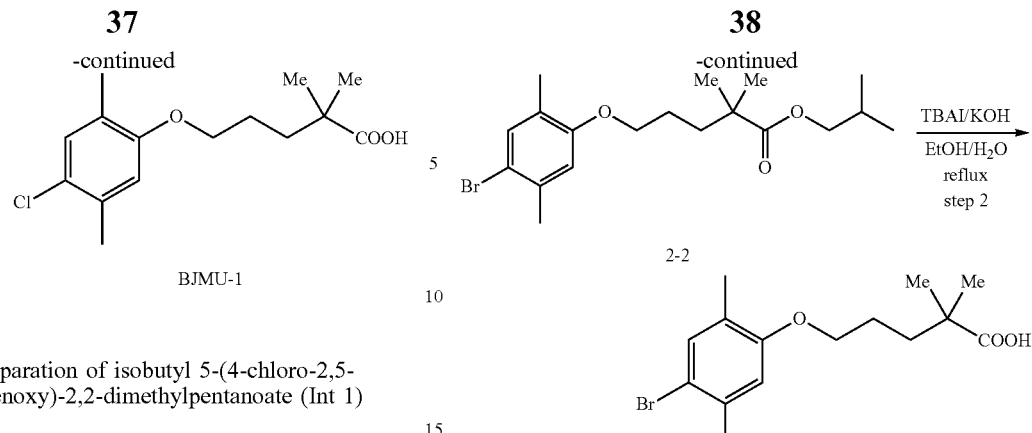

BJMU-1

BJMU-2

Step 1: Preparation of isobutyl 5-(4-chloro-2,5-dimethylphenoxy)-2,2-dimethylpentanoate (Int 1)

Compound 1-1 (4-chloro-2,5-dimethylphenol) (780 mg, 5.0 mmol), isobutyl 5-chloro-2,2-dimethylpentanoate (1144 mg, 5.2 mmol), TBAI (36.9 mg, 0.1 mmol) and potassium carbonate (1380 mg, 10.0 mmol) were dissolved in DMF (30 mL), stirred overnight at 90 degrees Celsius; when TLC monitoring indicated no trend of continuous conversion, the reaction solution was poured into water and layered; after the aqueous phase was extracted with ethyl acetate, the organic phases were combined, dried over anhydrous sodium sulfate and filtered, and the filtrate was concentrated. The crude product was separated by silica gel column chromatography to obtain Compound 1-2 (1.5 g) with a yield of 88%.

Step 2: Preparation of 5-(4-chloro-2,5-dimethylphenoxy)-2,2-dimethylpentanoic acid (BJMU-1)

Compound 1-2 (isobutyl 5-(4-chloro-2,5-dimethylphenoxy)-2,2-dimethylpentanoate) (1360 mg, 4.0 mmol), KOH (1120 mg, 20.0 mmol) and TBAI (36.9 mg, 0.1 mmol) were dissolved in a mixed solvent of EtOH (7 mL) and H$_2$O (2 mL), heated to reflux at 120° C., and reacted for 24 h; when TLC monitoring indicated the reaction was completed, water was added for washing; the system was acidified with diluted hydrochloric acid and extracted three times with ethyl acetate. The organic phases were combined, dried over anhydrous sodium sulfate and filtered, and the filtrate was concentrated. The extract was subjected to rotary evaporation to dryness and purified by column chromatography to obtain the target product BJMU-1 (1.1 g), and the yield was 96%.

$^1$H NMR (400 MHz, Chloroform-d) δ 7.07 (s, 1H), 6.62 (s, 1H), 3.90 (t, J=5.9 Hz, 2H), 2.31 (s, 3H), 2.15 (s, 3H), 1.88-1.65 (m, 4H), 1.25 (s, 6H). $^{13}$C NMR (101 MHz, CDCl$_3$) δ 185.83, 155.68, 133.80, 130.71, 126.06, 124.99, 113.64, 68.46, 42.06, 36.96, 25.21, 25.14, 20.19, 15.68.

Example 2: Preparation of 5-(4-bromo-2,5-dimethylphenoxy)-2,2-dimethylpentanoic acid (BJMU-2)

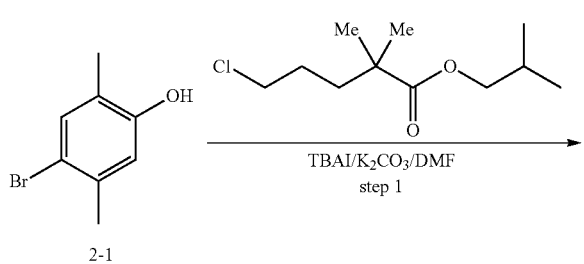

2-1

Compound BJMU-2 was synthesized by a method similar to that described in Step 1 to Step 2 of Example 1, except that in Step 1 of Example 2, Compound 1-1 in Step 1 of Example 1 was replaced with Compound 2-1, and the yield of the two steps was 66%.

$^1$H NMR (400 MHz, Chloroform-d) δ 7.25 (s, 1H), 6.64 (s, 1H), 3.90 (t, J=5.9 Hz, 2H), 2.33 (s, 3H), 2.15 (s, 3H), 1.91-1.58 (m, 4H), 1.25 (s, 6H). $^{13}$C NMR (101 MHz, CDCl3) δ 184.38, 156.20, 135.57, 133.65, 126.29, 114.58, 113.47, 68.23, 41.94, 36.78, 25.04, 24.98, 22.87, 15.44

Example 3: Preparation of 5-(4-fluoro-2,5-dimethylphenoxy)-2,2-dimethylpentanoic acid (BJMU-3)

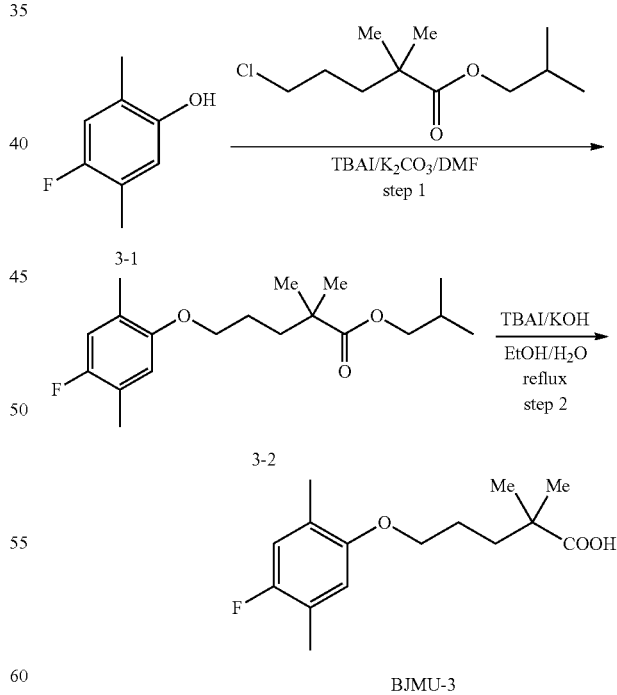

BJMU-3

Compound BJMU-3 was synthesized by a method similar to that described in Step 1 to Step 2 of Example 1, except that in Step 1 of Example 3, Compound 1-1 in Step 1 of Example 1 was replaced with Compound 3-1, and the yield of the two steps was 78%.

$^1$H NMR (400 MHz, CDCl3) δ 6.78 (d, J=9.8 Hz, 1H), δ 6.56 (d, J=7.0 Hz, 1H), δ 3.89 (t, J=6.0 Hz, 2H) δ 2.22 (s, 3H), δ 2.17 (s, 3H), δ 1.85-1.69 (m, 4H), δ 1.25 (s, 6H). $^{13}$C NMR (101 MHz, CDCl3) δ 184.76, 155.12 (d, J=236.3 Hz), 152.72 (d, J=2.15), 125.60 (d, J=7.57), 121.61 (J=18.4), 116.82 (d, J=23.74), 113.78 (d, J=5.43), 68.69, 41.94, 36.81, 25.12, 24.94, 22.83, 15.41. $^{19}$F NMR (376 MHz, CDCl3), δ−129.00 (s, 1F)

Example 4: Preparation of 5-(2,4-dibromo-3,6-dimethylphenoxy)-2,2-dimethylpentanoic acid (BJMU-109)

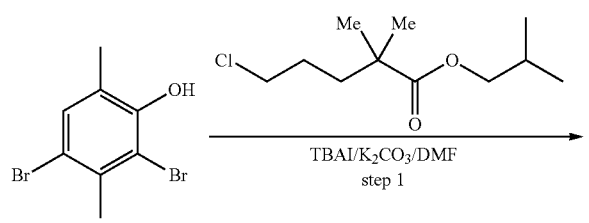

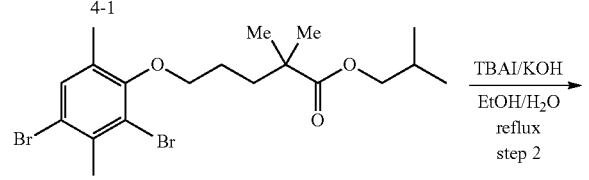

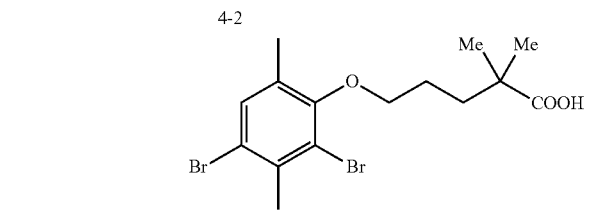

BJMU-109

Compound BJMU-109 was synthesized by a method similar to that described in Step 1 to Step 2 of Example 1, except that in Step 1 of Example 4, Compound 1-1 in Step 1 of Example 1 was replaced with Compound 4-1, and the yield of the two steps was 72%.

$^1$H NMR (400 MHz, Chloroform-d) δ 7.33 (s, 1H), 3.83 (t, J=5.6 Hz, 2H), 2.53 (s, 3H), 2.26 (s, 3H), 1.89-1.75 (m, 4H), 1.27 (s, 6H). $^{13}$C NMR (101 MHz, CDCl3) δ 184.31, 153.96, 136.07, 133.23, 131.42, 121.11, 119.16, 72.66, 41.93, 36.69, 25.76, 24.96, 23.90, 16.29

Example 5: Preparation of 5-(2-chloro-3,6-dimethylphenoxy)-2,2-dimethylpentanoic acid (BJMU-209)

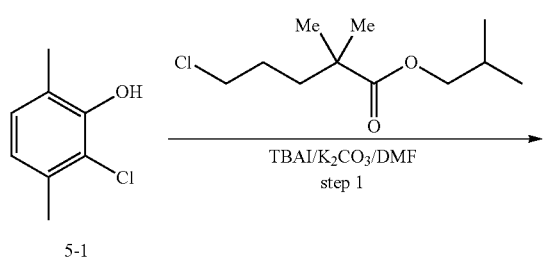

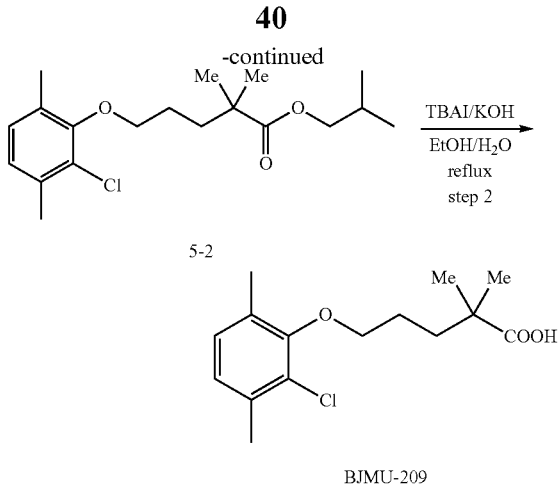

BJMU-209

Compound BJMU-209 was synthesized by a method similar to that described in Step 1 to Step 2 of Example 1, except that in Step 1 of Example 5, Compound 1-1 in Step 1 of Example 1 was replaced with Compound 5-1, and the yield of the two steps was 58%.

$^1$H NMR (400 MHz, Chloroform-d) δ 6.98 (d, J=7.7 Hz, 1H), 6.90 (d, J=7.7 Hz, 1H), 3.90 (t, J=5.7 Hz, 2H), 2.36 (s, 3H), 2.29 (s, 3H), 1.90-1.82 (m, 4H), 1.30 (s, 6H). $^{13}$C NMR (101 MHz, Chloroform-d) δ 184.6, 153.5, 135.1, 130.1, 128.4, 128.2, 125.6, 72.6, 41.9, 36.7, 25.9, 24.9, 20.1, 16.3.

Example 6: Preparation of 5-(3-fluoro-2,5-dimethylphenoxy)-2,2-dimethylpentanoic acid (BJMU-213)

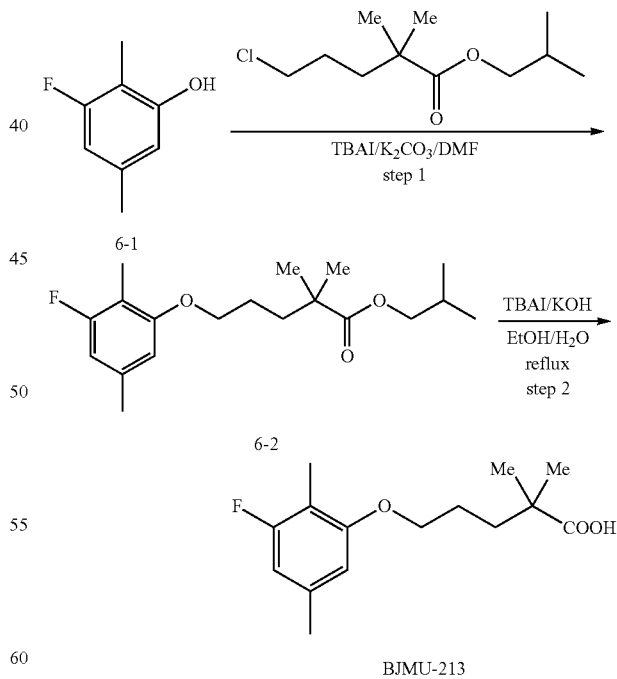

BJMU-213

Compound BJMU-213 was synthesized by a method similar to that described in Step 1 to Step 2 of Example 1, except that in Step 1 of Example 6, Compound 1-1 in Step 1 of Example 1 was replaced with Compound 6-1, and the yield of the two steps was 76%.

¹H NMR (400 MHz, Chloroform-d) δ 6.90-6.85 (m, 1H), 6.59 (s, 1H), 4.01 (t, J=5.6, 2H), 2.48 (s, 3H), 2.41 (s, 3H), 1.80-1.67 (m, 4H), 1.21 (s, 6H). ¹³C NMR (101 MHz, Chloroform-d) δ 182.28, 162.75, 157.90, 138.40, 115.43, 113.02, 111.63, 69.37, 42.41, 37.22, 25.19, 25.13, 24.43, 16.80.

Example 7: Preparation of 5-(4-bromo-2,5-diethylphenoxy)-2,2-dimethylpentanoic acid (BJMU-310)

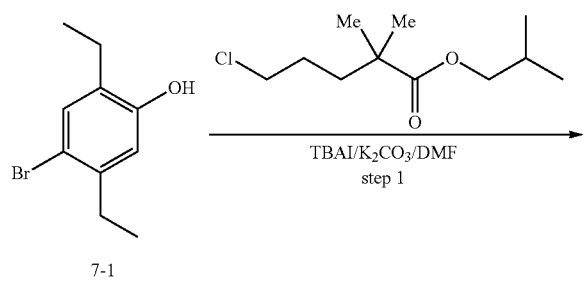

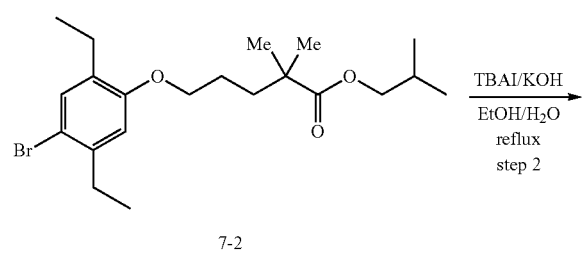

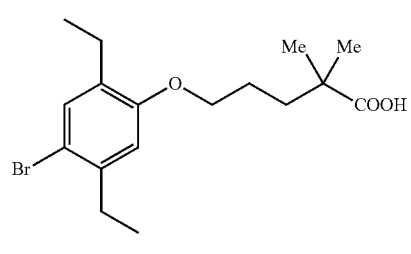

BJMU-310

Compound BJMU-310 was synthesized by a method similar to that described in Step 1 to Step 2 of Example 1, except that in Step 1 of Example 7, Compound 1-1 in Step 1 of Example 1 was replaced with Compound 7-1, and the yield of the two steps was 56%.

¹H NMR (400 MHz, Chloroform-d) δ 7.28 (s, 1H), 6.68 (s, 1H), 3.95 (t, J=5.8 Hz, 2H), 2.65 (dq, J=47.2, 7.5 Hz, 4H), 1.89-1.70 (m, 4H), 1.28 (s, 6H), 1.21 (dt, J=14.9, 7.5 Hz, 6H). ¹³C NMR (101 MHz, CDCl3) δ 184.78, 156.11, 141.24, 132.49, 132.34, 114.15, 112.23, 68.12, 41.99, 36.86, 29.73, 25.08, 22.71, 14.50.

Example 8: Preparation of 5-(4-bromo-2,3,5-trimethylphenoxy)-2,2-dimethylpentanoic acid (BJMU-315)

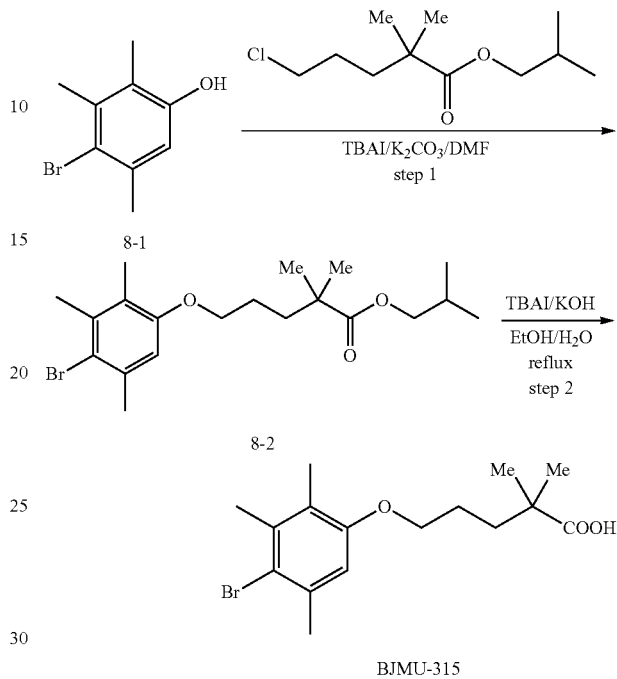

Compound BJMU-315 was synthesized by a method similar to that described in Step 1 to Step 2 of Example 1, except that in Step 1 of Example 8, Compound 1-1 in Step 1 of Example 1 was replaced with Compound 8-1, and the yield of the two steps was 68%.

¹H NMR (400 MHz, Chloroform-d) δ 6.59 (s, 1H), 3.89 (t, J=5.9 Hz, 2H), 2.38 (s, 3H), 2.37 (s, 3H), 2.18 (s, 3H), 1.87-1.69 (m, 4H), 1.25 (s, 6H). ¹³C NMR (101 MHz, Chloroform-d) δ 184.6, 155.5, 137.2, 135.5, 124.2, 119.0, 111.5, 68.5, 41.9, 36.8, 25.1, 25.0, 24.4, 20.4, 12.8.

Example 9: Preparation of 5-(2-bromo-3,6-dimethylphenoxy)-2,2-dimethylpentanoic acid (BJMU-404)

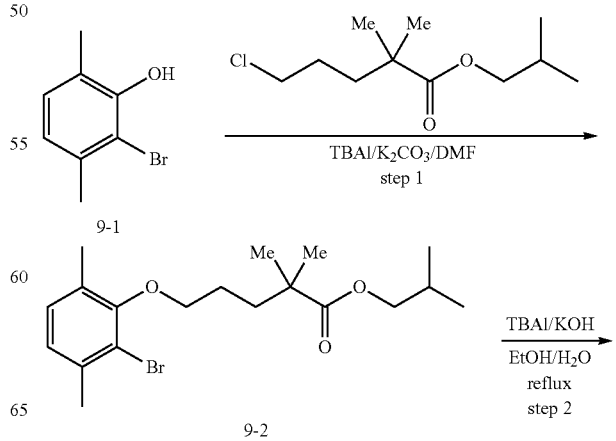

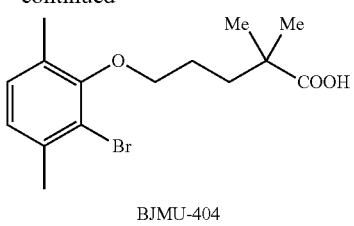

BJMU-404

Compound BJMU-404 was synthesized by a method similar to that described in Step 1 to Step 2 of Example 1, except that in Step 1 of Example 9, Compound 1-1 in Step 1 of Example 1 was replaced with Compound 9-1, and the yield of the two steps was 48%.

$^1$H NMR (400 MHz, Chloroform-d) δ 6.98 (d, J=7.7 Hz, 1H), 6.88 (d, J=7.7 Hz, 1H), 3.86 (t, J=5.7 Hz, 2H), 2.36 (s, 3H), 2.27 (s, 3H), 1.91-1.57 (m, 4H), 1.27 (s, 6H). $^{13}$C NMR (101 MHz, CDCl3) δ 184.84, 154.44, 137.09, 129.96, 129.37, 125.79, 120.24, 72.59, 42.01, 36.78, 25.85, 24.99, 23.08, 16.49.

Example 10: Preparation of 5-(4-bromo-2,3,6-trimethylphenoxy)-2,2-dimethylpentanoic acid (BJMU-409)

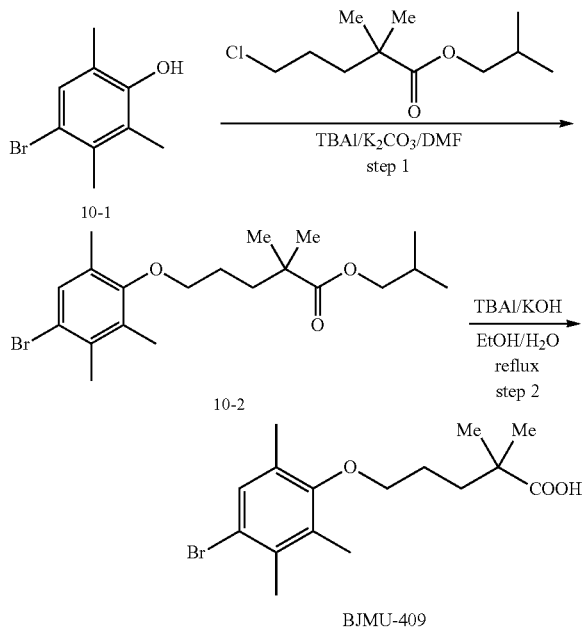

BJMU-409

Compound BJMU-409 was synthesized by a method similar to that described in Step 1 to Step 2 of Example 1, except that in Step 1 of Example 10, Compound 1-1 in Step 1 of Example 1 was replaced with Compound 10-1, and the yield of the two steps was 65%.

$^1$H NMR (400 MHz, Chloroform-d) δ 7.23 (s, 1H), 3.67 (t, J=4.8 Hz, 2H), 2.33 (s, 3H), 2.22 (m, 6H), 1.79-1.78 (m, 4H), 1.27 (s, 6H). $^{13}$C NMR (101 MHz, CDCl3) δ 183.86, 154.97, 134.85, 131.58, 131.44, 129.91, 119.61, 72.63, 41.91, 36.84, 25.87, 24.98, 19.75, 15.97, 13.82.

Example 11: Preparation of 5-(4-bromo-2-iodo-3,6-dimethylphenoxy)-2,2-dimethylpentanoic acid (BJMU-413)

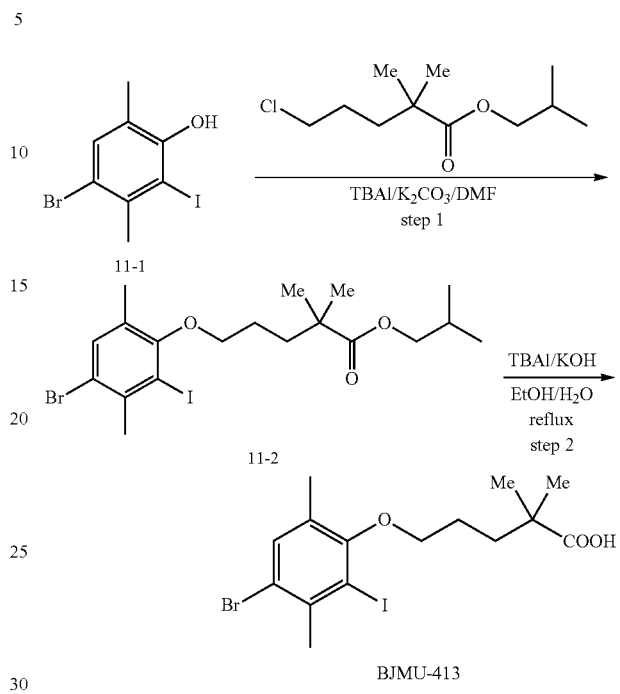

BJMU-413

Compound BJMU-413 was synthesized by a method similar to that described in Step 1 to Step 2 of Example 1, except that in Step 1 of Example 11, Compound 1-1 in Step 1 of Example 1 was replaced with Compound 11-1, and the yield of the two steps was 58%.

$^1$H NMR (400 MHz, Chloroform-d) δ 7.31 (s, 1H), 4.08 (t, J=7.1 Hz, 2H), 2.39 (s, 3H), 2.31 (s, 3H), 1.82-1.71 (m, 4H), 1.21 (s, 6H). $^{13}$C NMR (400 MHz, Chloroform-d) δ 180.57, 153.80, 134.22, 133.83, 128.46, 119.83, 91.62, 70.78, 43.22, 37.23, 25.18, 24.30, 22.50, 16.04.

Example 12: Preparation of 5-(4-bromo-2-methoxy-5-methylphenoxy)-2,2-dimethylpentanoic acid (BJMU-412)

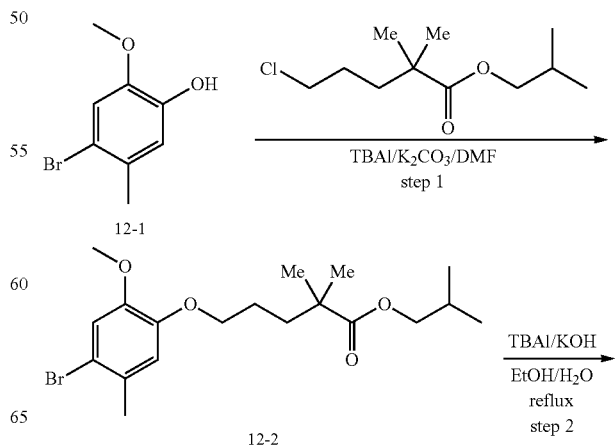

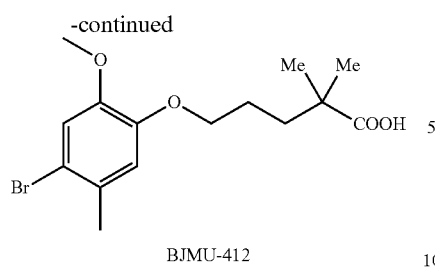

BJMU-412

Compound BJMU-412 was synthesized by a method similar to that described in Step 1 to Step 2 of Example 1, except that in Step 1 of Example 12, Compound 1-1 in Step 1 of Example 1 was replaced with Compound 12-1, and the yield of the two steps was 56%.

$^1$H NMR (400 MHz, Chloroform-d) δ 12.30 (s, 1H), 7.22 (s, 1H), 6.38 (s, 1H), 3.88-3.94 (t, J=5.8 Hz, 2H), 3.83 (s, 3H), 2.11 (s, 3H), 1.82-1.73 (m, 4H), 1.25 (s, 6H). $^{13}$C NMR (101 MHz, CDCl3) δ 185.01, 157.10, 154.53, 133.92, 120.38, 101.08, 97.35, 68.42, 56.41, 41.97, 36.74, 25.03, 24.99, 15.14.

Example 13: Preparation of 5-(4-bromo-3,6-dimethyl-2-nitrophenoxy)-2,2-dimethylpentanoic acid (BJMU-414)

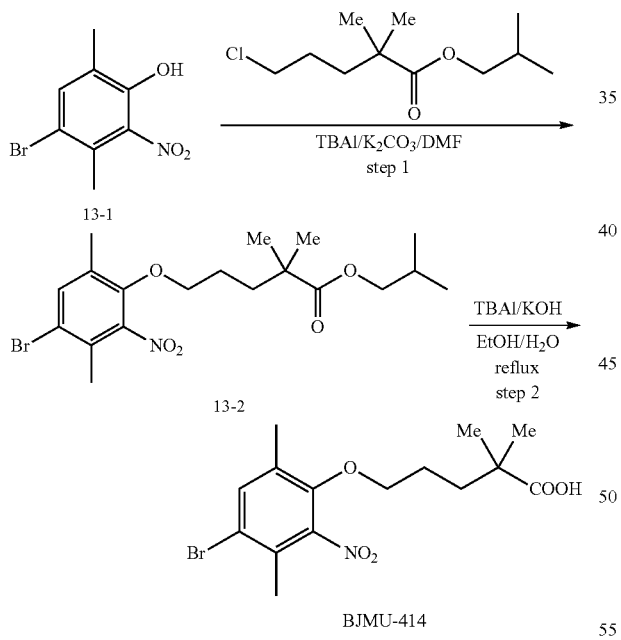

BJMU-414

Compound BJMU-414 was synthesized by a method similar to that described in Step 1 to Step 2 of Example 1, except that in Step 1 of Example 13, Compound 1-1 in Step 1 of Example 1 was replaced with Compound 13-1, and the yield of the two steps was 68%.

$^1$H NMR (400 MHz, Chloroform-d) δ 7.44 (s, 1H), 3.87 (t, J=5.8 Hz, 2H), 2.25 (s, 6H), 1.76-1.63 (m, 4H), 1.22 (s, 6H). $^{13}$C NMR (101 MHz, CDCl3) δ 184.8, 147.8, 147.4, 135.8, 132.2, 127.9, 119.3, 75.3, 41.9, 36.3, 25.6, 24.9, 17.7, 15.7.

Example 14: Preparation of 5-(4-bromo-2-hydroxy-3,6-dimethylphenoxy)-2,2-dimethylpentanoic acid (BJMU-415)

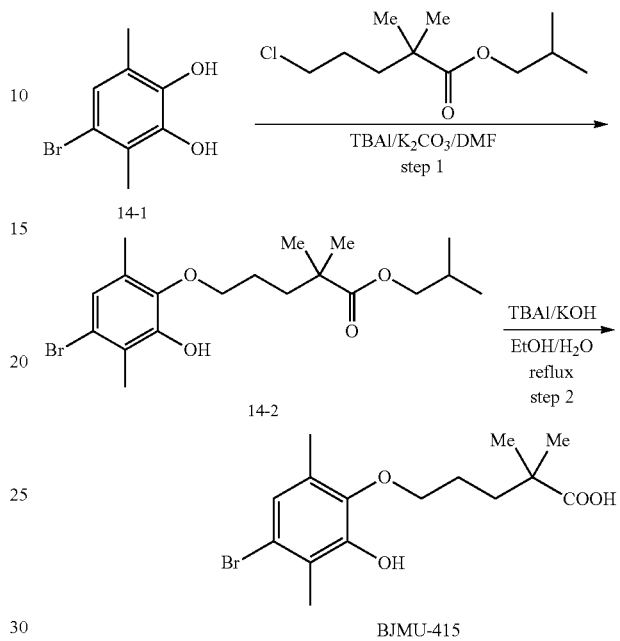

BJMU-415

Compound BJMU-415 was synthesized by a method similar to that described in Step 1 to Step 2 of Example 1, except that in Step 1 of Example 14, Compound 1-1 in Step 1 of Example 1 was replaced with Compound 14-1, and the yield of the two steps was 66%.

$^1$H NMR (400 MHz, CDCl3) δ 11.04 (brs, 1H), 6.91 (s, 1H), 5.95 (brs, 1H), 3.83 (t, J=5.9 Hz, 2H), 2.28 (s, 3H), 2.22 (s, 3H), 1.83-1.73 (m, 4H), 1.27 (s, 6H). $^{13}$C NMR (101 MHz, CDCl3) δ 183.4, 147.7, 143.4, 128.9, 124.9, 122.4, 119.9, 73.6, 41.9, 36.6, 26.1, 25.1, 15.7, 15.5.

Example 15: Preparation of 5-(4-bromo-3-hydroxy-2,5-dimethylphenoxy)-2,2-dimethylpentanoic acid (BJMU-416)

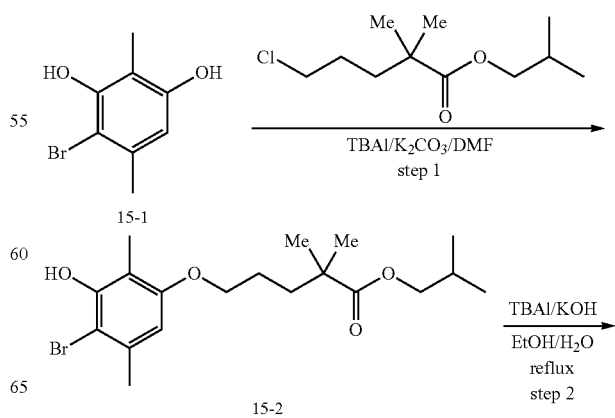

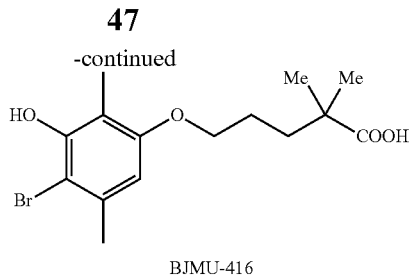

BJMU-416

Compound BJMU-416 was synthesized by a method similar to that described in Step 1 to Step 2 of Example 1, except that in Step 1 of Example 15, Compound 1-1 in Step 1 of Example 1 was replaced with Compound 15-1, and the yield of the two steps was 57%.

$^{1}$H NMR (400 Hz, CDCl3), δ: 6.34 (s, 1H), 3.90 (t, J=5.6 Hz, 2H), 2.34 (s, 3H), 2.14 (s, 3H), 1.72-1.81 (m, 4H), 1.25 (s, 6H). $^{13}$C NMR (101 Hz, CDCl3), δ: 184.7, 156.7, 150.6, 134.8, 111.2, 106.1, 104.7, 68.5, 41.9, 36.8, 25.0, 24.9, 23.2, 9.1.

Example 16: Preparation of 5-(4-bromo-2-(hydroxymethyl)-5-methylphenoxy)-2,2-dimethylpentanoic acid (BJMU-502)

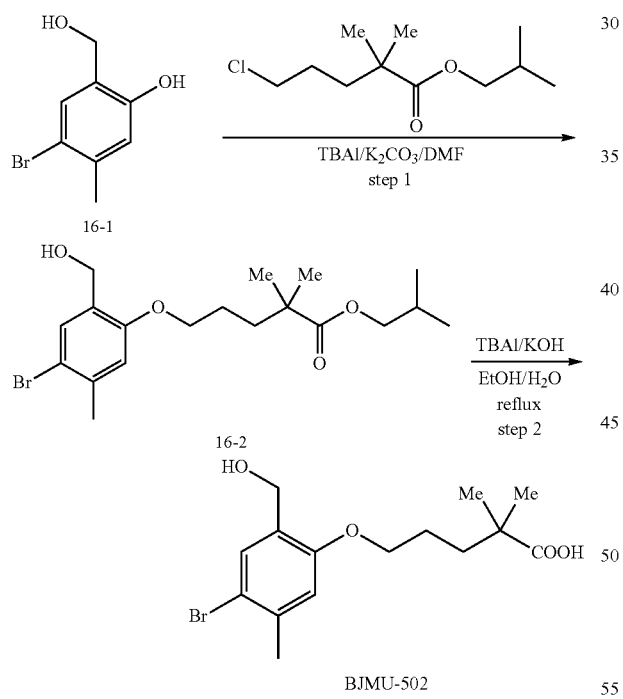

BJMU-502

Compound BJMU-502 was synthesized by a method similar to that described in Step 1 to Step 2 of Example 1, except that in Step 1 of Example 16, Compound 1-1 in Step 1 of Example 1 was replaced with Compound 16-1, and the yield of the two steps was 72%.

$^{1}$H NMR (400 MHz, CDCl$_{3}$) δ 7.41 (s, 1H), 6.71 (s, 1H), 4.62 (s, 2H), 3.94-3.97 (m, 2H), 2.36 (s, 3H), 1.71-1.81 (m, 4H), 1.25 (s, 6H); $^{13}$C NMR (100 MHz, CDCl$_{3}$) δ 155.8, 138.0, 132.1, 128.6, 115.1, 113.6, 68.1, 61.0, 41.9, 36.7, 29.7, 25.1, 23.1.

Example 17: Preparation of 5-(4-bromo-2,5-dimethylphenoxy)-2,2-dimethylvaleronitrile (BJMU-309)

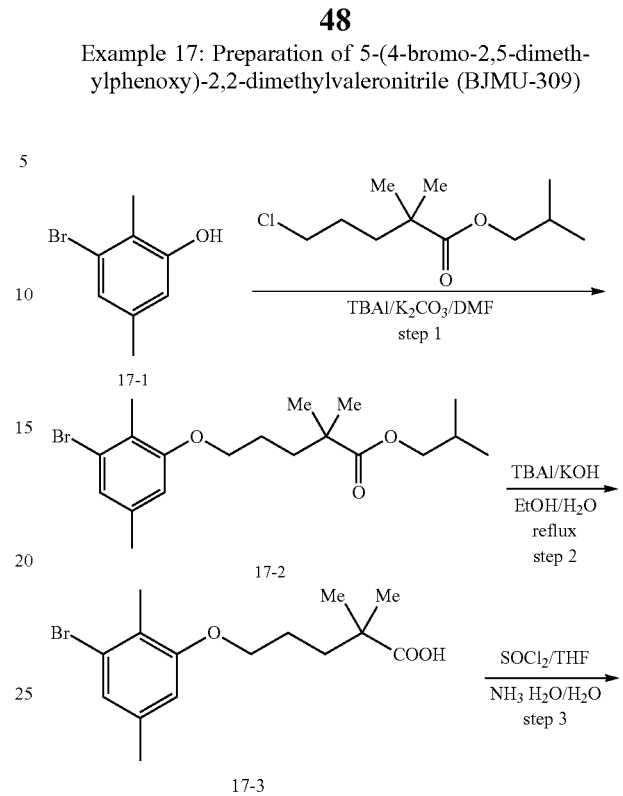

BJMU-309

Compound 17-3 was synthesized by a method similar to that described in Step 1 to Step 2 of Example 1, except that in Step 1 of Example 17, Compound 1-1 in Step 1 of Example 1 was replaced with Compound 17-1, and the yield was 80%.

Step 3: Preparation of 5-(4-bromo-2,5-dimethylphenoxy)-2,2-dimethylpentaneamide (17-4)

Compound 17-3 (1.64 g, 5.0 mmol) was dissolved in THF (10 mL), and stirred for 20 min in condition of ice bath. Thionyl chloride (1.08 mL, 14.8 mmol) was slowly added dropwise to the reaction solution. After the dropwise addition was completed, DMF solution (5 d) was added, heated to 50° C. and reacted for 2 h. After the reaction was completed, the reaction solution was cooled to 0° C., stirred vigorously, and slowly added with concentrated ammonia (4 mL) to precipitate a large amount of white solid, which was filtered with suction, washed with THF, and dried to obtain Compound 17-4 (1.38 g) with a yield of 84%.

Step 4: Preparation of 5-(4-bromo-2,5-dimethylphenoxy)-2,2-dimethylvaleronitrile (BJMU-309)

Compound 17-4 (1.30 g, 4.0 mmol), Pd(OAc)$_2$ (89.6 mg, 0.4 mmol) and selectfluor (283.2 mg, 0.8 mmol) were added into a 100 mL schlenk reaction flask, argon replacement was performed three times, and acetonitrile (20 mL) was added and stirred at 60° C. for 3 h. TLC monitoring indicated no trend of continuous conversion. The reaction solution was filtered, evaporated under reduced pressure to remove solvent, and separated by column chromatography to obtain the target product BJMU-309 (0.93 g) with a yield of 83%.

$^1$H NMR (400 MHz, CDCl$_3$) δ 7.27 (s, 1H), 6.68 (s, 1H), 4.39-3.74 (m, 2H), 2.36 (s, 3H), 2.17 (s, 3H), 2.08-1.94 (m, 2H), 1.87-1.68 (m, 2H), 1.41 (s, 6H). $^{13}$C NMR (101 MHz, CDCl3) δ=173.21, 135.65, 133.67, 126.20, 124.86, 114.75, 113.47, 67.51, 37.76, 32.22, 26.67, 25.50, 22.89, 15.51.

Example 18: Preparation of 5-(4-bromo-2,5-dimethylphenoxy)-2-ethyl-2-methylpentanoic acid (BJMU-401)

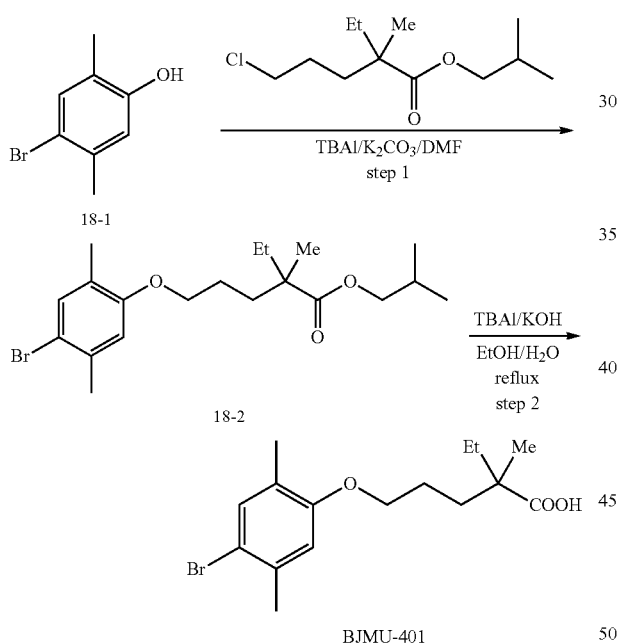

Compound BJMU-401 was synthesized by a method similar to that described in Step 1 to Step 2 of Example 1, except that in Step 1 of Example 18, Compound 1-1 in Step 1 of Example 1 was replaced with Compound 18-1 and isobutyl 5-chloro-2,2-dimethylpentanoate in Step 1 of Example 1 was replaced with isobutyl 5-chloro-2-methyl-2-ethylpentanoate, and the yield of the two steps was 62%.

$^1$H NMR (400 MHz, Chloroform-d): δ 7.25 (s, 1H), 6.64 (s, 1H), 3.90 (td, J=5.8, 2.2 Hz, 2H), 2.33 (s, 3H), 2.14 (s, 3H), 1.87-1.77 (m, 2H), 1.76-1.68 (m, 2H), 1.66-1.48 (m, 2H), 1.18 (s, 3H), 0.98-0.80 (t, J=7.5 Hz, 3H). $^{13}$C NMR (101 MHz, Chloroform-d): δ 156.18, 135.55, 133.61, 126.23, 114.52, 113.40, 68.23, 45.82, 34.74, 31.61, 24.67, 22.86, 20.74, 15.43, 8.81.

Example 19: Preparation of 5-(2,5-dimethyl-4-nitrophenoxy)-2,2-dimethylpentanoic acid (BJMU-110)

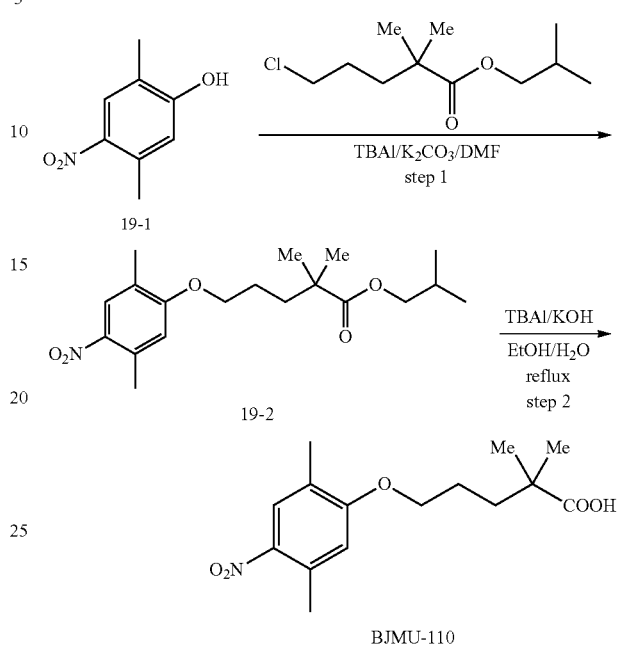

Compound BJMU-110 was synthesized by a method similar to that described in Step 1 to Step 2 of Example 1, except that in Step 1 of Example 19, Compound 1-1 in Step 1 of Example 1 was replaced with Compound 19-1, and the yield of the two steps was 47%.

$^1$H NMR (400 MHz, Chloroform-d) δ 11.99 (s, 1H), 7.92 (s, 1H), 6.62 (s, 1H), 4.02 (t, J=6.0 Hz, 2H), 2.61 (s, 3H), 2.22 (s, 3H), 1.89-1.73 (m, 4H), 1.26 (s, 6H). $^{13}$C NMR (101 MHz, Chloroform-d) δ 184.4, 160.6, 141.1, 134.6, 127.5, 125.5, 113.6, 68.5, 41.9, 36.5, 25.0, 24.8, 21.7, 15.6.

Example 20: Preparation of 5-(4-bromo-2-ethyl-5-methylphenoxy)-2,2-dimethylpentanoic acid (BJMU-410)

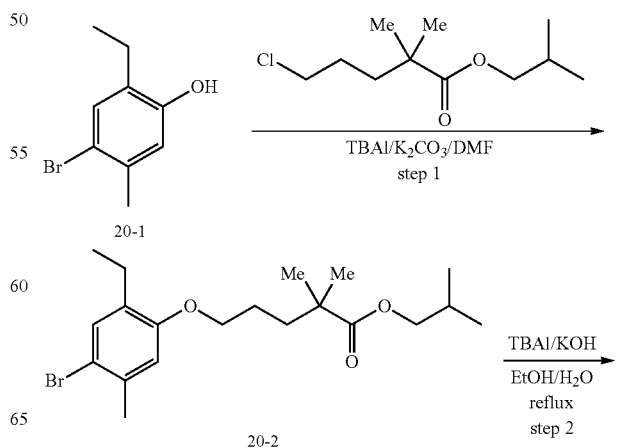

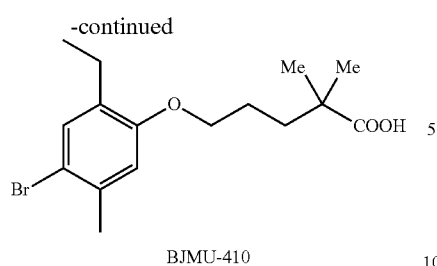

BJMU-410

Compound BJMU-410 was synthesized by a method similar to that described in Step 1 to Step 2 of Example 1, except that in Step 1 of Example 20, Compound 1-1 in Step 1 of Example 1 was replaced with Compound 20-1, and the yield of the two steps was 55%.

$^1$H NMR (400 MHz, CDCl3) δ 12.14 (bs, 1H), 7.29 (s, 1H), 6.70 (s, 1H), 3.94 (t, J=5.9 Hz, 2H), 2.61 (q, J=7.5 Hz, 2H), 2.38 (s, 3H), 1.75-1.89 (m, 4H), 1.29 (s, 6H), 1.21 (t, J=7.5 Hz, 3H). $^{13}$C NMR (101 MHz, CDCl$_3$) δ 184.9, 155.9, 135.6, 132.3, 132.2, 114.9, 113.6, 68.2, 42.0, 36.8, 25.1, 25.0, 22.9, 22.7, 14.1.

Example 21: Preparation of 5-(4-bromo-2,5-dimethoxyphenoxy)-2,2-dimethylpentanoic acid (BJMU-201)

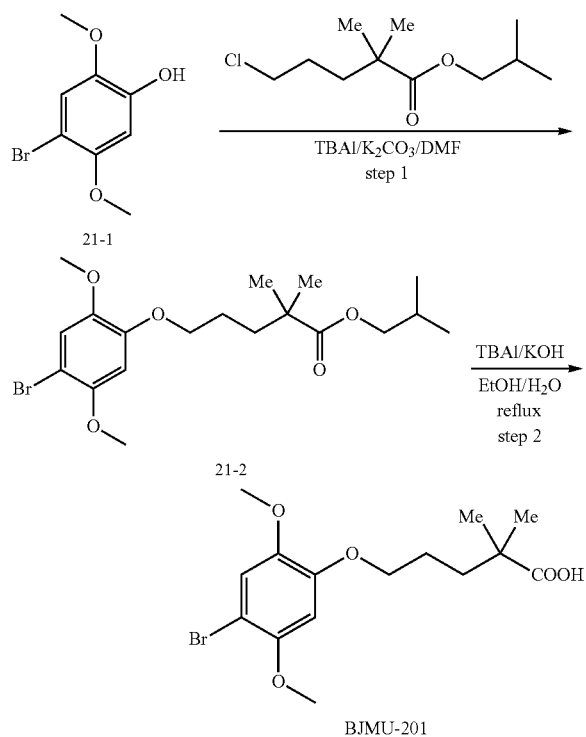

BJMU-201

Compound BJMU-201 was synthesized by a method similar to that described in Step 1 to Step 2 of Example 1, except that in Step 1 of Example 21, Compound 1-1 in Step 1 of Example 1 was replaced with Compound 21-1, and the yield of the two steps was 85%.

$^1$H NMR (400 MHz, CDCl3) δ 7.06 (s, 1H), 6.57 (s, 1H), 4.02 (t, J=6.6 Hz, 2H), 3.86 (s, 3H), 3.83 (s, 3H), 1.94-1.81 (m, 2H), 1.74 (dd, J=11.2, 5.0 Hz, 2H), 1.26 (s, 6H). $^{13}$C NMR (101 MHz, CDCl3) δ 184.19, 150.32, 148.51, 144.33, 117.20, 101.49, 100.75, 69.81, 57.14, 56.86, 41.94, 36.48, 24.98, 24.95.

Example 22: Preparation of 4-(4-bromo-2,5-dimethylphenoxy)-2,2-dimethylbutanoic acid (BJMU-111)

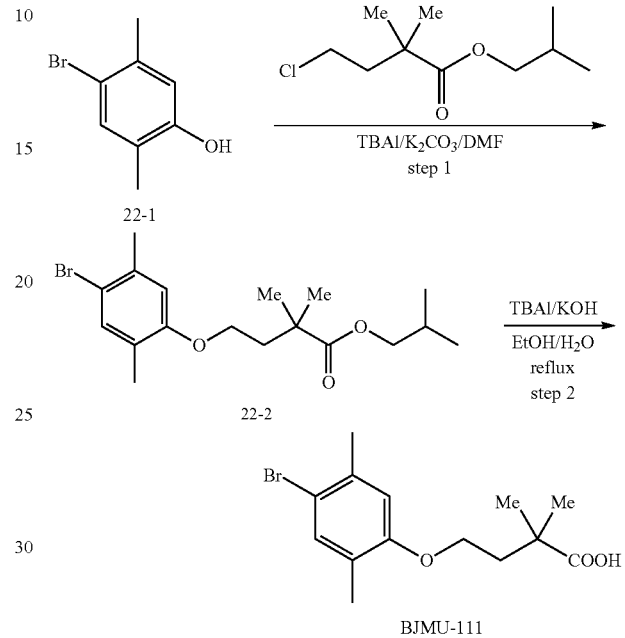

BJMU-111

Compound BJMU-111 was synthesized by a method similar to that described in Step 1 to Step 2 of Example 1, except that in Step 1 of Example 22, Compound 1-1 in Step 1 of Example 1 was replaced with Compound 22-1 and isobutyl 5-chloro-2,2-dimethylpentanoate in Step 1 of Example 1 was replaced with isobutyl 5-chloro-2,2-dimethylbutyrate, and the yield of the two steps was 75%.

$^1$H NMR (400 MHz, Chloroform-d) δ 11.99 (s, 0.5H), 7.21 (s, 1H), 6.65 (s, 1H), 3.99 (t, J=6.4 Hz, 2H), 2.33 (s, 3H), 2.13-2.10 (m, 5H), 1.30 (s, 6H). $^{13}$C NMR (101 MHz, Chloroform-d) δ 184.5, 156.0, 135.5, 133.6, 126.1, 114.6, 113.0, 64.6, 40.7, 39.0, 25.3, 22.9, 15.4.

Example 23: Preparation of 4-(4-bromo-2,5-dimethylphenoxy)-2,2-dimethylhexanoic acid (BJMU-403)

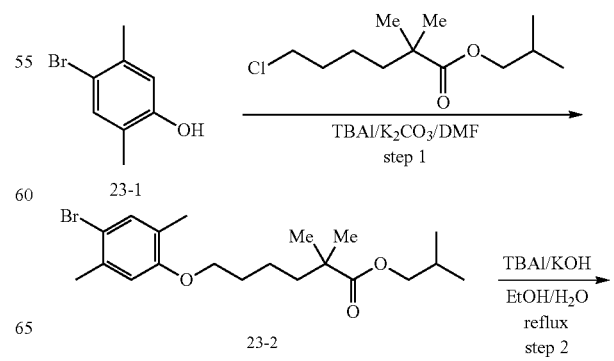

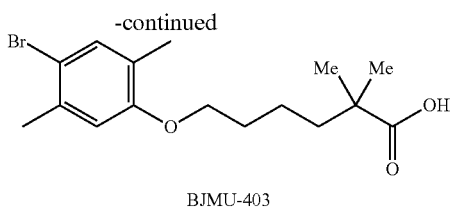

BJMU-403

Compound BJMU-403 was synthesized by a method similar to that described in Step 1 to Step 2 of Example 1, except that in Step 1 of Example 23, Compound 1-1 in Step 1 of Example 1 was replaced with Compound 23-1 and isobutyl 5-chloro-2,2-dimethylpentanoate in Step 1 of Example 1 was replaced with isobutyl 5-chloro-2,2-dimethylhexanoate, and the yield of the two steps was 45%.

$^1$H NMR (400 MHz, CDCl$_3$): δ (ppm): 7.27 (s, 1H), 6.68 (s, 1H), 3.94 (t, J=6.4 HZ, 2H), 2.36 (s, 3H), 2.16 (s, 3H), 1.76-1.84 (m, 2H), 1.46-1.67 (m, 4H), 1.24 (s, 6H). $^{13}$C NMR (100 MHz, CDCl$_3$): δ (ppm): 184.6, 156.3, 135.6, 133.6, 126.3, 114.5, 113.5, 67.8, 42.1, 40.0, 29.7, 24.9, 22.8, 21.5, 15.4.

Biological Activity Experiment

The cells, reagents and instruments involved in in vitro experiments in the following experimental examples were as follows:

Drugs:

Compounds obtained by the preparation of the examples; control drug: Gemfibrozil (purchased from Beijing Ouhe Technology Co., Ltd.).

Cells:

RAW264.7 mouse macrophages, human colon cancer cells SW480, human liver cancer cells HepG2, and human liver cells L02, all came from the ATCC cell bank.

Culture Media:

RPMI1640 medium containing 10% fetal bovine serum (FBS) and DMEM high glucose medium containing 10% fetal bovine serum (FBS).

Cell Culture:

In an environment maintained at 37° C., 5% CO$_2$ and saturated humidity, after incubation was carried out to 80% confluence, digestion treatment was performed with 0.25% trypsin-EDTA.

Main Reagents and Instruments Involved:

RIPA cell lysate, BCA protein concentration test kit (Beyotime Institute of Biotechnology, Jiangsu); Phenylmethanesulfonyl fluoride (PMSF), β-mercaptoethanol, acrylamide (Sigma, USA); ECL™ Prime Western Blotting detection reagent (Bio-Rad, USA); glycine, sodium lauryl sulfonate (Amresco, USA); RPMI1640 medium, DMEM high glucose medium, trypsin (Gibco, Maryland, USA); fetal bovine serum (GBO, Germany); nitric oxide (NO) assay kit (Nanjing Jiancheng, China); luciferase reporter gene assay kit (Beyotime Institute of Biotechnology, Jiangsu); Tranzol reagent (Tranzol total RNA extraction reagent, TransGen Biotech); 5× All-In-One RT MasterMix reverse transcription kit (Abcam, USA); CPT1α rabbit polyclonal antibody (12252S, CST, USA), p-GSK3β (Ser9) rabbit polyclonal antibody (9323, CST, USA), pIRS-1 (Ser636/639) rabbit polyclonal antibody (2388, CST, USA), β-Tubulin mouse monoclonal antibody (BE0025, EASYBIO, China).

INCO246 cell incubator (Memmert, Germany); Gen5 synergy H1 Take3 (BioTek, USA) multifunctional microplate reader; fluorescence real-time quantitative PCR instrument, protein electrophoresis system (Bio-Rad, USA); low-temperature refrigeration high-speed centrifuge (Eppendorf, Germany); electrophoresis instrument and horizontal electrophoresis tank (Beijing Junyi Dongfang Electrophoresis Equipment Co., Ltd., China).

Experimental Example 1: Evaluation of Compounds' Cytotoxicity

In this experiment, the compounds' cytotoxicity was determined by the SRB method. The specific steps were as follows:

(1) Cells at log phase were collected; the cell suspension was adjusted to a concentration of about 3×10$^3$/100 μL culture medium; cells were added to a middle area of a 96-well plate, sterile PBS was added to edge holes, and routine culture was performed overnight in condition of 5% CO$_2$, 37° C.

(2) The compound was formulated with serum-free medium, with final concentration of 10 μM; the 96-well plate medium was removed, washing was performed with PBS, the prepared compound to be tested was added, and routine regular culture was performed for 24 hours.

(3) Cell fixation: At the end of the action of compound, 50 μL of 4° C. pre-cooled trichloroacetic acid (TCA) solution (30%, w/v) was added to each well of plate to fix the cells. The final concentration of the TCA solution was 10%. After standing for 5 min, the plate was moved into a refrigerator at 4° C. to perform fixation for 1 h, then taken out and rinsed with deionized water 5 times, and air-dried at room temperature.

(4) Staining: After the 96-well plate was air-dried at room temperature, 70 μL of 0.4% (w/v) SRB dye solution (prepared with 1% acetic acid) was added to each well, the dye solution was discarded after dyeing for 30 min, and 1% (v/v) acetic acid was used for rinsing 4 times to remove unbound dye, and air-dried at room temperature.

(5) Determination: 100 μL of non-buffered Tris-base lye (10 mM, pH=10.5) was used to dissolve the dye bound to cell proteins, shaking was performed on a horizontal shaker for 20 min, and the absorbance value at 540 nm was measured with a microplate reader.

(6) Relative cell viability refers to a percentage of cell viability of the cells in a sample well under the action of drug relative to that of the cells in a negative control well, and the calculation formula was: relative cell viability=(Tx−C)/(T0−C)*100%, wherein, T0 represents an average absorbance value of a negative control with a medium added with an equal volume of DMSO without drug action (negative control); Tx represents an average absorbance value of cells measured after the cells were treated with drug, fixed and stained; C represents an average absorbance value of a blank well that was already fixed and stained.

The test results of L02 human normal liver cells were shown in FIG. 1. The results showed that after the normal liver cells were treated with BJMU-1, 2, 3, 110, 111, 113, 114, 115, 201, 203, 204, 205, 209, 212, 213, 214, 404, 409, 415, 416 or 502, less than 30% of cell viability was inhibited (relative cell viability was greater than 70%), and the above compounds had no significant cytotoxicity.

Experimental Example 2: Evaluation of Regulatory Effect of Compound on Cellular Inflammatory Response In this experimental example, the generation of nitric oxide (NO) and the transcriptional activity of NF-κB inflammation signal pathway were tested to evaluate the regulatory effect of compound on cell inflammatory response.

2.1 Determination of NO Generation

NO is a reactive nitrogen species (RNS) and an important gas signal molecule. Macrophages could convert arginine into NO which participated in the body's inflammatory response. Therefore, determination of inhibitory activity of a drug on NO generation was one of the classic methods to evaluate drug's anti-inflammatory ability. RAW264.7 cells at exponential growth phase were inoculated into a 96-well plate at $1 \times 10^4$ cells/200 µL. well of medium. After adherence, the medium was discarded, and the cells were subjected to drug treatments. Normal group (serum-free medium), LPS model group (serum-free medium containing 1 µg/mL LPS), LPS+drug group (serum-free medium containing 1 µg/mL LPS, 10 µM gemfibrozil or the compound of the present application) were established, and 3 repeated wells were set for each group. After 24 hours incubation in incubator, cell supernatant of each well was collected and assay was performed according to the instructions of NO determination kit (Nanjing Jiancheng). The absorbance value of each well at wavelength of 540 nm was read and NO content was calculated.

Figure 2:
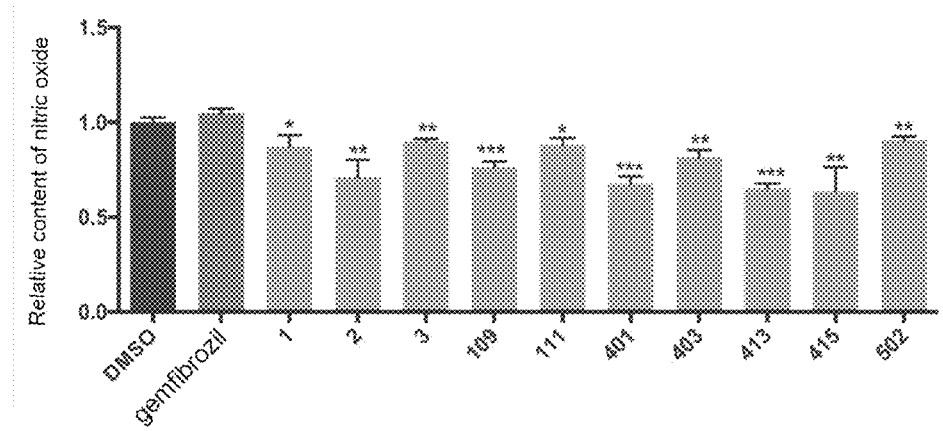
FIG. 2 shows the effect of the compound on NO production induced by LPS in RAW264.7 mouse macrophages. The results are expressed as the multiple of the NO content in the cell culture supernatant of the administration group (10 μM) as compared with that in the cell culture supernatant of the control group (DMSO group), in which compared with the control group, *$P<0.05$, $P<0.01$, *$P<0.001$.

The results were shown in FIG. 2. The tested compounds 1, 2, 3, 109, 111, 401, 403, 413, 415 and 502 could inhibit NO generation. In contrast, gemfibrozil (BJMU) did not have an activity of inhibiting NO generation. The above results indicated that the compound of the present application had significant anti-inflammatory activity.

2.2 Determination of Transcriptional Activity of NF-κB Luciferase Reporter Gene

NF-κB was the most important inflammatory signal pathway. SW480 human colon cancer cells stably transfected with a luciferase reporter gene driven by NF-κB were used to determine the effects of the compound of the present application and the control drug gemfibrozil on NF-κB transcriptional activity, which comprised the following steps.

(1) Cells stably transfected with NF-κB Luc were cultivated to exponential growth, inoculated at a culture medium concentration of $1 \times 10^5$/2000 µL in a 24-well plate, and cultured for 24 hours, the medium was discarded, and the test compound or gemfibrozil formulated with serum-free medium at 50 µM were added to the 24-well plate and incubation was continued for 6 hours. After washing once with 200 µL of PBS, 100 µL of reporter gene cell lysis buffer was added, the cells were lysed on ice for 10 minutes, and the cell lysate was collected by pipetting.

(2) After centrifugation was performed at 8000 rpm and 4° C. for 10 min, the supernatant was pipetted for fluorescence assay.

(3) The measurement gap time of chemiluminescence analyzer was set to 2 s and the measurement time was set to 10 s. Automatic sample injection was adopted, 50 µL of luciferase assay reagent was added to each well. The reporter gene cell lysis buffer was used as a blank control.

(4) After centrifugation, the supernatant was taken, and the BCA method was used to determine the protein concentration so as to normalize the reporter gene results.

Figure 3:
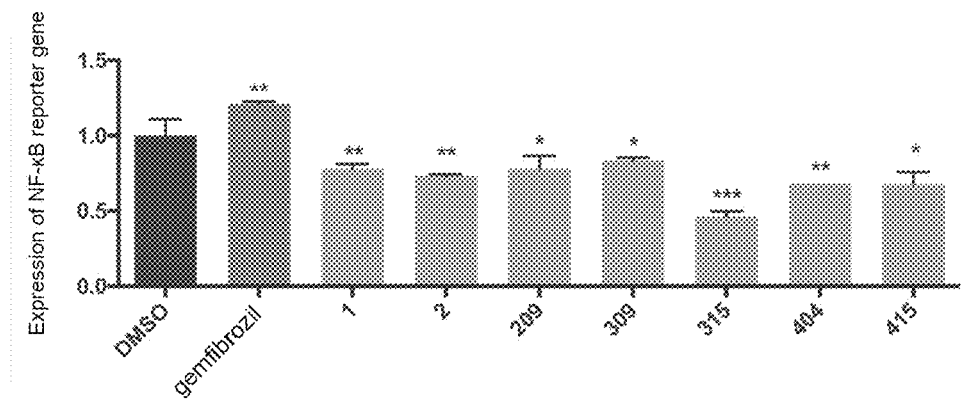
FIG. 3 shows the effect of the compound on the expression of NF-κB reporter gene, and the results are expressed as the multiple of the activity of luciferase reporter gene in the cells of the administration group (50 μM) as compared with that in the cells of the control group (DMSO group), in which compared with the control group, *P<0.05, P<0.01, *P<0.001.

The results were shown in FIG. 3. The tested compounds 1, 2, 209, 309, 315, 404 and 415 could significantly inhibit the activity of NF-κB reporter gene. In contrast, gemfibrozil could not inhibit the activity of NF-κB reporter gene. The above results further indicated that the compound of the present application has obvious anti-inflammatory activity that gemfibrozil does not possess.

It is known in the art that long-term chronic inflammation is a key event in the progression of MS, NAFLD and diabetes mellitus, and the continuous activation of NF-kB signals is a typical feature thereof. Thus, it is an important means to inhibit NF-kB signals for the control of progression and complications of the aforementioned diseases (see: references [1] to [4]), so the above experimental results could show that the compound of the present application could be used for the prevention and/or treatment of MS, NAFLD and diabetes mellitus as well as complications thereof.

Experimental Example 3: Evaluation of Regulatory Effect of Compound on Cellular Oxidative Stress Response Signal In this experimental example, the luciferase activity in HepG2 human liver cancer cells stably transfected with a luciferase reporter gene driven by antioxidant response element (ARE) was determined to evaluate the regulatory effects of the compound of the present application and gemfibrozil on the transcriptional activity of transcription factor Nrf2 and the cellular oxidative stress response signals, in which the operation process of the reporter gene assay was the same as that of Experimental Example 2.2.

Figure 4:
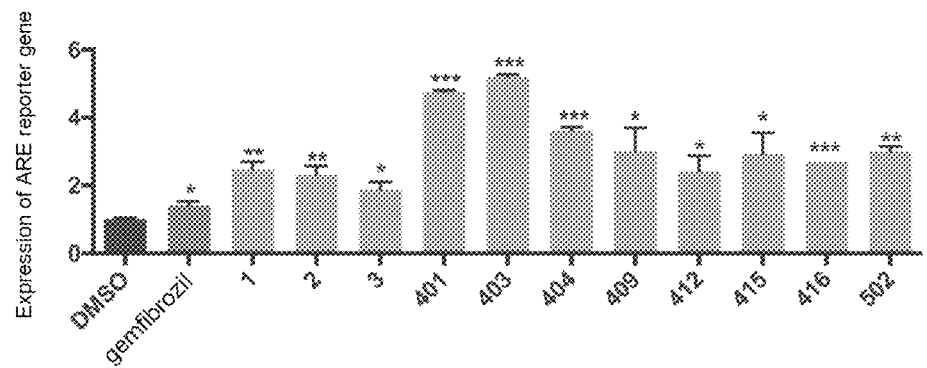
FIG. 4 shows the effect of the compound on the activity of ARE reporter gene, and the results are expressed as the multiple of the activity of luciferase reporter gene in the cells of the administration group (50 μM) as compared with that in the cells of the control group (DMSO group), in which compared with the control group, *P<0.05, P<0.01, *P<0.001.

The results were shown in FIG. 4. The tested compounds 1, 2, 3, 401, 403, 404, 409, 412, 415, 416 and 502 could significantly activate the ARE reporter gene activity. In contrast, gemfibrozil did not obviously activate the ARE. The above results showed that the compound of the present application could exert an antioxidant effect by activating antioxidant response element to induce the expression of cellular antioxidant and metabolic detoxification genes, and had significant antioxidant activity.

Since it was known in the art that oxidative stress was one of the most important pathogenic factors in the occurrence and progression of MS, NAFLD and diabetes mellitus, and antioxidant and activation of Nrf2-mediated cellular antioxidant response had always been important strategies for the prevention and treatment thereof (see: references [5] to [9]), so the above experimental results could indicate that the compound of the present application could be used for the prevention and/or treatment of MS, NAFLD and diabetes mellitus as well as complications thereof.

Experimental Example 4: Evaluation of Regulatory Effects of Compound on Cellar Glycolipid Metabolism Signaling Pathway and Gene Expression Peroxisome proliferation factor activated receptor (PPAR) is an important nuclear receptor that regulates glycolipid metabolism, including three subtypes: α, β/δ and γ. Peroxisome proliferator-activated receptor γ coactivator 1α (PGC-1α) is its auxiliary transcriptional activator. Acyl-CoA oxidase 1 (ACOX1) is the first rate-limiting enzyme for fatty acid β oxidation. Fatty acid binding protein 1 (FABP1) is highly expressed in liver, and can bind fatty acid, heme and other molecules to reduce their toxicity and damage. Up-regulating the expression level of these genes helps to improve the body's metabolism, and their agonists are an important class of anti-metabolic drugs. After the compound of the present application (1 µM) and the control drug gemfibrozil (1 µM) were incubated with human liver cancer cells HepG2 for 6 hours, real-time fluorescent quantitative PCR method was used to determine the relative expression of mRNA of related genes in the cells.

```
Primer sequences:
PPARα
Upstream:
                                (SEQ ID NO: 1)
CATTACGGAGTCCACGCGT Downstream:
                                (SEQ ID NO: 2)
ACCAGCTTGAGTCGAATCGTT PPARγ
Upstream:
                                (SEQ ID NO: 3)
GTACTGTCGGTTTCAGAAATGCC Downstream:
                                (SEQ ID NO: 4)
ATCTCCGCCAACAGCTTCTCCT PGC1α
Upstream:
                                (SEQ ID NO: 5)
GCTACGAGGAATATCAGCACGA Downstream:
                                (SEQ ID NO: 6)
TCACACGGCGCTCTTCAA ACOX1
Upstream:
                                (SEQ ID NO: 7)
CTGTAGGACCATTGTCTCG Downstream:
                                (SEQ ID NO: 8)
TTACACTCTGCACTCCAAAG FABP1
Upstream:
                                (SEQ ID NO: 9)
CACCCCCTTGATATCCTTCC Downstream:
                                (SEQ ID NO: 10)
TTCTCCGGCAAGTACCAACT
```

The company which synthesized the primers was Suzhou Hongxun Biotechnology Co., Ltd. Tranzol reagent (Tranzol total RNA extraction reagent, TransGen Biotech) was used to extract total RNA from tissues. 5× All-In-One RT MasterMix reverse transcription kit (Abcam, USA) and real-time quantitative PCR Master Mix (Aidlab Biotechnologies Co., Ltd) were used. Bio-Rad CFX Connect™ Real-Time PCR Detection System for qPCR was used, and $2^{-\Delta\Delta C_T}$ method was used for data analysis. The expression level of mRNA in the normal control group was set to 1, and the relative expression level of mRNA in the administration group was calculated, so as to confirm whether the active compound affected the PPAR pathway, thereby further regulating lipid metabolism.

Figure 5:
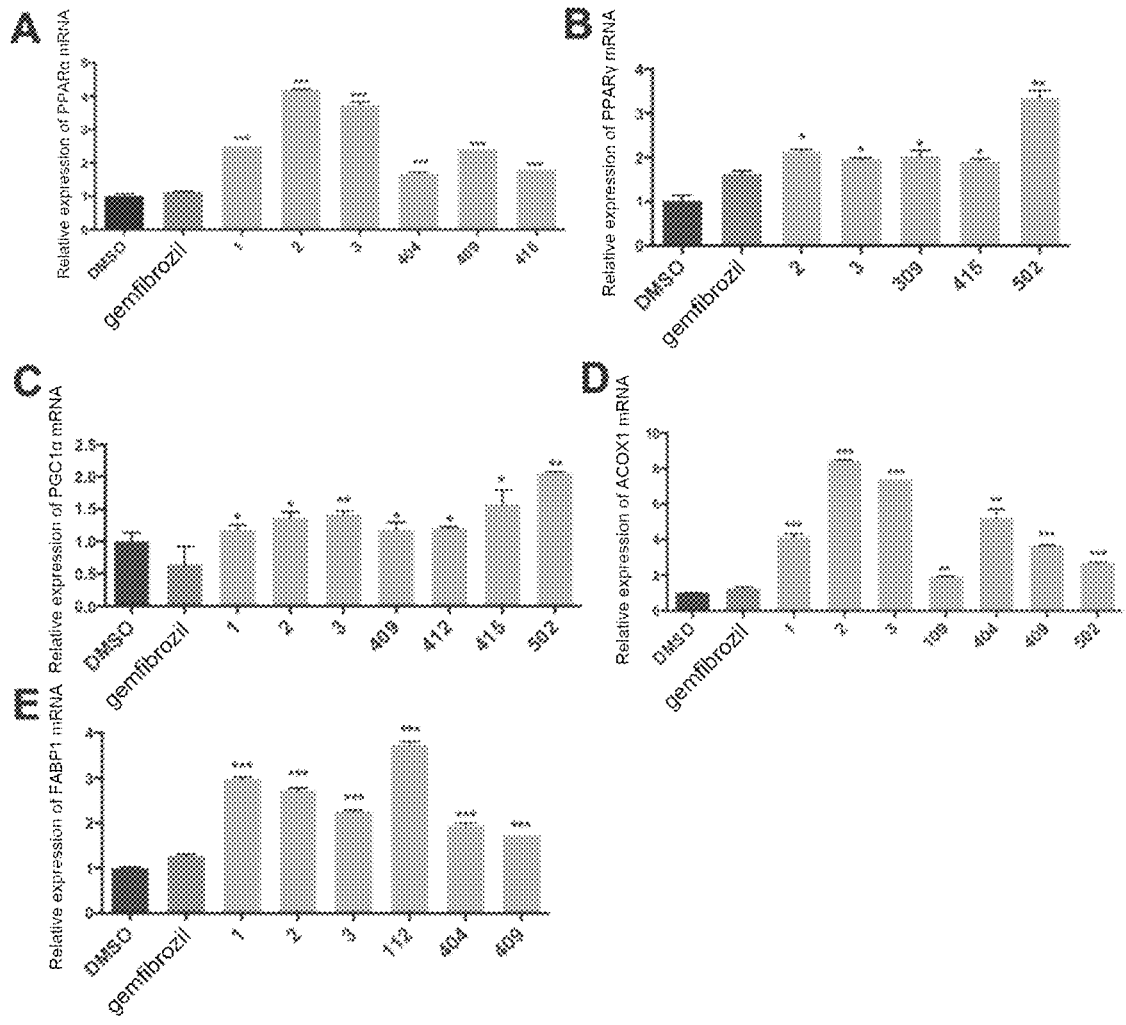
FIG. 5 shows the effects of the compound on the mRNA levels of PPARα (A), PPARγ (B), PGC1α (C), ACOX1 (D), FABP1 (E) respectively, and the results are expressed as the multiple of the relative expression amount of mRNA of the corresponding gene in the cells of the administration group (1 μM) as compared with that in the cells of the control group (DMSO group), in which compared with the gemfibrozil group, *P<0.05, P<0.01, *P<0.001.

The test results were shown in FIG. 5. The determination results of PPARα mRNA expression were shown in FIG. 5A, in which the tested compounds 1, 2, 3, 404, 409 and 416 significantly induced PPARα mRNA expression by more than 1.5 times with significant difference, and were better than gemfibrozil. In particular, it was known in the art that gemfibrozil required a higher dose (50 to 100 μM) to significantly activate PPARα, while the above-mentioned tested compounds had a dose of only 1 μM.

The test results of PPARγ mRNA expression were shown in FIG. 5B. The tested compounds 2, 3, 309, 415 and 502 significantly induced PPARγ mRNA expression.

The test results of PGC1α mRNA expression were shown in FIG. 5C. The tested compounds 1, 2, 3, 409, 412, 415 and 502 significantly induced PGC1α mRNA expression. In contrast, gemfibrozil could not activate PGC1α expression.

The test results of ACOX1 mRNA expression were shown in FIG. 5D. The tested compounds 1, 2, 3, 109, 404, 409 and 502 significantly induced PGC1α mRNA expression. In contrast, gemfibrozil could not activate ACOX1 expression.

The test results of ACOX1 mRNA expression were shown in FIG. 5D. The tested compounds 1, 2, 3, 109, 404, 409 and 502 significantly induced ACOX1 mRNA expression. In contrast, gemfibrozil could not activate ACOX1 expression.

The above results indicated that the compound of the present invention could up-regulate the expression of PPARα/γ, PGC1α, ACOX1 and FABP1, and had PPARα/γ dual agonistic activity and glycolipid metabolism regulation activity that gemfibrozil did not possess, so that it was particularly suitable for regulating glycolipid metabolism, and could have better lipid-lowering activity than gemfibrozil.

In addition, the inventors also tested the effects of the compounds on the expression levels of multiple glycolipid metabolism-related genes such as MTTP, UCP1/2, Elovl3 and CD36. The results showed that the above-mentioned compounds could significantly regulate the expression of these genes, further confirming the compound of the present invention has superior activity of regulating lipid metabolism.

Experimental Example 5: Effect of Compound on Glycolipid Metabolism-Related Protein Level and Fatty Acid Oxidation Rate-Limiting Enzyme CPT1α Protein Level Carnitine palmitoyltransferase (CPT1α) is a rate-limiting enzyme of fatty acid oxidation. When the body or tissues are lacking in energy, CPT1α catalyzes the entry of fatty acids into mitochondria for 13 oxidation, and at the same time, CPT1α is also involved in the regulation of fatty acid-induced insulin resistance and inflammation. Protein kinase B/glycogen synthase kinase 3β (AKT/GSK3β) signaling pathway and insulin receptor substrate 1 (IRS-1) are key signaling pathways that regulate glucose metabolism in response to insulin signal. Therefore, by determining the effects of compounds on the CPT1α protein level and the AKT, GSK3β and IRS-1 protein phosphorylation levels, it is possible to evaluate the regulatory effects of the compounds on glycolipid metabolism.

Figure 6:
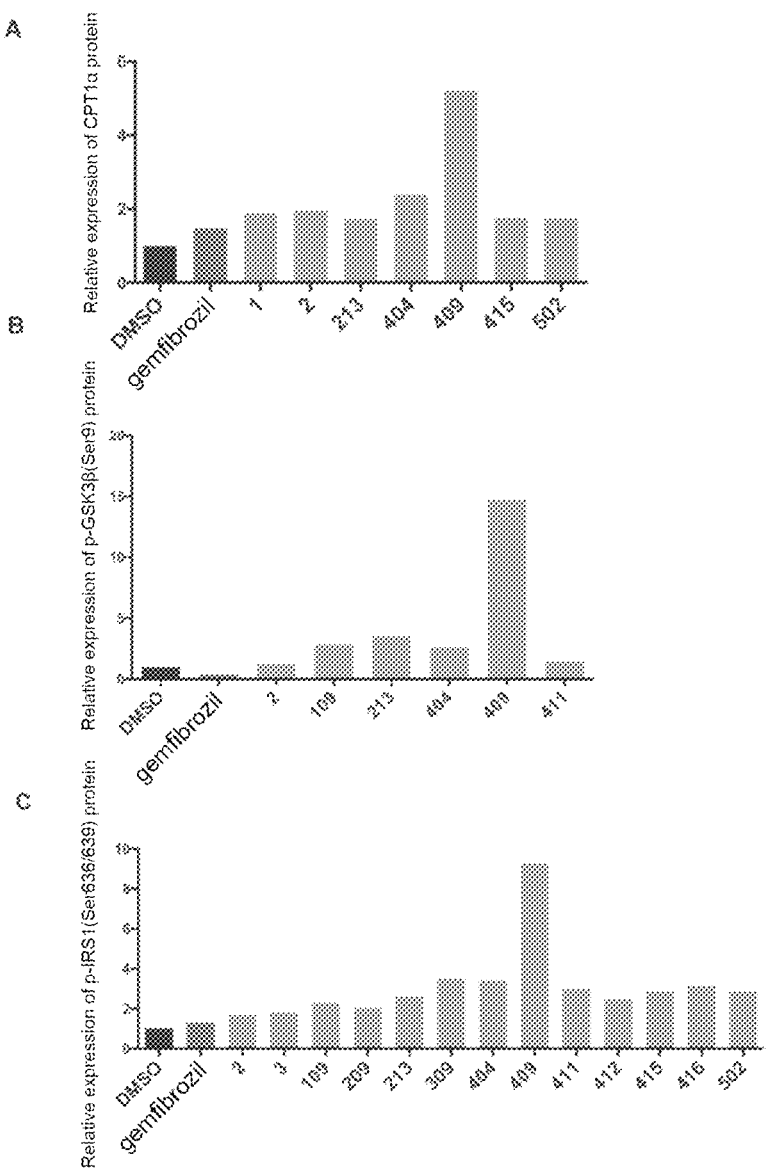
FIG. 6 shows the effects of the compound on the protein levels of CPT1α (A), phosphorylated GSK3β (B), and phosphorylated IRS-1 (C), and the results are expressed as the multiple of the corresponding protein level quantified by Western blotting in the cells of the administration group (1 μM) as compared with that in the cells of the control group (DMSO group).

After human liver cancer cells HepG2 were incubated with the compound of the present application or the control drug at 1 μM for 24 hours, the CPT1α protein level and the AKT, GSK3β and IRS-1 phosphorylated protein levels in the cells were determined by Western blotting; after gray-scale scanning by using Image J15.0.1, normalization was performed by using β-tubulin protein level as internal control, and the quantitative analysis results were shown in FIG. 6. The tested compounds 1, 2, 213, 404, 409, 415 and 502 all significantly increased CPT1α protein level (FIG. 6A), the tested compounds 2, 109, 213, 404, 409 and 411 all significantly increased the phosphorylation level of GSK3β (FIG. 6B), the tested compounds 2, 3, 109, 209, 213, 309, 404, 409, 411, 412, 415, 416 and 502 all significantly increased the phosphorylation level of IRS-1 (FIG. 6C). The above results indicated that the above compounds could regulate insulin signaling and fatty acid oxidation, thereby improving the glycolipid metabolism in liver.

In addition, the inventors also tested the effects of the compounds on the phosphorylation levels of many glycolipid metabolism-related proteins such as Akt, HSL, ACC and PKA substrates. The results showed that the above-mentioned compounds could significantly regulate the phosphorylation levels of these proteins, further confirming that the compound of the present invention has superior activity of regulating lipid metabolism.

Experimental Example 6: Evaluation of the Therapeutic Effect of the Compound on Diabetic Mice 6.1 Diabetes Mellitus Model:

Animal model: C57BL/KsJ-leprdb/leprdb diabetic (db/db) mice were widely used as animal models of type 2 diabetes mellitus, in which spontaneous mutations of leptin receptor (Leptin receptor, Lepr) caused extreme obesity, polyphagia, diabetes and polyuria. In this experiment, db/db mice (purchased from the Department of Animals, Health Science Center of Peking University) were selected.

In the experiment, 28 db/db mice were used, and the animals with blood glucose of about 7-13 mmol/L were selected. According to their blood glucose levels, they were randomly divided into a control group, a BJMU group (gemfibrozil), a BJMU-2 group and a positive control group (pioglitazone), 7 animals in each group. Intragastric administration was adopted with an administration volume of 10 ml/kg. The control group was administrated with 1% Tween 80-saline; the BJMU group was administrated with a dose of 50 mg/kg, the BJMU-2 group was administrated with a dose of 50 mg/kg, and the positive control group was administrated with pioglitazone at a dose of 6 mg/kg. The administration was performed once a day for 28 consecutive days. From the day of oral administration, the physiological changes of the animals were observed every day. Blood glucose was measured every 3 days (Roche blood glucose meter) and blood glucose difference ($\Delta$) was calculated by the following formula: blood glucose difference ($\Delta$)=the blood glucose of the day—the initial blood glucose (the initial blood glucose difference was zero).

For mice in each experimental group, blood was collected, serum was separated, and liver was taken for wet-weight measurement after necropsy; liver tissue was taken and fixed for pathological examination, H.E. staining and oil red O staining (Wuhan Zishan Biotechnology Co., Ltd.) were performed, and mouse liver lesions were observed under light microscope; routine examination of blood was performed by Animal Laboratory Department, Health Science Center of Peking University to measure the following indexes: white blood cell count (WBC), red blood cell count (RBC), lymphocyte count (LY), platelet (PLT) and so on; biochemical laboratory examination of blood was performed by Laboratory Medicine, Third Hospital, Peking University to measure the following indexes: triglycerides (TG), total cholesterol (T-CHO), high-density lipoprotein cholesterol (HDL-C), low-density lipoprotein cholesterol (LDL-C) and so on.

Figure 7:
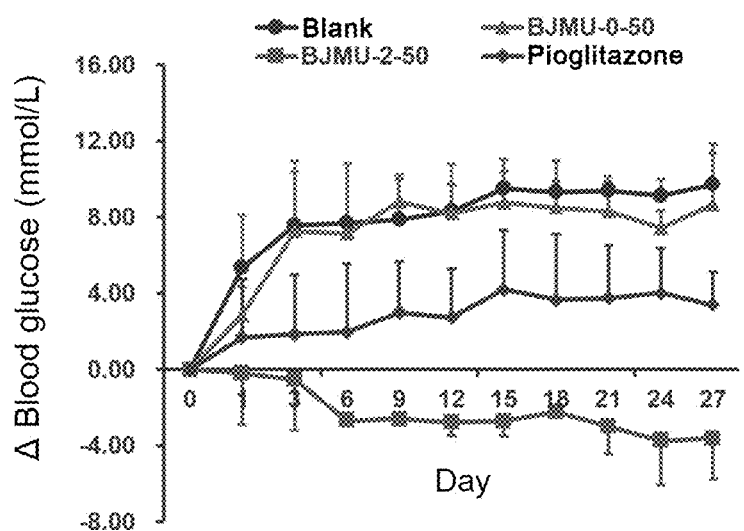

The measurement results of blood glucose were shown in FIG. 7. The tested compound BJMU-2 could significantly reduce the blood glucose level of db/dbmice, and was even better than the known hypoglycemic agent pioglitazone. In contrast, gemfibrozil did not show obvious hypoglycemic activity. This result indicated that the compound of the present invention exhibited significant hypoglycemic activity.

The measurement results of blood lipid indexes were shown in the following table. The tested compound BJMU-2 had an activity of lowering triglycerides better than gemfibrozil. In particular, BJMU-2 could reduce the total cholesterol content in the blood of db/dbmice. In contrast, gemfibrozil did not show the activity of lowering total cholesterol in blood. The above results indicated that BJMU-2 had a more prominent effect of reducing blood lipids.

TABLE 1

Measurement results of blood lipid indexes

| Group | Dose (mg/kg) | CHOL (mmol/L) | TGL (mmol/L) | AHDL (mmol/L) | ALDL (mmol/L) |
|---|---|---|---|---|---|
| Control group | 0 | 3.44 ± 0.41 | 2.15 ± 0.53 | 1.68 ± 0.28 | 0.41 ± 0.05 |
| Pioglitazone | 6 | 3.45 ± 0.26 | 2.17 ± 0.61 | 1.65 ± 0.29 | 0.38 ± 0.03 |
| BJMU | 50 | 3.37 ± 0.36 | 2.09 ± 0.95 | 1.64 ± 0.28 | 0.35 ± 0.02 |
| BJMU-2 | 50 | 3.06 ± 0.63 | 1.44 ± 0.42* | 1.59 ± 0.13 | 0.33 ± 0.09 |

Note:
Compared with the model control group,
*$P < 0.05$,
**$P < 0.01$.
CHOL: total cholesterol; TGL: triglycerides; AHDL: high density lipoprotein, ALDL: low density lipoprotein.

Figure 8A:
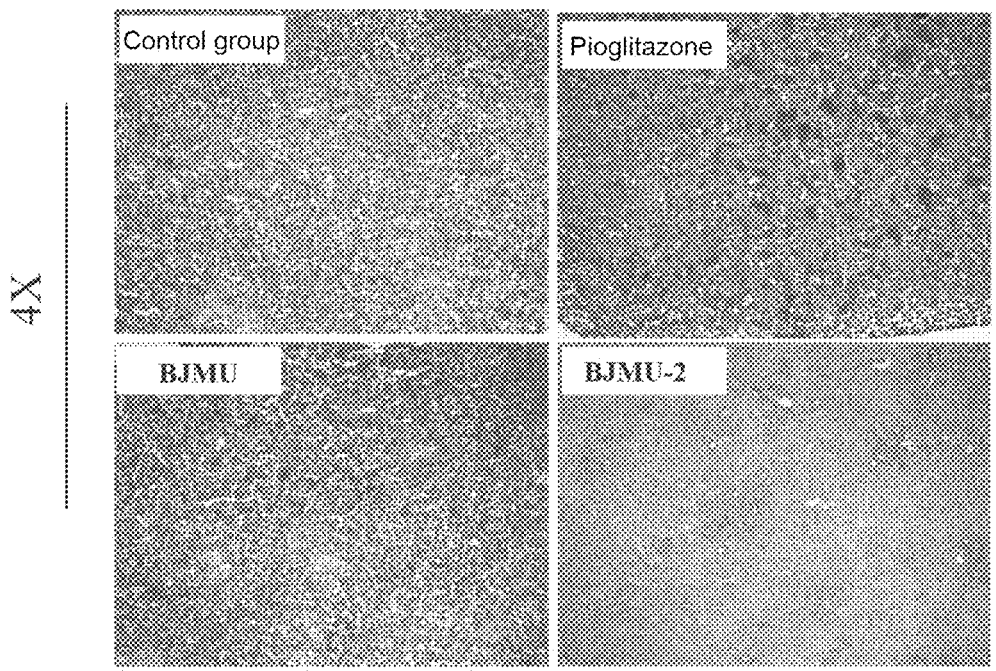
FIGS. 8A to 8B show the effects of the compound on fat contents in liver tissues of DB/DB mice.
Figure 8B:
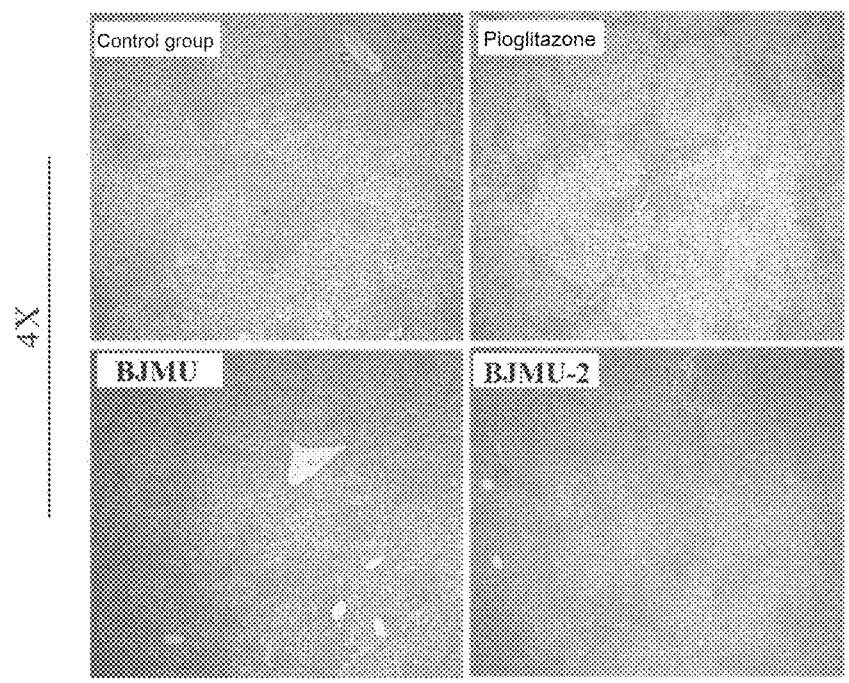

The pathological examination results of liver tissue were shown in FIGS. 8A to 8B. The results showed that the tested compound BJMU-2 could significantly reduce the fat content in the liver of model mice. In contrast, neither gemfibrozil nor pioglitazone showed the above activity. The above results indicated that BJMU-2 not only had a significant activity in reducing blood lipids, but also a significant activity in reducing liver fat.

In addition, the measurement date of mouse liver function and kidney function indexes (Table 2) showed that the tested compound would not cause liver and kidney toxicity after continuous intragastric administration at a dose of 50 mg/kg for one month. This result indicated that the compound of the present invention had good in vivo safety.

TABLE 2

Data of mouse liver function and kidney function indexes

| Group | Dose (mg/kg) | AST (U/L) | ALT (U/L) | BUN (mmol/L) | CREA (umol/L) | CK (U/L) |
|---|---|---|---|---|---|---|
| Control group | 0 | 218.4 ± 48.25 | 226.5 ± 67.64 | 10.92 ± 1.3 | 15.9 ± 5.37 | 1025.4 ± 375.81 |
| Pioglitazone | 6 | 212.79 ± 91.2 | 225.43 ± 79.31 | 11.4 ± 5.48 | 12 ± 3.91 | 1482.86 ± 707.74 |
| BJMU | 50 | 225 ± 132.19 | 172.25 ± 123 | 9.56 ± 1.57 | 16 ± 10.46 | 1037 ± 523.17 |
| BJMU-2 | 50 | 210.75 ± 56.97 | 187.75 ± 62.07 | 7.23 ± 1.19 | 10.13 ± 5.25 | 1790.75 ± 388.38 |

6.2 Diabetes Mellitus+Non-Alcoholic Steatohepatitis (NASH) Model:

Animal model: Each db/db mouse was injected subcutaneously with 40% $CCl_4$ solution (Beijing Tongguang Fine Chemical Co., Ltd.) at a dose of 0.72 mg/100 g for 4 consecutive weeks to obtain a diabetes mellitus+NASH model.

In the experiment, 35 of the above model mice were used, and animals with blood glucose of about 7 to 13 mmol/L were selected. According to their blood glucose levels, they were randomly divided into a blank control group, a model group, a BJMU group (gemfibrozil), a BJMU-1 group, a BJMU-2 Group and a BJMU-3 group, 7 animals in each group (the model group and each administration group were modeled according to the animal modeling method). Intragastric administration was adopted with an administration volume of 10 ml/kg. The blank control group and the model group were administrated with 1% Tween 80-saline; the BJMU group was administrated with a dose of 50 mg/kg, the BJMU-1 group was administrated with a dose of 50 mg/kg, the BJMU-2 group was administrated with a dose of 50 mg/kg, and the BJMU-3 group was administrated with a dose of 50 mg/kg. The administration was performed once a day for 28 consecutive days. From the day of oral administration, the physiological changes of the animals were observed every day. Blood glucose was measured every week, and blood glucose difference ($\Delta$) was calculated by the following formula: blood glucose difference ($\Delta$)=the blood glucose of the day—the initial blood glucose (the initial blood glucose difference was zero). After the administration, the animals were sacrificed, and the internal organs and epididymal fat were taken out for experiments. White epididymal fat was taken from each group of mice and weighed. According to the corresponding body weight, the weight ratio of white fat was calculated. Before the mice were sacrificed, 3 mice in each group were randomly selected and subjected to magnetic resonance imaging (MRI) (EchoMRI-700 body fat tester) so as to measure body fat content.

For mice in each experimental group, blood was collected and serum was separated, and liver was taken for wet-weight measurement after necropsy; liver tissue was taken and fixed for pathological examination, H.E. staining and oil red O staining (Wuhan Zishan Biotechnology Co., Ltd.) were performed, and mouse liver lesions were observed under light microscope; routine examination of blood was performed by Animal Laboratory Department, Health Science Center of Peking University to measure the following indexes: white blood cell count (WBC), red blood cell count (RBC), lymphocyte count (LY), platelet (PLT) and so on; biochemical laboratory examination of blood was performed by Laboratory Medicine, Third Hospital, Peking University to measure the following indexes: triglycerides (TG), total cholesterol (T-CHO), high-density lipoprotein cholesterol (HDL-C), low-density lipoprotein cholesterol (LDL-C) and so on.

Figure 9:
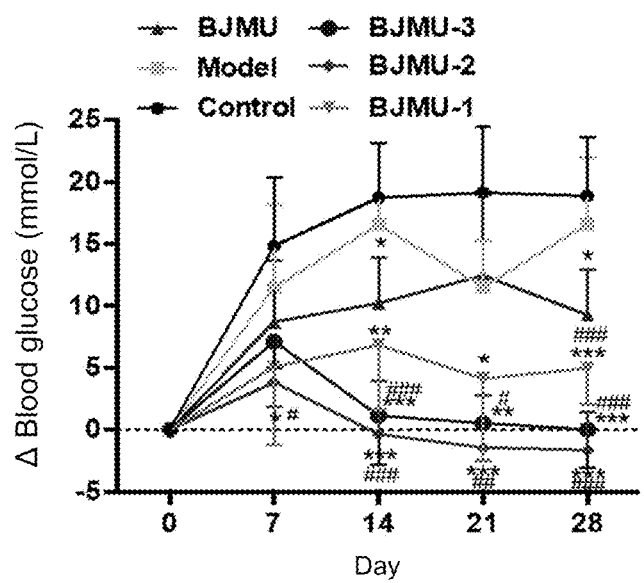
FIG. 9 shows the effects of the compound on the blood glucose level of diabetes mellitus+NASH model mice, in which compared with the model control group, *P<0.05, P<0.01, *P<0.001; compared with the BJMU group, #P<0.05, ##P<0.01, ###P<0.001.

The measurement results of blood glucose were shown in FIG. 9. The tested compounds BJMU-1, BJMU-2 and BJMU-3 could significantly reduce the blood glucose level of the diabetes mellitus+NASH model mice, and the blood glucose level almost returned to the normal level 14 days after the administration. In contrast, gemfibrozil did not exhibit significant hypoglycemic activity. This result indicated that the compound of the present invention exhibited significant hypoglycemic activity.

Figure 10:
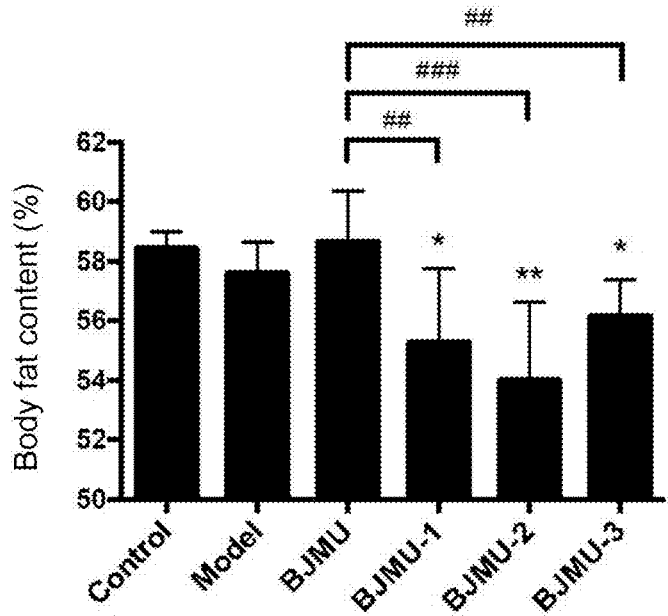
FIG. 10 shows the effects of the compound on the body fat content of diabetes mellitus+NASH model mice, determined by MRI in which compared with the model control group, *P<0.05, P<0.01, *P<0.001; compared with the BJMU group, #P<0.05, ##P<0.01, ###P<0.001.

The measurement results of body fat were shown in FIG. 10. The tested compounds BJMU-1, BJMU-2 and BJMU-3 could significantly reduce the body fat content of mice; in contrast, gemfibrozil did not show an activity of reducing body fat. The above results indicated that the compound of the present invention had significant activity of reducing body fat.

Figure 11:
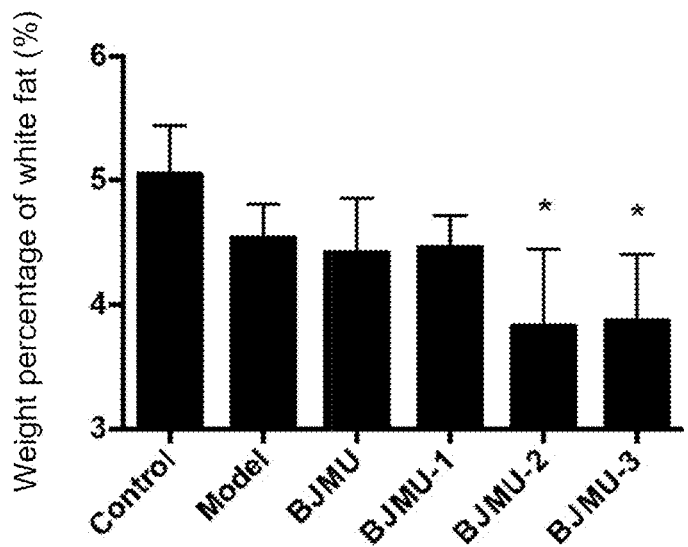
FIG. 11 shows the effects of the compound on weight ratio of the epididymal white fat of diabetes mellitus+NASH model mice, in which compared with the model control group, *P<0.05, P<0.01, *P<0.001.

The measurement results of white fat weight ratio were shown in FIG. 11. The tested compounds BJMU-2 and BJMU-3 could significantly reduce the weight ratio of mouse epididymal fat, and were better than gemfibrozil. The above results further indicated that the compound of the present invention had significant activity of reducing body fat.

The measurement results of blood lipid indexes were shown in the table below. The tested compounds BJMU-1, BJMU-2 and BJMU-3 had better activity of lowering triglycerides than gemfibrozil. In particular, BJMU-2 could reduce total cholesterol content in blood of DB/DB mice; in contrast, gemfibrozil did not show an activity of lowering total cholesterol in blood. The above results indicated that the compound of the present invention had a more prominent effect of reducing blood lipids.

TABLE 3

Measurement results of blood lipid indexes

| Group | Dose (mg/kg) | CHOL (mmol/L) | TGL (mmol/L) | AHDL (mmol/L) | ALDL (mmol/L) |
|---|---|---|---|---|---|
| Blank control | 0 | 3.44 ± 0.51 | 3.05 ± 1.43 | 1.91 ± 0.21 | 0.41 ± 0.1 |

TABLE 3-continued

Measurement results of blood lipid indexes

| Group | Dose (mg/kg) | CHOL (mmol/L) | TGL (mmol/L) | AHDL (mmol/L) | ALDL (mmol/L) |
|---|---|---|---|---|---|
| Model group | 0 | 4.96 ± 1.04 | 2.27 ± 1.22 | 2.29 ± 0.45 | 0.7 ± 0.45 |
| BJMU | 50 | 5.37 ± 0.88 | 1.86 ± 0.66 | 2.68 ± 0.31 | 0.7 ± 0.16 |
| BJMU-1 | 50 | 4.85 ± 0.7 | 1.77 ± 0.65 | 2.34 ± 0.24 | 0.49 ± 0.06 |
| BJMU-2 | 50 | 3.78 ± 0.45* | 1.73 ± 0.41 | 2.15 ± 0.29 | 0.48 ± 0.05* |
| BJMU-3 | 50 | 4.42 ± 1.77 | 1.86 ± 0.99 | 2.27 ± 0.84 | 0.52 ± 0.14 |

Note:
Compared with the model control group,
*P < 0.05,
**P < 0.01.
CHOL: total cholesterol; TGL: triglycerides; AHDL: high density lipoprotein, ALDL: low density lipoprotein.

Figure 12A:
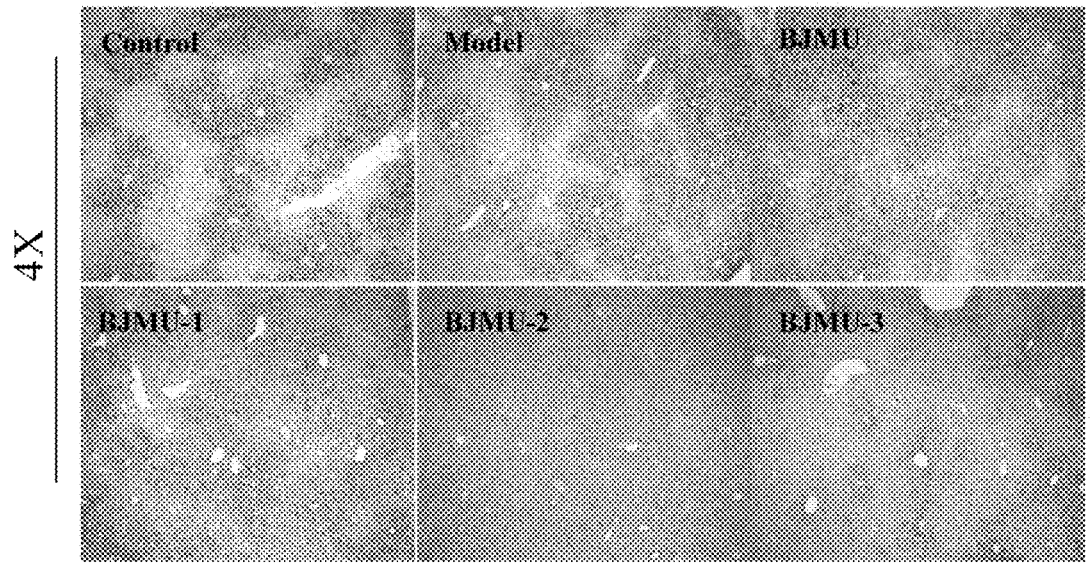
FIGS. 12A to 12B show the effects of the compound on the fat content in the liver tissue of diabetes mellitus+NASH model mice.
Figure 12B:
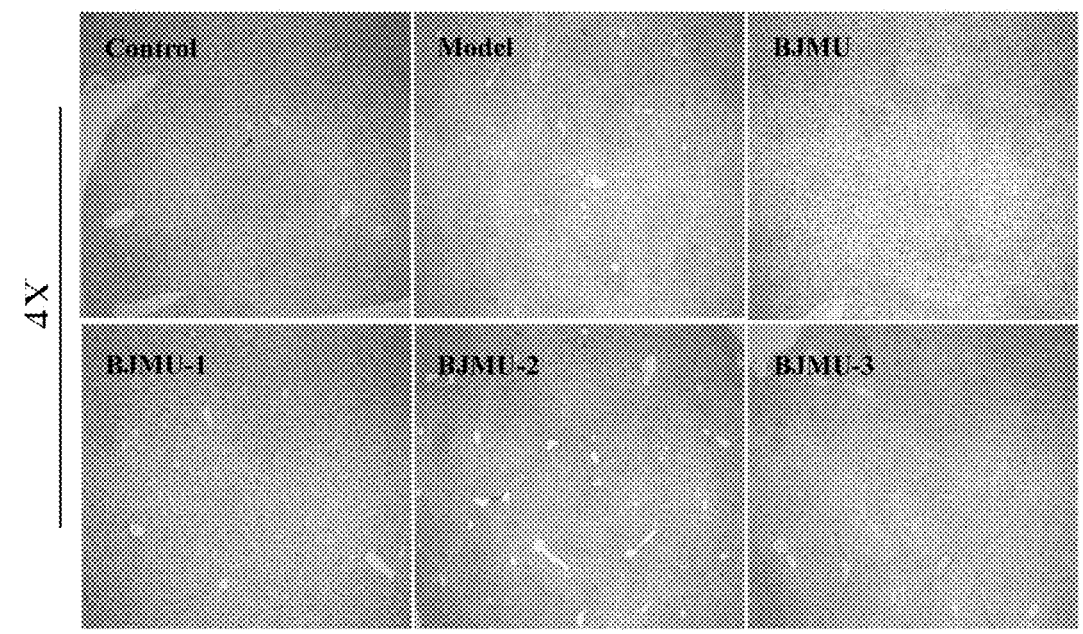

The pathological examination results of liver tissues were shown in FIGS. 12A to 12B. The results showed that the tested compounds BJMU-1, BJMU-2 and BJMU-3 could significantly reduce the fat content in liver of model mice. In contrast, gemfibrozil did not exhibit the aforementioned activity. The above results indicated that the compound of the present invention not only had a significant activity in reducing blood fat, but also a significant activity in reducing body fat.

In addition, the measurement data of mouse liver function and kidney function indexes (Table 4) showed that the tested compounds would not cause liver and kidney toxicity after continuous intragastric administration at a dose of 50 mg/kg for one month. This result indicated that the compound of the present invention had good in vivo safety.

TABLE 4

Data of mouse liver function and kidney function indexes

| Group | Dose (mg/kg) | AST (U/L) | ALT (U/L) | BUN (mmol/L) | CREA (umol/L) | CK (U/L) |
|---|---|---|---|---|---|---|
| Blank control | 0 | 245.11 ± 86.34 | 167.89 ± 114.44 | 10.92 ± 1.23 | 27 ± 10.03 | 1135.78 ± 690.2 |
| Model group | 0 | 227.75 ± 79.81 | 120.25 ± 27.06 | 12.81 ± 4.49 | 23.29 ± 6.58 | 1346 ± 650.43 |
| BJMU | 50 | 235.14 ± 41.06 | 134.14 ± 38.71 | 11.96 ± 2.26 | 22.29 ± 3.45 | 1222.14 ± 392.96 |
| BJMU-1 | 50 | 216.43 ± 60.6 | 114.86 ± 51.2 | 9.89 ± 1.31 | 19 ± 1.63 | 1297.71 ± 814.48 |
| BJMU-2 | 50 | 233.67 ± 47.75 | 115.57 ± 39.12 | 11.95 ± 1.81 | 22.5 ± 7.12 | 1406.33 ± 458.77 |
| BJMU-3 | 50 | 257 ± 83 | 125.14 ± 51.99 | 9.29 ± 3.44 | 21.33 ± 10.52 | 1674.71 ± 864.05 |

The above results indicated that the tested compounds BJMU-1, BJMU-2 and BJMU-3 could reduce blood glucose and blood lipid levels, and could reduce body fat and liver fat content. In particular, BJMU-2 could be metabolized by the liver to produce metabolites BJMU-415 and 502; since these two compounds had activity no less or even better than that of BJMU-2 in cell-level experiments, it could be reasonably expected that BJMU-415 and 502 would have at least the above-mentioned excellent in vivo activity of BJMU-2.

Although the specific embodiments of the present invention have been described in detail, those skilled in the art will understand that various modifications and substitutions can be made to those details according to all the teachings that have been disclosed, and these changes are all within the protection scope of the present invention. The full scope of the present invention is given by the appended claims and any equivalents thereof.

REFERENCES

[1] Reddy P, Lent-Schochet D, Ramakrishnan N, McLaughlin M, Jialal I. Metabolic syndrome is an inflammatory disorder: A conspiracy between adipose tissue and phagocytes. Clin Chim Acta 2019; 496:35-44.
[2] Chen Z, Yu R, Xiong Y, Du F, Zhu S. A vicious circle between insulin resistance and inflammation in nonalcoholic fatty liver disease. Lipids Health Dis 2017; 16:203.
[3] Catrysse L, van Loo G. Inflammation and the Metabolic Syndrome: The Tissue-Specific Functions of NF-kappaB. Trends Cell Biol 2017; 27:417-429.
[4] Esser N, Paquot N, Scheen A J. Anti-inflammatory agents to treat or prevent type 2 diabetes, metabolic syndrome and cardiovascular disease. Expert Opin Investig Drugs 2015; 24:283-307.
[5] Chartoumpekis D V, Kensler T W. New player on an old field; the keap1/Nrf2 pathway as a target for treatment of type 2 diabetes and metabolic syndrome. Curr Diabetes Rev 2013; 9:137-145.
[6] Chowdhry S, Nazmy M H, Meakin P J, Dinkova-Kostova A T, Walsh S V, Tsujita T, Dillon J F, et al. Loss of Nrf2 markedly exacerbates nonalcoholic steatohepatitis. Free Radic Biol Med 2010; 48:357-371.
Santos J C, Valentim I B, de Araujo O R, Ataide Tda R, Goulart M O. Development of nonalcoholic hepatopathy: contributions of oxidative stress and advanced glycation end products. Int J Mol Sci 2013; 14:19846-19866.
[7] Shimozono R, Asaoka Y, Yoshizawa Y, Aoki T, Noda H, Yamada M, Kaino M, et al. Nrf2 activators attenuate the progression of nonalcoholic steatohepatitis-related fibrosis in a dietary rat model. Mol Pharmacol 2013; 84:62-70.
[8] Spahis S, Delvin E, Borys J M, Levy E. Oxidative Stress as a Critical Factor in Nonalcoholic Fatty Liver Disease Pathogenesis. Antioxid Redox Signal 2017; 26:519-541.

What is claimed is:

1. A method for prevention or treatment of a metabolic disease in a subject, the method comprising administering to a subject in need thereof an effective amount of a compound represented by Formula (Ia), its pharmaceutically acceptable salt or ester, prodrug, stereoisomer, hydrate, solvate or crystal form, or metabolite form thereof, or any combination or mixture thereof,

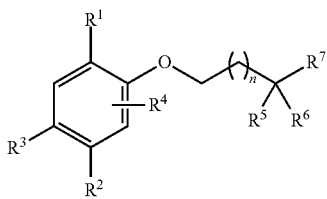

Formula (Ia)

wherein, $R^1$ and $R^2$ are each independently $C_1$-$C_4$ alkyl or $C_1$-$C_4$ alkoxy, and the $C_1$-$C_4$ alkyl or $C_1$-$C_4$ alkoxy is optionally substituted with one or several substituents independently selected from: halogen and hydroxyl;

$R^3$ is halogen;

$R^4$ is hydrogen, halogen, nitro, hydroxyl, $C_1$-$C_4$ alkyl or $C_1$-$C_4$ alkoxy, wherein the $C_1$-$C_4$ alkyl is optionally substituted with one or several substituents independently selected from halogen, and hydroxyl;

$R^5$ and $R^6$ are each independently $C_1$-$C_4$ alkyl;

$R^7$ is —C(O)X or cyano; wherein X is hydroxyl or $C_1$-$C_4$ alkoxy;

n is 1, 2, 3 or 4.

2. A method for prevention or treatment of a disease associated with PPARα and/or PPARγ in a subject, the method comprising administering to a subject in need thereof an effective amount of a compound represented by Formula (Ia), its pharmaceutically acceptable salt or ester, prodrug, stereoisomer, hydrate, solvate or crystal form, or metabolite form thereof, or any combination or mixture thereof,

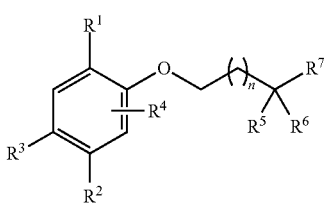

Formula (Ia)

wherein, $R^1$ and $R^2$ are each independently $C_1$-$C_4$ alkyl or $C_1$-$C_4$ alkoxy, and the $C_1$-$C_4$ alkyl or $C_1$-$C_4$ alkoxy is optionally substituted with one or several substituents independently selected from halogen and hydroxyl;

$R^3$ is halogen;
$R^4$ is hydrogen, halogen, nitro, hydroxyl, $C_1$-$C_4$ alkyl or $C_1$-$C_4$ alkoxy, wherein the $C_1$-$C_4$ alkyl is optionally substituted with one or several substituents independently selected from halogen and hydroxyl;
$R^5$ and $R^6$ are each independently $C_1$-$C_4$ alkyl;
$R^7$ is —C(O)X or cyano; wherein X is hydroxyl or $C_1$-$C_4$ alkoxy;
n is 1, 2, 3 or 4.

3. A method for reducing body weight, reducing body fat, reducing a liver fat fraction, preventing or treating obesity, and/or preventing or treating non-alcoholic fatty liver disease (NAFLD) in a subject, the method comprising administering to a subject in need thereof an effective amount of a compound represented by Formula (Ia), its pharmaceutically acceptable salt or ester, prodrug, stereoisomer, hydrate, solvate or crystal form, or metabolite form thereof, or any combination or mixture thereof,

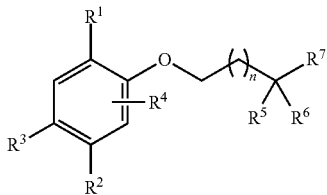

Formula (Ia)

wherein,
$R^1$ and $R^2$ are each independently $C_1$-$C_4$ alkyl or $C_1$-$C_4$ alkoxy, and the $C_1$-$C_4$ alkyl or $C_1$-$C_4$ alkoxy is optionally substituted with one or several substituents independently selected from halogen and hydroxyl;
$R^3$ is halogen;
$R^4$ is hydrogen, halogen, nitro, hydroxyl, $C_1$-$C_4$ alkyl or $C_1$-$C_4$ alkoxy, wherein the $C_1$-$C_4$ alkyl is optionally substituted with one or several substituents independently selected from halogen and hydroxyl;
$R^5$ and $R^6$ are each independently $C_1$-$C_4$ alkyl;
$R^7$ is —C(O)X or cyano; wherein X is hydroxyl or $C_1$-$C_4$ alkoxy;
n is 1, 2, 3 or 4.

4. A method for reducing a blood glucose level, increasing insulin sensitivity, preventing or treating insulin resistance, and/or preventing or treating diabetes mellitus in a subject, the method comprising administering to a subject in need thereof an effective amount of a compound represented by Formula (Ia), its pharmaceutically acceptable salt or ester, prodrug, stereoisomer, hydrate, solvate or crystal form, or metabolite form thereof, or any combination or mixture thereof,

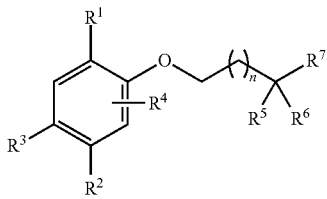

Formula (Ia)

wherein,
$R^1$ and $R^2$ are each independently $C_1$-$C_4$ alkyl or $C_1$-$C_4$ alkoxy, and the $C_1$-$C_4$ alkyl or $C_1$-$C_4$ alkoxy is optionally substituted with one or several substituents independently selected from halogen and hydroxyl;
$R^3$ is halogen;
$R^4$ is hydrogen, halogen, nitro, hydroxyl, $C_1$-$C_4$ alkyl or $C_1$-$C_4$ alkoxy, wherein the $C_1$-$C_4$ alkyl is optionally substituted with one or several substituents independently selected from halogen and hydroxyl;
$R^5$ and $R^6$ are each independently $C_1$-$C_4$ alkyl;
$R^7$ is —C(O)X or cyano; wherein X is hydroxyl or $C_1$-$C_4$ alkoxy;
n is 1, 2, 3 or 4.

5. A method for lowering a blood total cholesterol level, lowering a blood triglyceride level, lowering a blood low-density lipoprotein level, and/or increasing a blood high-density lipoprotein level in a subject, the method comprising administering to a subject in need thereof an effective amount of a compound represented by Formula (Ia), its pharmaceutically acceptable salt or ester, prodrug, stereoisomer, hydrate, solvate or crystal form, or metabolite form thereof, or any combination or mixture thereof,

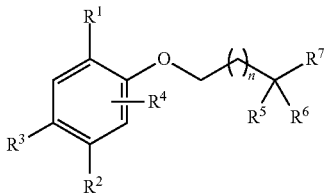

Formula (Ia)

wherein,
$R^1$ and $R^2$ are each independently $C_1$-$C_4$ alkyl or $C_1$-$C_4$ alkoxy, and the $C_1$-$C_4$ alkyl or $C_1$-$C_4$ alkoxy is optionally substituted with one or several substituents independently selected from halogen and hydroxyl;
$R^3$ is halogen;
$R^4$ is hydrogen, halogen, nitro, hydroxyl, $C_1$-$C_4$ alkyl or $C_1$-$C_4$ alkoxy, wherein the $C_1$-$C_4$ alkyl is optionally substituted with one or several substituents independently selected from halogen and hydroxyl;
$R^5$ and $R^6$ are each independently $C_1$-$C_4$ alkyl;
$R^7$ is —C(O)X or cyano; wherein X is hydroxyl or $C_1$-$C_4$ alkoxy;
n is 1, 2, 3 or 4.

6. The method of claim 1, wherein, the metabolic disease is selected from obesity, non-alcoholic fatty liver disease, metabolic syndrome, type 2 diabetes mellitus, type 1 diabetes mellitus, insulin resistance, hyperinsulinemia, glucose intolerance, hyperglycemia, hyperlipidemia, and secondary complications of these diseases.

7. The method of claim 1, wherein the compound is selected from:
5-(4-chloro-2,5-dimethylphenoxy)-2,2-dimethylpentanoic acid (BJMU-1);
5-(4-bromo-2,5-dimethylphenoxy)-2,2-dimethylpentanoic acid (BJMU-2);
5-(4-fluoro-2,5-dimethylphenoxy)-2,2-dimethylpentanoic acid (BJMU-3);
5-(2,4-dibromo-3,6-dimethylphenoxy)-2,2-dimethylpentanoic acid (BJMU-109);
5-(4-bromo-2,5-diethylphenoxy)-2,2-dimethylpentanoic acid (BJMU-310);
5-(4-bromo-2,3,5-trimethylphenoxy)-2,2-dimethylpentanoic acid (BJMU-315);

5-(4-bromo-2,3,6-trimethylphenoxy)-2,2-dimethylpentanoic acid (BJMU-409);
5-(4-bromo-2-iodo-3,6-dimethylphenoxy)-2,2-dimethylpentanoic acid (BJMU-413);
5-(4-bromo-2-methoxy-5-methylphenoxy)-2,2-dimethylpentanoic acid (BJMU-412);
5-(4-bromo-3,6-dimethyl-2-nitrophenoxy)-2,2-dimethylpentanoic acid (BJMU-414);
5-(4-bromo-2-hydroxy-3,6-dimethylphenoxy)-2,2-dimethylpentanoic acid (BJMU-415);
5-(4-bromo-3-hydroxy-2,5-dimethylphenoxy)-2,2-dimethylpentanoic acid (BJMU-416);
5-(4-bromo-2-(hydroxymethyl)-5-methylphenoxy)-2,2-dimethylpentanoic acid (BJMU-502);
5-(4-bromo-2,5-dimethylphenoxy)-2,2-dimethylvaleronitrile (BJMU-309);
5-(4-bromo-2,5-dimethylphenoxy)-2-ethyl-2-methylpentanoic acid (BJMU-401);
5-(4-bromo-2-ethyl-5-methylphenoxy)-2,2-dimethylpentanoic acid (BJMU-410);
5-(4-bromo-2,5-dimethoxyphenoxy)-2,2-dimethylpentanoic acid (BJMU-201);
4-(4-bromo-2,5-dimethylphenoxy)-2,2-dimethylbutanoic acid (BJMU-111); and
6-(4-bromo-2,5-dimethylphenoxy)-2,2-dimethylhexanoic acid (BJMU-403).

8. The method of claim 2, wherein the compound is selected from:
5-(4-chloro-2,5-dimethylphenoxy)-2,2-dimethylpentanoic acid (BJMU-1);
5-(4-bromo-2,5-dimethylphenoxy)-2,2-dimethylpentanoic acid (BJMU-2);
5-(4-fluoro-2,5-dimethylphenoxy)-2,2-dimethylpentanoic acid (BJMU-3);
5-(2,4-dibromo-3,6-dimethylphenoxy)-2,2-dimethylpentanoic acid (BJMU-109);
5-(4-bromo-2,5-diethylphenoxy)-2,2-dimethylpentanoic acid (BJMU-310);
5-(4-bromo-2,3,5-trimethylphenoxy)-2,2-dimethylpentanoic acid (BJMU-315);
5-(4-bromo-2,3,6-trimethylphenoxy)-2,2-dimethylpentanoic acid (BJMU-409);
5-(4-bromo-2-iodo-3,6-dimethylphenoxy)-2,2-dimethylpentanoic acid (BJMU-413);
5-(4-bromo-2-methoxy-5-methylphenoxy)-2,2-dimethylpentanoic acid (BJMU-412);
5-(4-bromo-3,6-dimethyl-2-nitrophenoxy)-2,2-dimethylpentanoic acid (BJMU-414);
5-(4-bromo-2-hydroxy-3,6-dimethylphenoxy)-2,2-dimethylpentanoic acid (BJMU-415);
5-(4-bromo-3-hydroxy-2,5-dimethylphenoxy)-2,2-dimethylpentanoic acid (BJMU-416);
5-(4-bromo-2-(hydroxymethyl)-5-methylphenoxy)-2,2-dimethylpentanoic acid (BJMU-502);
5-(4-bromo-2,5-dimethylphenoxy)-2,2-dimethylvaleronitrile (BJMU-309);
5-(4-bromo-2,5-dimethylphenoxy)-2-ethyl-2-methylpentanoic acid (BJMU-401);
5-(4-bromo-2-ethyl-5-methylphenoxy)-2,2-dimethylpentanoic acid (BJMU-410);
5-(4-bromo-2,5-dimethoxyphenoxy)-2,2-dimethylpentanoic acid (BJMU-201);
4-(4-bromo-2,5-dimethylphenoxy)-2,2-dimethylbutanoic acid (BJMU-111); and
6-(4-bromo-2,5-dimethylphenoxy)-2,2-dimethylhexanoic acid (BJMU-403).

9. The method of claim 3, wherein the compound is selected from:
5-(4-chloro-2,5-dimethylphenoxy)-2,2-dimethylpentanoic acid (BJMU-1);
5-(4-bromo-2,5-dimethylphenoxy)-2,2-dimethylpentanoic acid (BJMU-2);
5-(4-fluoro-2,5-dimethylphenoxy)-2,2-dimethylpentanoic acid (BJMU-3);
5-(2,4-dibromo-3,6-dimethylphenoxy)-2,2-dimethylpentanoic acid (BJMU-109);
5-(4-bromo-2,5-diethylphenoxy)-2,2-dimethylpentanoic acid (BJMU-310);
5-(4-bromo-2,3,5-trimethylphenoxy)-2,2-dimethylpentanoic acid (BJMU-315);
5-(4-bromo-2,3,6-trimethylphenoxy)-2,2-dimethylpentanoic acid (BJMU-409);
5-(4-bromo-2-iodo-3,6-dimethylphenoxy)-2,2-dimethylpentanoic acid (BJMU-413);
5-(4-bromo-2-methoxy-5-methylphenoxy)-2,2-dimethylpentanoic acid (BJMU-412);
5-(4-bromo-3,6-dimethyl-2-nitrophenoxy)-2,2-dimethylpentanoic acid (BJMU-414);
5-(4-bromo-2-hydroxy-3,6-dimethylphenoxy)-2,2-dimethylpentanoic acid (BJMU-415);
5-(4-bromo-3-hydroxy-2,5-dimethylphenoxy)-2,2-dimethylpentanoic acid (BJMU-416);
5-(4-bromo-2-(hydroxymethyl)-5-methylphenoxy)-2,2-dimethylpentanoic acid (BJMU-502);
5-(4-bromo-2,5-dimethylphenoxy)-2,2-dimethylvaleronitrile (BJMU-309);
5-(4-bromo-2,5-dimethylphenoxy)-2-ethyl-2-methylpentanoic acid (BJMU-401);
5-(4-bromo-2-ethyl-5-methylphenoxy)-2,2-dimethylpentanoic acid (BJMU-410);
5-(4-bromo-2,5-dimethoxyphenoxy)-2,2-dimethylpentanoic acid (BJMU-201);
4-(4-bromo-2,5-dimethylphenoxy)-2,2-dimethylbutanoic acid (BJMU-111); and
6-(4-bromo-2,5-dimethylphenoxy)-2,2-dimethylhexanoic acid (BJMU-403).

10. The method of claim 4, wherein the compound is selected from:
5-(4-chloro-2,5-dimethylphenoxy)-2,2-dimethylpentanoic acid (BJMU-1);
5-(4-bromo-2,5-dimethylphenoxy)-2,2-dimethylpentanoic acid (BJMU-2);
5-(4-fluoro-2,5-dimethylphenoxy)-2,2-dimethylpentanoic acid (BJMU-3);
5-(2,4-dibromo-3,6-dimethylphenoxy)-2,2-dimethylpentanoic acid (BJMU-109);
5-(4-bromo-2,5-diethylphenoxy)-2,2-dimethylpentanoic acid (BJMU-310);
5-(4-bromo-2,3,5-trimethylphenoxy)-2,2-dimethylpentanoic acid (BJMU-315);
5-(4-bromo-2,3,6-trimethylphenoxy)-2,2-dimethylpentanoic acid (BJMU-409);
5-(4-bromo-2-iodo-3,6-dimethylphenoxy)-2,2-dimethylpentanoic acid (BJMU-413);
5-(4-bromo-2-methoxy-5-methylphenoxy)-2,2-dimethylpentanoic acid (BJMU-412);
5-(4-bromo-3,6-dimethyl-2-nitrophenoxy)-2,2-dimethylpentanoic acid (BJMU-414);
5-(4-bromo-2-hydroxy-3,6-dimethylphenoxy)-2,2-dimethylpentanoic acid (BJMU-415);
5-(4-bromo-3-hydroxy-2,5-dimethylphenoxy)-2,2-dimethylpentanoic acid (BJMU-416);

5-(4-bromo-2-(hydroxymethyl)-5-methylphenoxy)-2,2-dimethylpentanoic acid (BJMU-502);

5-(4-bromo-2,5-dimethylphenoxy)-2,2-dimethylvaleronitrile (BJMU-309);

5-(4-bromo-2,5-dimethylphenoxy)-2-ethyl-2-methylpentanoic acid (BJMU-401);

5-(4-bromo-2-ethyl-5-methylphenoxy)-2,2-dimethylpentanoic acid (BJMU-410);

5-(4-bromo-2,5-dimethoxyphenoxy)-2,2-dimethylpentanoic acid (BJMU-201);

4-(4-bromo-2,5-dimethylphenoxy)-2,2-dimethylbutanoic acid (BJMU-111); and 6-(4-bromo-2,5-dimethylphenoxy)-2,2-dimethylhexanoic acid (BJMU-403).

11. The method of claim 5, wherein the compound is selected from:

5-(4-chloro-2,5-dimethylphenoxy)-2,2-dimethylpentanoic acid (BJMU-1);

5-(4-bromo-2,5-dimethylphenoxy)-2,2-dimethylpentanoic acid (BJMU-2);

5-(4-fluoro-2,5-dimethylphenoxy)-2,2-dimethylpentanoic acid (BJMU-3);

5-(2,4-dibromo-3,6-dimethylphenoxy)-2,2-dimethylpentanoic acid (BJMU-109);

5-(4-bromo-2,5-diethylphenoxy)-2,2-dimethylpentanoic acid (BJMU-310);

5-(4-bromo-2,3,5-trimethylphenoxy)-2,2-dimethylpentanoic acid (BJMU-315);

5-(4-bromo-2,3,6-trimethylphenoxy)-2,2-dimethylpentanoic acid (BJMU-409);

5-(4-bromo-2-iodo-3,6-dimethylphenoxy)-2,2-dimethylpentanoic acid (BJMU-413);

5-(4-bromo-2-methoxy-5-methylphenoxy)-2,2-dimethylpentanoic acid (BJMU-412);

5-(4-bromo-3,6-dimethyl-2-nitrophenoxy)-2,2-dimethylpentanoic acid (BJMU-414);

5-(4-bromo-2-hydroxy-3,6-dimethylphenoxy)-2,2-dimethylpentanoic acid (BJMU-415);

5-(4-bromo-3-hydroxy-2,5-dimethylphenoxy)-2,2-dimethylpentanoic acid (BJMU-416);

5-(4-bromo-2-(hydroxymethyl)-5-methylphenoxy)-2,2-dimethylpentanoic acid (BJMU-502);

5-(4-bromo-2,5-dimethylphenoxy)-2,2-dimethylvaleronitrile (BJMU-309);

5-(4-bromo-2,5-dimethylphenoxy)-2-ethyl-2-methylpentanoic acid (BJMU-401);

5-(4-bromo-2-ethyl-5-methylphenoxy)-2,2-dimethylpentanoic acid (BJMU-410);

5-(4-bromo-2,5-dimethoxyphenoxy)-2,2-dimethylpentanoic acid (BJMU-201);

4-(4-bromo-2,5-dimethylphenoxy)-2,2-dimethylbutanoic acid (BJMU-111); and 6-(4-bromo-2,5-dimethylphenoxy)-2,2-dimethylhexanoic acid (BJMU-403).

* * * * *

SEQUENCE LISTING

<160> NUMBER OF SEQ ID NOS: 10

<210> SEQ ID NO 1
<211> LENGTH: 19
<212> TYPE: DNA
<213> ORGANISM: artificial
<220> FEATURE:
<223> OTHER INFORMATION: primer

<400> SEQUENCE: 1
cattacggag tccacgcgt                                    19

<210> SEQ ID NO 2
<211> LENGTH: 21
<212> TYPE: DNA
<213> ORGANISM: artificial
<220> FEATURE:
<223> OTHER INFORMATION: primer

<400> SEQUENCE: 2
accagcttga gtcgaatcgt t                                 21

<210> SEQ ID NO 3
<211> LENGTH: 23
<212> TYPE: DNA
<213> ORGANISM: artificial
<220> FEATURE:
<223> OTHER INFORMATION: primer

<400> SEQUENCE: 3
gtactgtcgg tttcagaaat gcc                               23

<210> SEQ ID NO 4
<211> LENGTH: 22
<212> TYPE: DNA
<213> ORGANISM: artificial
<220> FEATURE:
<223> OTHER INFORMATION: primer

<400> SEQUENCE: 4
atctccgcca acagcttctc ct                                22

<210> SEQ ID NO 5
<211> LENGTH: 22
<212> TYPE: DNA
<213> ORGANISM: artificial
<220> FEATURE:
<223> OTHER INFORMATION: primer

<400> SEQUENCE: 5
gctacgagga atatcagcac ga                                22

<210> SEQ ID NO 6
<211> LENGTH: 18
<212> TYPE: DNA
<213> ORGANISM: artificial
<220> FEATURE:
<223> OTHER INFORMATION: primer

<400> SEQUENCE: 6
tcacacggcg ctcttcaa                                     18

<210> SEQ ID NO 7
<211> LENGTH: 19
<212> TYPE: DNA
<213> ORGANISM: artificial

```
<220> FEATURE:
<223> OTHER INFORMATION: primer

<400> SEQUENCE: 7
ctgtaggacc attgtctcg                                          19

<210> SEQ ID NO 8
<211> LENGTH: 20
<212> TYPE: DNA
<213> ORGANISM: artificial
<220> FEATURE:
<223> OTHER INFORMATION: primer

<400> SEQUENCE: 8
ttacactctg cactccaaag                                         20

<210> SEQ ID NO 9
<211> LENGTH: 20
<212> TYPE: DNA
<213> ORGANISM: artificial
<220> FEATURE:
<223> OTHER INFORMATION: primer

<400> SEQUENCE: 9 caccccttg atatccttcc                                          20

<210> SEQ ID NO 10
<211> LENGTH: 20
<212> TYPE: DNA
<213> ORGANISM: artificial
<220> FEATURE:
<223> OTHER INFORMATION: primer

<400> SEQUENCE: 10
ttctccggca agtaccaact                                         20
```